US007582773B2

(12) United States Patent
Gundersen

(10) Patent No.: US 7,582,773 B2
(45) Date of Patent: Sep. 1, 2009

(54) SUBSTITUTED PHENYL INDOLES

(75) Inventor: Eric Gould Gundersen, Royersford, PA (US)

(73) Assignee: Wyeth, Madison, NJ (US)

( * ) Notice: Subject to any disclaimer, the term of this patent is extended or adjusted under 35 U.S.C. 154(b) by 671 days.

(21) Appl. No.: 10/947,864

(22) Filed: Sep. 23, 2004

(65) Prior Publication Data
US 2005/0070592 A1 Mar. 31, 2005

Related U.S. Application Data

(60) Provisional application No. 60/505,981, filed on Sep. 25, 2003.

(51) Int. Cl.
*C07D 209/12* (2006.01)
*A61K 31/404* (2006.01)
(52) U.S. Cl. ...................................... 548/509; 514/415
(58) Field of Classification Search ................. 548/565, 548/577, 509
See application file for complete search history.

(56) References Cited

U.S. PATENT DOCUMENTS

| | | | | |
|---|---|---|---|---|
| 3,026,325 | A | 3/1962 | Heinzelman et al. | 548/496 |
| 3,476,770 | A | 11/1969 | Scherrer | 548/494 |
| 3,557,142 | A | 1/1971 | Bell | 548/516 |
| 3,843,683 | A | 10/1974 | Bell | 548/493 |
| 4,478,819 | A | 10/1984 | Hercelin et al. | 424/457 |
| 4,736,043 | A | 4/1988 | Michel et al. | 548/492 |
| 4,851,406 | A | 7/1989 | Martens et al. | 514/217.04 |
| 5,164,372 | A | 11/1992 | Matsuo et al. | 514/19 |
| 5,420,289 | A | 5/1995 | Musser et al. | 548/159 |
| 5,482,960 | A | 1/1996 | Berryman | 514/414 |
| 5,502,187 | A | 3/1996 | Ayer et al. | 544/117 |
| 5,541,343 | A | 7/1996 | Himmelsbach et al. | 514/424 |
| 5,612,360 | A | 3/1997 | Boyd et al. | 514/381 |
| 5,859,044 | A | 1/1999 | Dow et al. | 514/419 |
| 6,048,875 | A | 4/2000 | De Nanteuil et al. | 514/314 |
| 6,110,963 | A | 8/2000 | Malamas | 514/443 |
| 6,166,069 | A | 12/2000 | Malamas et al. | 514/469 |
| 6,232,322 | B1 | 5/2001 | Malamas et al. | 514/303 |
| 6,251,936 | B1 | 6/2001 | Wrobel et al. | 514/443 |
| 6,302,837 | B1 | 10/2001 | De Nanteuil et al. | 514/337 |
| 6,479,524 | B1 | 11/2002 | Priepke et al. | 514/352 |
| 6,599,929 | B2 | 7/2003 | Cho et al. | 514/415 |
| 6,787,556 | B1 | 9/2004 | Hargreaves et al. | 514/311 |
| 6,800,645 | B1 | 10/2004 | Cox et al. | 514/314 |
| 6,800,654 | B2 | 10/2004 | Mayer et al. | 514/381 |
| 6,844,358 | B2 | 1/2005 | Malamas et al. | 514/336 |
| 2003/0013732 | A1 | 1/2003 | Elokdah | 514/301 |
| 2003/0018067 | A1 | 1/2003 | Elokdah et al. | 514/469 |
| 2003/0060497 | A1 | 3/2003 | Gerlach et al. | 514/414 |
| 2003/0125371 | A1 | 7/2003 | Elokdah et al. | 514/419 |
| 2004/0116488 | A1 | 6/2004 | Jennings et al. | 514/374 |
| 2004/0116504 | A1 | 6/2004 | Elokdah et al. | 514/419 |
| 2004/0122070 | A1 | 6/2004 | Jennings | 514/374 |
| 2004/0138283 | A1 | 7/2004 | Jennings et al. | 514/414 |
| 2004/0204417 | A1 | 10/2004 | Perez et al. | 514/249 |
| 2004/0266788 | A1* | 12/2004 | Van Zandt et al. | 514/256 |
| 2005/0070584 | A1 | 3/2005 | Havran et al. | 514/357 |
| 2005/0070585 | A1 | 3/2005 | Elokdah et al. | 514/364 |
| 2005/0070587 | A1 | 3/2005 | Elokdah et al. | 514/381 |
| 2005/0096377 | A1 | 5/2005 | Hu | 514/419 |
| 2005/0113428 | A1 | 5/2005 | Gopalsamy et al. | 514/364 |
| 2005/0113436 | A1 | 5/2005 | Elokdah et al. | 514/411 |
| 2005/0113438 | A1 | 5/2005 | Hu et al. | 514/414 |
| 2005/0113439 | A1 | 5/2005 | Hu | 514/414 |
| 2005/0119296 | A1 | 6/2005 | Elokdah et al. | 514/300 |
| 2005/0119326 | A1 | 6/2005 | Havran et al. | 514/414 |
| 2005/0119327 | A1 | 6/2005 | Hu | 514/414 |
| 2005/0215626 | A1 | 9/2005 | Havran et al. | 514/469 |
| 2006/0020003 | A1 | 1/2006 | Commons et al. | 514/374 |
| 2006/0052348 | A1 | 3/2006 | Commons et al. | 514/92 |
| 2006/0052349 | A1 | 3/2006 | Commons et al. | 514/95 |
| 2006/0052420 | A1 | 3/2006 | Commons | 514/340 |

FOREIGN PATENT DOCUMENTS

| | | |
|---|---|---|
| DE | 3147276 A1 | 6/1983 |
| DE | 43 38 770 A1 | 5/1995 |
| DE | 19543639 A1 | 5/1997 |
| DE | 19753522 | 6/1999 |
| EP | 0 416 609 A2 | 3/1991 |
| EP | 0 508 723 A1 | 10/1992 |
| EP | 0 512 570 A1 | 11/1992 |
| EP | 0 540 956 A1 | 5/1993 |
| EP | 0 655 439 A2 | 5/1995 |
| EP | 0 759 434 A1 | 2/1997 |
| EP | 0 819 686 A1 | 1/1998 |
| EP | 0 822 185 A1 | 2/1998 |

(Continued)

OTHER PUBLICATIONS

Cancer and Metastasis Reviews (1998), 17 (1), 91-106.*
Science (1999), vol. 286, 531-537.*
Cancer [online], [retrieved on Jul. 6, 2007]. Retrieved from the Internet, URL; http://www.nlm.nih.gov/medlineplus/cancer.html>.*
Cancer [online],[retrieved on Jul. 6, 2007]. Retrieved from the Internet, URL; http://en.wikipedia.org/wiki/Cancer>.*
Cecil Textbook of Medicine, 20$^{th}$ edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieed on Sep. 23, 2003]. Retrieved from the Internet, URL; http://www.cnn.com/2003/HEALTH/conditions/09/24/alzheimers.drug.ap/indexhtml>.*
Diabetes Mellitus {DM} [online], [retrieved on Apr. 17, 2007]. Retrieved from the Internet, URL; http://www.merck.com/mmpe/print/sec12/ch158/ch158b.html>.*

(Continued)

*Primary Examiner*—Rebecca L Anderson
*Assistant Examiner*—Shawquia Young
(74) *Attorney, Agent, or Firm*—Mabel Ng; Scott Larsen; David Kurlandsky

(57) ABSTRACT

The present invention relates generally to substituted phenyl indoles and methods of using them, for example as PAI-1 inhibitors.

26 Claims, No Drawings

FOREIGN PATENT DOCUMENTS

| | | |
|---|---|---|
| EP | 0 955 299 A1 | 11/1999 |
| EP | 1 092 716 | 4/2001 |
| EP | 1 156 045 A1 | 11/2001 |
| FR | 2 244 499 A1 | 4/1975 |
| FR | 2 777 886 A1 | 10/1999 |
| FR | 2 799 756 A1 | 4/2001 |
| GB | 1 321 433 | 6/1973 |
| WO | WO 93/12084 A1 | 6/1993 |
| WO | 94/13637 A1 | 6/1994 |
| WO | WO 94/14434 A1 | 7/1994 |
| WO | 94/26738 A1 | 11/1994 |
| WO | 95/10513 A1 | 4/1995 |
| WO | 96/06840 A1 | 3/1996 |
| WO | 96/21656 A1 | 7/1996 |
| WO | 96/26207 A1 | 8/1996 |
| WO | 96/32379 A1 | 10/1996 |
| WO | WO 96/30358 A1 | 10/1996 |
| WO | 97/09308 A1 | 3/1997 |
| WO | WO 97/43260 A1 | 11/1997 |
| WO | 97/48697 A1 | 12/1997 |
| WO | WO 98/08818 A1 | 3/1998 |
| WO | 99/28297 A1 | 6/1999 |
| WO | 99/43651 A2 | 9/1999 |
| WO | 99/43654 A2 | 9/1999 |
| WO | 99/46260 A1 | 9/1999 |
| WO | WO 99/43672 A1 | 9/1999 |
| WO | 99/50268 A1 | 10/1999 |
| WO | 99/58519 A1 | 11/1999 |
| WO | WO 99/61435 A1 | 12/1999 |
| WO | 00/32180 A2 | 6/2000 |
| WO | 00/35919 A1 | 6/2000 |
| WO | 00/46195 A1 | 8/2000 |
| WO | 00/46197 A1 | 8/2000 |
| WO | 00/64876 A1 | 11/2000 |
| WO | 00/64888 A1 | 11/2000 |
| WO | 01/12187 A2 | 2/2001 |
| WO | WO 0218363 A2 * | 3/2002 |
| WO | 02/30895 A1 | 4/2002 |
| WO | 02/072549 A1 | 9/2002 |
| WO | 03/000253 A1 | 1/2003 |
| WO | 03/031409 A1 | 4/2003 |
| WO | 03/068742 A1 | 8/2003 |
| WO | 03/087087 A2 | 10/2003 |
| WO | 2004/052854 A2 | 6/2004 |

OTHER PUBLICATIONS

Polycystic ovary disease [online], [retrieved on Feb. 25, 2008]. Retrieved from the Internet, URL; http://www.nlm.nih.gov/medlineplus/ency/article/000369>.*

Chronic obstructive pulmonary disease [online] retrieved on Oct. 27, 2008. URL; http://www.nlm.nih.gov/medlineplus/ency/article/000091.htm.*

Krishnamurti, C. et al., "Plasminogen Activator Inhibitor: A Regulator of Ancrod-Induced Fibrin Deposition in Rabbits," Blood, 69(3): 798-803 (Mar. 1987).

Reilly, C. et al., "Both Circulating and Clot-Bound Plasminogen Activator-1 Inhibit Endogenous Fibrinolysis in the Rat," Arteriosclerosis and Thrombosis, 11(5): 1276-1286 (Sep./Oct. 1991).

Carmeliet, P. et al., "Plasminogen Activator Inhibitor -1 Gene-deficient Mice," Journal of Clinical Investigation, 92: 2756-2760 (Dec. 1993).

Rocha, E. et al., "The Relationship Between Impaired Fibrinolysis and Coronary Heart Disease," Fibrinolysis, 8: 294-303 (1994).

Aznar, J. et al., "Role of Plasminogen Activator Inhibitor Type 1 in the Pathogenesis of Coronary Artery Diseases," Haemostasis 24: 243-251 (1994).

Biemond, B. J. et al., "Thrombolysis and Reocclusion in Experimental Jugular Vein and Coronary Artery Thrombosis," Circulation, 91: 1175-1181 (1995).

Levi, M. et al., "Inhibition of Plasminogen Activator Inhibitor-1 Activity Results in Promotion of Endogenous Thrombolysis and Inhibition of Thrombus Experimental Thrombosis," Circulation 85:305-312 (1992).

Nordt, T. K. et al., "Differential Regulation by Troglitazone of Plasminogen Activator Inhibitor Type 1 in Human Hepatic and Vascular Cells," Journal of Clinical Endocrinology and Metabolism, 85(4):1563-1568 (2000).

Daci, E. et al., "Mice Lacking the Plasminogen Activator Inhibitor 1 are Protected from Trabecular Bone Loss Induced by Estrogen Deficiency," Journal of Bone and Mineral Research, 15(8):1510-1516 (Nov. 8, 2000).

Schneiderman J. et. al., "Increased type 1 plasminogen activator inhibitor gene expression in atherosclerotic human arteries," Proc Natl Acad Sci 89: 6998-7002 (Aug. 1992).

Juhan-Vague, I. et. al., "Deficient t-PA Release and Elevated PA Inhibitor Levels in Patients with Spontaneous or Recurrent Deep Venous Thrombosis," Thromb Haemost 57: 67-72 (1987).

Juhan-Vague, I. et. al., "PAI-1, Obesity, Insulin Resistance and Risk of Cardiovascular Events," Thromb Haemost 78: 565-660 (1997).

Hamsten, A. et. al., "Plasminogen Activator Inhibitor in Plasma: Risk Factor For Recurrent Myocardial Infarction," Lancet 2: 3-9 (Jul. 4, 1987).

Siemens, H. J. et. al., "Course of Molecular Hemostatic Markers During and After Different Surgical Procedures," J Clin Anesthesia 11: 622-629 (Dec. 1999).

Koh, K. et. al., "Effects of Hormone-Replacement Therapy on Fibrinolysis in Postmenopausal Women," N Engl J Med 336(10): 683-690 (Mar. 6, 1997).

Aggarwal et al., "A catalytic antibody programmed for torsional activation of amide bond hydrolysis," Chem. Eur. J., Jan. 25, 2003, 9(13), 3132-3142.

Ballantine, J. A., "The Chemistry of Bacteria," Journal of the Chemical Society Abstracts, 1957, 2222-2227.

Charlton, Peter, "The status of plasminogen activator inhibitor-1 as a therapeutic target," Expert Opinion On Investigational Drugs, May 1997, 6(5), 539-554.

Crandall, D. L. et al., "Characterization and comparative evaluation of a structurally unique PAI-1 inhibitor exhibiting oral in-vivo efficacy," Journal of Thrombosis and Haemostasis, Mar. 17, 2004, 2, 1422-1428.

Da Settimo, A. et al., "Reaction of indole derivatives with bromine, substitution, oxidation, and dimerization," J Org Chem, 1970, 35(8):2546-2551.

Delgado et al., Journal of Organic Chemistry (1993), 58(10), pp. 2862-2866.

Dillard R. D. et al., "Indole Inhibitors of Human Nonpancreatic Secretory Phospholipase $A_2$ 1. Indole-3-Acetamides", Journal of Medicinal Chemistry, American Chemical Society, 39(26), 5119-5136.

Guzzo, P.R. et al., "Synthesis of a conformationally constrained threonin-valine dipeptide mimetic: design of a potential inhibitor of plasminogen activator inhibitor-1," Tetrahedron Letters, 2002 43(1), 41-43.

Hipskind, P. A. et al., "Potent and selective 1,2,3-trisubstituted indole NPY Y-1 antagonists," J Med Chem, 1997, 40(23), 3712-3714.

Julia et al., CA 57:49169, 1962.

Malamas, M. S. et al., "Antihyperglycemic activity of new 1,2,4-oxadiazolidine-3,5-diones," Eur. J. Med. Chem., 2001, 36, 31-42.

Malamas, M.S. et al. "Novel benzofuran and benzothiophene biphenyls as inhibitors of protein tyrosine phosphatase 1B with antihyperglycemic properties," Journal of Medicinal Chemistry, Apr. 6, 2000, 43(7), 1293-1310.

Moody et al., CA 120:298300, 1994.

Shengeliya, M. S. et al., "N-Glycosides of 5-amino-2-(ethoxycarbonyl)indole," Zhurnal Organicheskoi Khimii, 1986, 22(9),1868-1873.

U.S. Appl. No. 10/947,711, filed Sep. 23, 2004, Gopalsamy et al.

Albers, "Advances in intravenous thrombolytic therapy for treatment of acute stroke", Neurology, 2001, 57(suppl 2):S77-S81.

Ashitani et al., "Elevated plasma procoagulant and fibrinolytic markers in patients with chronic obstructive pulmonary disease", Internal Medicine, 2002,41(3): 181-185.

Atiomo et al., "Immunohistochemical detection of plasminogen activator inhibitor-1 in polycystic ovaries", Gynecol Endocrinol, 2000, 14:162-168.

Berry et al., "Antithrombotic activity of a monoclonal antibody inducing the substrate form of plasminogen activator inhibitor type 1 in rat models of venous and arterial thrombosis", British Journal of Pharmacology, 1998, 125: 29-34.

Bianchi et al., "Immunohistochemical localization of the plasminogen activator inhibitor-1 in breast cancer", International Journal of Cancer, 1995, 60(5): 597-603.

Carmeliet et al.,"Biological effects of disruption of the tissue-type plasminogen activator, urokinase-type plasminogen activator, and plasminogen activator inhibitor-1 genes in mice", Ann. NY Acad Sci, 1995, 748:367-381.

Chazaud et al., "Promigratory effect of plasminogen activator inhibitor-1 on invasive breast cancer cell populations", American Journal of Pathology, 2002, 160(1): 237-246.

Egelund et al., "A regulatory hydrophobic area in the flexible joint region of plasminogen activator inhibitor-1, defined with fluorescent activity-neutralizing ligands. Ligand-induced serpin polymerization", Journal of Biological Chemistry, 2001, 276(16): 13077-13086.

Exley and Korchazhkina, "Plasmin cleaves $A\beta 42$ in vitro and prevents its aggregation into $\beta$-pleated sheet structures", Neuroreport, 2001, 12:2967-2970.

Fay et al.,"Human plasminogen activator inhibitor-1 (PAI-1) deficiency: characterization of a large kindred with a null mutation in the PAI-1 gene", Blood, 1997, 90:204-208.

Frandsen et al., "Plasminogen activator inhibitor type 1 (PAI-1) in cancer: a potential new target for antiinvasive and antimetastatic therapy", Drugs of the Future, 1998, 23(8): 873-883.

Glueck et al., "Continuing metformin throughout pregnancy in women with polycystic ovary syndrome appears to safely reduce first-trimester spontaneous abortion: a pilot study", Fertility and Sterility, 2001, 75(1): 46-52.

Hamano et al., "Expression of glomerular plasminogen activator inhibitor type 1 in glomerulonephritis", American Journal of Kidney Diseases, 2002, 39(4): 695-705.

Isogai, et al., "Plasminogen activator inhibitor-1 promotes angiogenesis by stimulating endothelial cell migration toward fibronectin",Cancer Research, 2001, 61(14): 5587-5594.

Kim et al., "Nonproteolytic neuroprotection by human recombinant tissue plasminogen activator", Science, 1999, 284:647-650.

Kingston et al., "In vitro stimulation of tissue-type plasminogen activator by Alzheimer amyloid beta-peptide analogues", Nat. Med. 1:138-142 (1995).

Lahlou et al., "Chronic graft dysfunction in renal transplant patients: potential role of plasminogen activator inhibitor type 1", Transplantation, 2002, 73: 1290-1295.

Ledesma et al., "Brain plasmin enhances APP $\alpha$-cleavage and $A\beta$ degradation and is reduced in Alzheimer's disease brains", EMBO Reports, 2000, 1:530-535.

Look et al., "Pooled analysis of prognostic impact of urokinase-type plasminogen activator and its inhibitor PAI-1 in 8377 breast cancer patients", Journal of the National Cancer Institute, 2002, 94(2): 116-128.

McGeer and McGeer, "The inflammatory response system of brain: implications for therapy of Alzheimer and other neurodegenerative diseases", Brain Res. Rev., 1995, 21:195-218.

Melchor et al., "The tissue plasminogen activator-plasminogen proteolytic cascade accelerates amyloid-$\beta$ ($A\beta$) degradation and inhibits $A\beta$-induced neurodegeneration", J. Neurosci., 2003, 23:8867-8871.

Periz and Fortini, "Proteolysis in Alzheimer's disease. Can plasmin tip the balance?", EMBO Reports, 2000, 1:477-478.

Qu et al., "Clinical significance of the expression of urokinase type plasminogen activator and plasminogen activator inhabitor in cervical carcinomas", China J. Cancer Prev Treat, 2003, 10(8): 821-824.

Roldan et al., "Hypofibrinolysis in atrial fibrillation", American Heart Journal, 1998, 136(6): 956-960.

Seeds et al., "Neuronal migration is retarded in mice lacking the tissue plasminogen activator gene", Proc. Nat. Acad. Sci., 1999, 96:14118-14123.

Simons et al., "Cholesterol depletion inhibits the generation of $\beta$-amyloid in hippocampal neurons", Proc. Nat. Acad. Sci., 1998, 95:6460-6464.

Sobel, "The potential influence of insulin and plasminogen activator inhibitor type 1 on the formation of vulnerable atherosclerotic plaques associated with type 2 diabetes", Proc Assoc Am Physicians, 1999, 111(4):313-8.

Takanashi and Inukai, "Insulin resistance and changes in the blood coagulation-fibrinolysis system after a glucose clamp technique in patients with type 2 diabetes mellitus", Journal of Medicine, 2000, 3:45-62.

Takazoe et al., "Increased plasminogen activator inhibitor activity and diabetes predict subsequent coronary events in patients with angina pectoris",Ann Med. 2001, 33(3):206-12.

Thogersen et al., "High plasminogen activator inhibitor and tissue plasminogen activator levels in plasma precede a first acute myocardial infarction in both men and women: evidence for the fibrinolytic system as an independent primary risk factor", Circulation, 1998, 98:2241-2247.

Tsirka et al., "An extracellular proteolytic cascade promotes neuronal degeneration in the mouse hippocampus", J. Neurosci.,1997, 17:543-552.

Tucker et al., "The plasmin system is induced by and degrades amyloid-$\beta$ aggregates", J. Neurosci., 2000, 20:3937-3946.

Tucker et al., "Tissue plasminogen activator requires plasminogen to modulate amyloid-$\beta$ neurotoxicity and deposition", J. Neurochem, 2000, 75:2172-2177.

Tucker et al., "Urokinase-type plasminogen activator inhibits amyloid-$\beta$ neurotoxicity and fibrillogenesis via plasminogen", J. Neurosci. Res., 2002, 70:249-255.

Van Nostrand and Porter, "Plasmin cleavage of the amyloid $\beta$-protein: alteration of secondary structure and stimulation of tissue plasminogen activator activity", Biochemistry, 1999, 38:11570-11576.

Wind et al., "Epitope mapping for four monoclonal antibodies against human plasminogen activator inhibitor type-1: implications for antibody-mediated PAI-1-neutralization and vitronectin-binding", Eur. J. Biochem, 2001, 268:1095-1106.

Wind et al., "Epitope mapping for four monoclonal antibodies against human plasminogen activator inhibitor type-1: implications for antibody-mediated PAI-1-neutralization and vitronectin-binding", European Journal of Biochemistry, 2001, 268(4):1095-1106.

Wnendt et al., "In vitro stimulation of tissue-type plasminogen activator by Alzheimer amyloid $\beta$-peptide analogues", Thromb. Res., 1997, 8:217-224.

Zhao et al., "Immunohistochemical expression of uPA, PAI-1, cathepsin D and apoptotic cells in ductal carcinoma in situ of the breast", Breast cancer, (Tokyo, Japan), 2002, 9(2): 118-26.

\* cited by examiner

SUBSTITUTED PHENYL INDOLES

CROSS-REFERENCE TO RELATED APPLICATIONS

This application claims the benefit of U.S. Provisional Application No. 60/505,981 filed Sep. 25, 2003, the entire disclosure of which is incorporated herein by reference.

BACKGROUND

The present invention relates generally to substituted phenyl indoles and methods of using them.

The serine protease inhibitor PAI-1 is one of the primary inhibitors of the fibrinolytic system. The fibrinolytic system includes the proenzyme plasminogen, which is converted to the active enzyme, plasmin, by one of two tissue type plasminogen activators, t-PA or u-PA. PAI-1 is the principal physiological inhibitor of t-PA and u-PA. One of plasmin's main responsibilities in the fibrinolytic system is to digest fibrin at the site of vascular injury. The fibrinolytic system, however, is not only responsible for the removal of fibrin from circulation but is also involved in several other biological processes including, for example, ovulation, embryogenesis, intima proliferation, angiogenesis, tumorigenesis, and atherosclerosis.

Elevated levels of PAI-1 have been associated with a variety of diseases and conditions including those associated with impairment of the fibrinolytic system. For example, elevated levels of PAI-1 have been implicated in thrombotic diseases, e.g., diseases characterized by formation of a thrombus that obstructs vascular blood flow locally or detaches and embolizes to occlude blood flow downstream. (Krishnamurti, *Blood*, 69, 798 (1987); Reilly, Arteriosclerosis and Thrombosis, 11, 1276 (1991); Carmeliet, *Journal of Clinical Investigation*, 92, 2756 (1993), Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases such as polycystic ovary syndrome (Nordt, *Journal of clinical Endocrinology and Metabolism*, 85, 4, 1563 (2000)), bone loss induced by estrogen deficiency (Daci, *Journal of Bone and Mineral Research*, 15, 8, 1510 (2000)), cystic fibrosis, diabetes, chronic periodontitis, lymphomas, diseases associated with extracellular matrix accumulation, malignancies and diseases associated with neoangiogenesis, inflammatory diseases, vascular damage associated with infections, and diseases associated with increased uPA levels such as breast and ovarian cancer.

In view of the foregoing, there exists a need for the identification of inhibitors of PAI-1 activity and for methods of using the identified inhibitors to modulate PAI-1 expression or activity in a subject in order to treat disorders associated with elevated PAI-1 levels.

SUMMARY

The present invention provides substituted phenyl indoles and methods of using them. In certain embodiments, substituted phenyl indoles of the invention include those of the Formula 1:

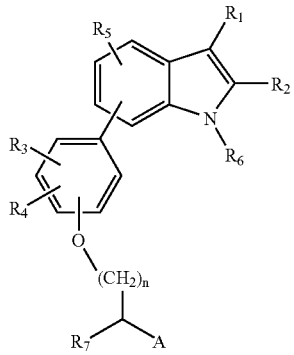

Formula 1 wherein:
$R_1$ is $C_1$-$C_6$ alkyl, $C_1$-$C_6$ perfluoroalkyl, $C_3$-$C_8$ cycloalkyl, $C_6$-$C_{14}$ aryl, or arylalkyl;
$R_2$ is $C_1$-$C_6$ alkyl, $C_1$-$C_6$ perfluoroalkyl, $C_3$-$C_8$ cycloalkyl, $C_6$-$C_{14}$ aryl, or arylalkyl;
or $R_1$ and $R_2$ form a $C_5$-$C_8$ carbocyclic ring;
$R_3$, $R_4$ and $R_5$ are, independently, hydrogen, $C_1$-$C_6$ alkyl, $C_3$-$C_8$ cycloalkyl, halogen, hydroxy, $C_6$-$C_{14}$ aryl, $C_1$-$C_3$ perfluoroalkyl, $C_1$-$C_3$ alkoxy, or $C_1$-$C_3$ perfluoroalkoxy;
$R_6$ is hydrogen, $C_1$-$C_6$ alkyl, $C_1$-$C_6$ arylalkyl, $C_1$-$C_6$ alkanoyl, or aroyl;
$R_7$ is hydrogen, $C_1$-$C_6$ alkyl, arylalkyl, or aryl;
n is an integer of 0-6;
A is COOH, or an acid mimic.

In certain preferred embodiments of the present invention, such substituted phenyl indoles of the invention include those compounds of formula 1 wherein $R_2$ is aryl, $R_7$ is hydrogen, n is 0, and A is COOH or tetrazole and $R_1$, $R_3$, $R_4$, $R_5$, and $R_6$ are as described above.

In other preferred embodiments of the present invention, such substituted phenyl indoles of the invention include those compounds of formula 1 wherein $R_1$ is, independently, $C_3$-$C_8$ cycloalkyl, and $R_2$ is, independently, $C_1$-$C_6$ alkyl, $C_1$-$C_6$ perfluoroalkyl, $C_3$-$C_8$ cycloalkyl, $C_6$-$C_{14}$ aryl, or arylalkyl; or $R_1$ is, independently, $C_1$-$C_6$ alkyl, $C_1$-$C_6$ perfluoroalkyl, $C_3$-$C_8$ cycloalkyl, $C_6$-$C_{14}$ aryl, or arylalkyl and $R_2$ is, independently, $C_1$-$C_6$ perfluoroalkyl, or $C_3$-$C_8$ cycloalkyl; or $R_1$ is, independently, $C_1$-$C_6$ perfluoroalkyl, $C_3$-$C_8$ cycloalkyl, or unsubstituted aryl, and $R_2$ is, independently, $C_1$-$C_6$ perfluoroalkyl, $C_3$-$C_8$ cycloalkyl, or unsubstituted aryl; or $R_1$ and $R_2$ form a $C_5$-$C_8$ carbocyclic ring; and $R_3$, $R_4$, $R_5$, $R_6$, $R_7$, n, and A are as described above.

In other preferred embodiments of the present invention, such substituted phenyl indoles of the invention include those compounds of formula 1 wherein $R_1$ is, independently, $C_1$-$C_6$ perfluoroalkyl or $C_3$-$C_8$ cycloalkyl, and $R_2$ is, independently, $C_1$-$C_6$ alkyl, $C_1$-$C_6$ perfluoroalkyl, $C_3$-$C_8$ cycloalkyl, $C_6$-$C_{14}$ aryl, or arylalkyl; or $R_1$ is, independently, $C_1$-$C_6$ alkyl, $C_1$-$C_6$ perfluoroalkyl, $C_3$-$C_8$ cycloalkyl, $C_6$-$C_{14}$ aryl, or arylalkyl and $R_2$ is, independently, $C_1$-$C_6$ perfluoroalkyl or $C_3$-$C_8$ cycloalkyl; or $R_1$ and $R_2$ form a $C_5$-$C_8$ carbocyclic ring; $R_6$ is $C_1$-$C_6$ alkanoyl, or aroyl; and $R_3$, $R_4$, $R_5$, $R_7$, n, and A are as described above.

In yet other preferred embodiments of the present invention, such substituted phenyl indoles of the invention include those compounds of formula 1 wherein $R_1$ is, independently, $C_1$-$C_6$ alkyl, $C_1$-$C_6$ perfluoroalkyl, $C_3$-$C_8$ cycloalkyl, arylalkyl, or aryl and $R_2$ is, independently, $C_1$-$C_6$ perfluoroalkyl, $C_3$-$C_8$ cycloalkyl, or unsubstituted aryl; or $R_1$ and $R_2$ together form a $C_5$-$C_8$ carbocyclic ring; A is an acid mimic; and $R_3$, $R_4$, $R_5$, $R_6$, $R_7$, and n are as described above.

In certain embodiments of the present invention, such substituted phenyl indoles include the following compounds:

Formula 2
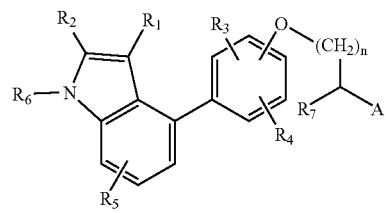

Formula 3
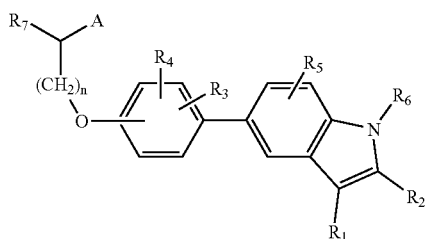

Formula 4
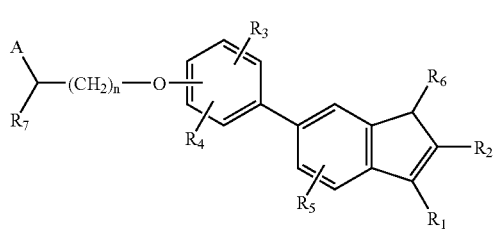

Formula 5
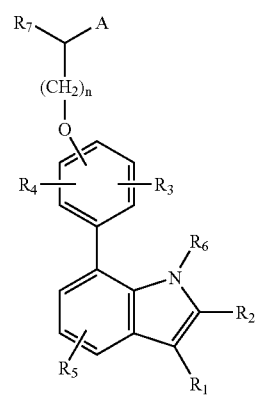

Formula 6
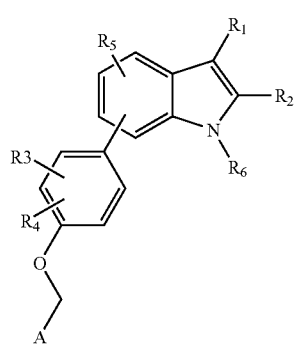

Formula 7
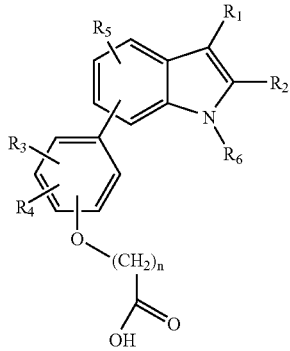

Formula 8
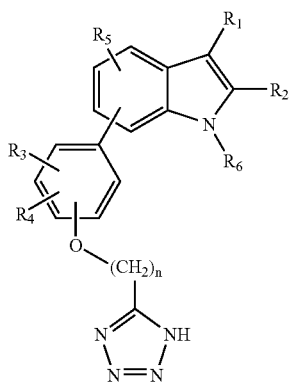

wherein $R_1$, $R_2$, $R_3$, $R_4$, $R_5$, $R_6$, and $R_7$, n, and A are defined as above for Formula 1.

In even other preferred embodiments of the present invention such substituted phenyl indoles of the invention include those of formulas 3, 4 and 5 wherein A is an acid mimic; $R_6$ is $C_1$-$C_6$ alkanoyl, or aroyl; and $R_1$, $R_2$, $R_3$, $R_4$, $R_5$, $R_7$, and n are as described above for Formula 1.

The present invention also provides, inter alia, pharmaceutically acceptable salt or ester forms of compounds of formulas 1-8.

The present invention further provides, inter alia, methods of using substituted phenyl indoles. In one aspect of the present invention, a therapeutically effective amount of one or more substituted phenyl indoles is administered to a subject in order to treat a PAI-1 related disorder, e.g., by inhibiting PAI-1 activity in the subject. PAI-1 activity is associated with a number of diseases and conditions. For example, in one embodiment of the present invention, PAI-1 activity is associated with impairment of the fibrinolytic system. In other embodiments, PAI-1 activity is associated with thrombosis, e.g., venous thrombosis, arterial thrombosis, cerebral thrombosis, and deep vein thrombosis, atrial fibrillation, pulmonary fibrosis, thromboembolic complications of surgery, cardiovascular disease, e.g., myocardial ischemia, atherosclerotic plaque formation, chronic obstructive pulmonary disease, renal fibrosis, polycystic ovary syndrome, Alzheimer's disease, or cancer.

DETAILED DESCRIPTION

A. General Overview

The present invention provides compounds that inhibit PAI-1 activity, processes for preparing such compounds, pharmaceutical compositions containing such compounds, and methods for using such compounds in medical therapies. The compounds have properties that are useful for the treatment, including the prevention and inhibition, of a wide variety of diseases and disorders including those involving the production and/or action of PAI-1. These include disorders resulting from impairment of the fibrinolytic system including, but not limited to, thrombosis, coronary heart disease, renal fibrosis, atherosclerotic plaque formation, pulmonary disease, myocardial ischemia, atrial fibrillation, coagulation syndromes, thromboembolic complications of surgery, peripheral arterial occlusion and pulmonary fibrosis. Other disorders include, but are not limited to, polycystic ovary syndrome, Alzheimer's disease, and cancer.

The terms "alkyl" and "alkylene," as used herein, whether used alone or as part of another group, refer to substituted or unsubstituted aliphatic hydrocarbon chains, the difference being that alkyl groups are monovalent (i.e., terminal) in nature whereas alkylene groups are divalent and typically serve as linkers. Both include, but are not limited to, straight and branched chains containing from 1 to 12 carbon atoms, preferably 1 to 6 carbon atoms, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted. Exemplary substituents include, but are not limited to, hydroxy, $C_1$-$C_6$ alkoxy, oxo (=O), alkanoyl, or aroyl.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain and includes, but is not limited to, straight and branched chains having 2 to 8 carbon atoms and containing at least one double bond. Preferably, the alkenyl moiety has 1 or 2 double bonds. Such alkenyl moieties can exist in the E or Z conformations and the compounds of this invention include both conformations. Specifically included within the definition of "alkenyl" are those aliphatic hydrocarbon chains that are optionally substituted. Exemplary substituents include, but are not limited to, hydroxy, $C_1$-$C_6$ alkoxy, oxo (=O), alkanoyl, or aroyl. Heteroatoms, such as O, S or N—$R_1$, attached to an alkenyl should not be attached to a carbon atom that is bonded to a double bond.

The term "alkynyl", as used herein, whether used alone or as part of another group, refers to a substituted or unsubstituted aliphatic hydrocarbon chain and includes, but is not limited to, straight and branched chains having 2 to 6 carbon atoms and containing at least one triple bond. In certain embodiments, the alkynyl can contain more than one triple bond and, in such cases, the alkynyl group must contain at least three carbon atoms. Specifically included within the definition of "alkynyl" are those aliphatic hydrocarbon chains that are optionally substituted. Exemplary substituents include, but are not limited to, hydroxy, $C_1$-$C_6$ alkoxy, oxo (=O), alkanoyl, or aroyl. Heteroatoms, such as O, S or N—$R_1$, attached to an alkynyl should not be attached to the carbon that is bonded to a triple bond.

The term "cycloalkyl" as used herein, whether alone or as part of another group, refers to a substituted or unsubstituted alicyclic hydrocarbon group having 3 to 8 carbon atoms. Exemplary substituents include, but are not limited to, hydroxy, $C_1$-$C_6$ alkoxy, oxo (=O), alkanoyl, or aroyl.

The term "aryl", as used herein, whether used alone or as part of another group, is defined as a substituted or unsubstituted aromatic hydrocarbon ring group having 6 to 14 carbon atoms, unless explicitly specified otherwise. The "aryl" group can have a single ring or multiple condensed rings. The term "aryl" includes, but is not limited to phenyl, α-naphthyl, β-naphthyl, biphenyl, anthryl, tetrahydronaphthyl, fluorenyl, indanyl, biphenylenyl, and acenaphthenyl. Preferred aryl groups include phenyl, naphthyl, and the like. Specifically included within the definition of "aryl" are those aromatic groups that are optionally substituted. For example, in some embodiments of the present invention, the "aryl" groups are optionally substituted with from 1 to 5 substituents selected from the group consisting of hydrogen, hydroxy, aryl, acyl, $C_1$-$C_6$ alkyl, $C_1$-$C_6$ alkoxy, $C_2$-$C_6$ alkenyl, $C_2$-$C_6$ alkynyl, substituted alkyl, substituted alkoxy, substituted alkenyl, substituted alkynyl, amino, amino substituted by one or two $C_1$-$C_6$ alkyl groups, cyano, halogen, nitro, and trihalomethyl. In some embodiments of the present invention, for example, in some embodiments wherein $R_2$ is phenyl, the aryl groups are optionally substituted with from 1 to 5 substituents selected from the group consisting of hydrogen, hydroxy, aryl, acyl, $C_1$-$C_6$ alkoxy, $C_2$-$C_6$ alkenyl, $C_2$-$C_6$ alkynyl, substituted alkyl, substituted alkoxy, substituted alkenyl, substituted alkynyl, amino, amino substituted by one or two $C_1$-$C_6$ alkyl groups, cyano, halogen, nitro, and trihalomethyl.

As used herein, the term "heteroaryl", whether used alone or as part of another group, is defined as a substituted or unsubstituted aromatic heterocyclic ring system (monocyclic or bicyclic). Heteroaryl groups can have, for example, from about 3 to about 50 carbon atoms (unless explicitly specified otherwise) with from about 4 to about 10 being preferred. In some embodiments, heteroaryl groups are aromatic heterocyclic rings systems having about 4 to about 14 ring atoms including carbon atoms and 1, 2, 3, or 4 heteroatoms selected from oxygen, nitrogen or sulfur. Representative heteroaryl groups are furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S.

The term "alkoxy" as used herein, refers to the group $R_a$—O— wherein $R_a$ is an alkyl group as defined above.

The term "arylalkyl", as used herein, whether used alone or as part of another group, refers to the group —$R_a$-$R_b$, where $R_a$ is an alkyl group as defined above, substituted by $R_b$, an aryl group, as defined above. Examples of arylalkyl moieties include, but are not limited to, benzyl, 1-phenylethyl, 2-phenylethyl, 3-phenylpropyl, 2-phenylpropyl and the like.

The term "perfluoroalkyl", as used herein, whether used alone or as part of another group, refers to a saturated aliphatic hydrocarbon having 1 to 6 carbon atoms (unless explicitly specified otherwise) and two or more fluorine atoms and includes, but is not limited to, straight or branched chains, such as —$CF_3$, —$CH_2CF_3$, —$CF_2CF_3$ and —$CH(CF_3)_2$.

The term "alkanoyl" as used herein, refers to the group R—C(=O)— where R is an alkyl group as defined above.

The term "aroyl" refers to arylcarbonyl groups such as benzoyl groups.

The term "halogen" refers to chlorine, bromine, fluorine, and iodine.

The term "treating" refers to any indicia of success in the treatment or amelioration of an injury, pathology, or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluations. "Treating" or "treatment of a PAI-1 related disorder" includes preventing the onset of symptoms in a subject that may be predisposed to a PAI-1 related disorder but does not yet experience or exhibit symptoms of the disorder (prophylactic treatment), inhibiting the symptoms of the disorder (slowing or arresting its development), providing relief from the symptoms or side-effects of the disorder (including palliative treatment), and relieving the symptoms of the disorder (causing regression). Accordingly, the term "treating" includes the administration of the compounds or agents of the present invention to a subject to prevent or delay, to alleviate, or to arrest or inhibit development of the symptoms or conditions associated with PAI-1 related disorders, e.g., tumor growth associated with cancer. A skilled medical practitioner will know how to use standard methods to determine whether a patient is suffering from a disease associated with enhanced levels and/or activity of PAI-1, e.g., by assaying for PAI-1 levels in blood plasma or tissue of the individual suspected of suffering from a PAI-1 related disease or by examining the patient and determining whether the patient is suffering from a disease known to be associated with elevated PAI-1 levels or activity. Increased PAI-1 levels are indicative of disease. Accordingly, the present invention provides, inter alia, methods of administering a compound of the present invention to a subject and determining levels of PAI-1 in the subject. The level of PAI-1 in the subject can be determined before and/or after administration of the compound.

In healthy individuals, PAI-1 is found at low levels in the plasma (from about 5-26 ng/mL), but it is elevated in many PAI-1 related disorders, including, for example, atherosclerosis (Schneiderman J. et. al, *Proc Natl Acad Sci* 89: 6998-7002, 1992) deep vein thrombosis (Juhan-Vague I, et. al, *Thromb Haemost* 57: 67-72, 1987), and non-insulin dependent diabetes mellitus (Juhan-Vague I, et. al, *Thromb Haemost* 78: 565-660, 1997). PAI-1 stabilizes both arterial and venous thrombi, contributing respectively to coronary arterial occlusion in post-myocardial infarction (Hamsten A, et. al. *Lancet* 2:3-9, 1987), and venous thrombosis following postoperative recovery from orthopedic surgery. (Siemens H J, et. al, *J Clin Anesthesia* 11: 622-629, 1999). Plasma PAI-1 is also elevated, for example, in postmenopausal women, and has been proposed to contribute to the increased incidence of cardiovascular disease in this population (Koh K et. al, *N Engl J Med* 336: 683-690, 1997).

The term "PAI-1 related disorder or disease" refers to any disease or condition that is associated with increased or enhanced expression or activity of PAI-1 or increased or enhanced expression or activity of a gene encoding PAI-1. Examples of such increased activity or expression can include one or more of the following: activity of the protein or expression of the gene encoding the protein is increased above the level of that in normal subjects; activity of the protein or expression of the gene encoding the protein is in an organ, tissue or cell where it is not normally detected in normal subjects (i.e. spatial distribution of the protein or expression of the gene encoding the protein is altered); activity of the protein or expression of the gene encoding the protein is increased when activity of the protein or expression of the gene encoding the protein is present in an organ, tissue or cell for a longer period than in a normal subjects (i.e., duration of activity of the protein or expression of the gene encoding the protein is increased). A normal or healthy subject is a subject not suffering from a PAI-1 related disorder or disease. In some embodiments of the present invention, the PAI-1 related disorder is not associated with hyperglycemia. A PAI-1 related disorder that is not associated with hyperglycemia is one, for example, that is not caused by elevated levels of glucose in the blood.

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" refers to salts and esters that are pharmaceutically acceptable and have the desired pharmacological properties. Such salts include, for example, salts that can be formed where acidic protons present in the compounds are capable of reacting with inorganic or organic bases. Suitable inorganic salts include, for example, those formed with the alkali metals or alkaline earth metals, e.g. sodium and potassium, magnesium, calcium, and aluminum. Suitable organic salts include, for example, those formed with organic bases such as the amine bases, e.g. ethanolamine, diethanolamine, triethanolamine, trimethamine, N methylglucamine, and the like. Pharmaceutically acceptable salts can also include acid addition salts formed from the reaction of basic moieties such as amines in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g. $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention can be present in more than one stereoisomeric form, and the naming of such compounds is intended to include all single stereoisomers and all mixtures (whether racemic or otherwise) of such stereoisomers.

"Inhibitors," "activators," and "modulators" of expression or of activity are used to refer to inhibitory, activating, or modulating molecules, respectively, identified using in vitro and in vivo assays for expression or activity. Inhibitors of the present invention are compositions that, inhibit expression of PAI-1 or bind to, partially or totally block stimulation, decrease, prevent, delay activation, inactivate, desensitize, or down regulate the activity of PAI-1. Samples or assays comprising PAI-1 can be treated with a composition of the present invention and compared to control samples without a composition of the present invention. Control samples (untreated with compositions of the present invention) can be assigned a relative activity value of 100%. In certain embodiments, inhibition of PAI-1 is achieved when the activity value relative to the control is about 80% or less, optionally 50% or 25, 10%, 5% or 1%.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the composition.

A "therapeutically effective amount" or "pharmaceutically effective amount" means the amount that, when administered to a subject, produces effects for which it is administered. For example, a "therapeutically effective amount," when administered to a subject to inhibit PAI-1 activity, is sufficient to inhibit PAI-1 activity. A "therapeutically effective amount," when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compositions of the invention can be administered. In an exemplary embodiment, of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and formulations of the present invention. In some embodiments of the present invention, the subject to be treated with the methods of the present invention does not have hyperglycemia and/or a disease that has been caused by hyperglycemia. Methods of determining whether a subject has hyperglycemia are known in the art and include, for example, performing a glucose test that measures the level of glucose in the blood. Two exemplary tests that can be used to measure the presence of excess levels of glucose in the blood include a test that measures the amount of glucose in the blood after an overnight fast and a test that measures the body's ability to process excess sugar presented after drinking a high glucose test. Typically a subject having a fasting sugar level (sugar level after an overnight fast) of about 64 to about 110 mg/dl does not have hyperglycemia whereas as person having a fasting sugar level of greater than 110 mg/dl has elevated blood sugar levels. A value above about 140 mg/dl on at least two occasions typically signifies that the subject has diabetes.

When any variable occurs more than one time in any constituent or in any formula, its definition in each occurrence is independent of its definition at every other occurrence. Combinations of substituents and/or variables are permissible only if such combinations result in stable compounds.

B. Substituted Phenyl Indoles

The present invention provides novel substituted phenyl indoles. Such compounds are preferably administered to inhibit PAI-1 expression or activity in a subject and, ultimately, to treat disease and conditions associated with increased PAI-1 activity in a subject, e.g., a PAI-1 related disorder.

Substituted phenyl indoles of the present invention comprise compounds of the following formula ("Formula 1")

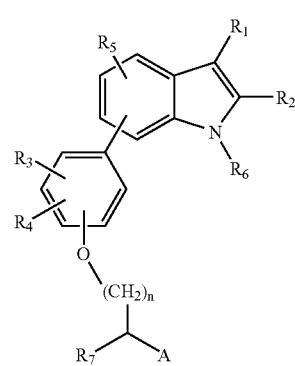

Formula 1 wherein:

$R_1$ is, independently, $C_1$-$C_6$ alkyl, $C_1$-$C_6$ perfluoroalkyl, $C_3$-$C_8$ cycloalkyl, $C_6$-$C_{14}$ aryl, or arylalkyl;

$R_2$ is, independently, $C_1$-$C_6$ alkyl, $C_1$-$C_6$ perfluoroalkyl, $C_3$-$C_8$ cycloalkyl, $C_6$-$C_{14}$ aryl, or arylalkyl;

or $R_1$ and $R_2$ form a $C_5$-$C_8$ carbocyclic ring;

$R_3$, $R_4$ and $R_5$ are, independently, hydrogen, $C_1$-$C_6$ alkyl, $C_3$-$C_8$ cycloalkyl, halogen, hydroxy, $C_6$-$C_{14}$ aryl, $C_1$-$C_3$ perfluoroalkyl, $C_1$-$C_3$ alkoxy, or $C_1$-$C_3$ perfluoroalkoxy;

$R_6$ is hydrogen, $C_1$-$C_6$ alkyl, $C_1$-$C_6$ arylalkyl, $C_1$-$C_6$ alkanoyl, or aroyl;

$R_7$ is hydrogen, $C_1$-$C_6$ alkyl, arylalkyl, or aryl;

n is an integer of 0-6;

A is COOH, or an acid mimic.

Compounds of the present invention also include prodrugs, stereoisomers, or pharmaceutically acceptable salt or ester forms of formula 1.

In certain embodiments of the present invention, such substituted phenyl indoles include the following compounds:

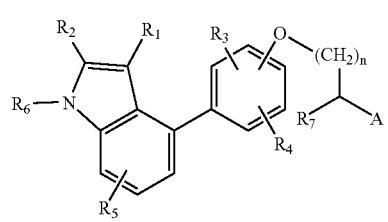

Formula 2

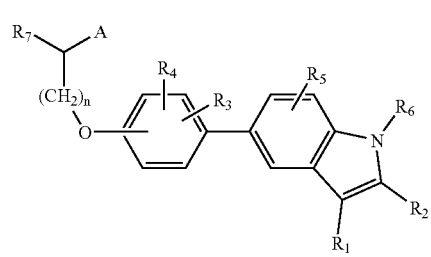

Formula 3

Formula 4

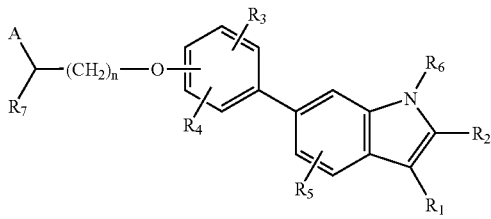

Formula 5

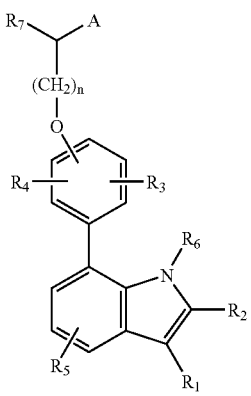

Formula 6

Formula 7

Formula 8

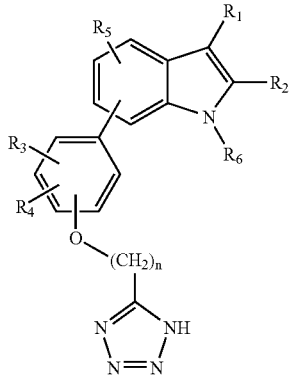

wherein $R_1$, $R_2$, $R_3$, $R_4$, $R_5$, $R^6$, and $R_7$, n, and A are defined as above for Formula 1.

In certain representative embodiments of the present invention, when the substituted phenyl indole is represented by one of formulas 1 to 8, $R_1$ and $R_2$ together form a $C_5$-$C_8$ carbocyclic ring and $R_3$, $R_4$, $R_5$, $R_6$, $R_7$, n, and A are as defined herein for formulas 1 to 8.

In certain representative embodiments of the present invention, when the substituted phenyl indole is represented by one of formulas 1 to 8, either $R_1$ or $R_2$ are $C_3$-$C_8$ cycloalkyl and $R_3$, $R_4$, $R_5$, $R_6$, $R_7$, n, and A are as defined herein for formulas 1 to 8.

In certain representative embodiments of the present invention, when the substituted phenyl indole is represented by one of formulas 1 to 8, either $R_1$ or $R_2$ are $C_1$-$C_6$ perfluoroalkyl and $R_3$, $R_4$, $R_5$, $R_6$, $R_7$, n, and A as defined herein for formulas 1 to 8.

In certain representative embodiments of the present invention, when the substituted phenyl indole is represented by Formula 2 and A is an acid mimic, $R_1$ is, independently, $C_1$-$C_6$ perfluoroalkyl, $C_3$-$C_8$ cycloalkyl, $C_6$-$C_{14}$ aryl or arylalkyl or $R_1$ and $R_2$ together form a $C_5$-$C_8$ carbocyclic ring and $R_3$, $R_4$, $R_5$, $R_6$, $R_7$, n, and A are as defined herein for Formula 2.

In certain representative embodiments of the present invention, when the substituted phenyl indole is represented by Formula 2 and A is an acid mimic, $R_1$ is, independently, hydrogen, $C_1$-$C_6$ perfluoroalkyl, $C_3$-$C_8$ cycloalkyl, or aryl, or $R_1$ and $R_2$ together form a $C_5$-$C_8$ carbocyclic ring and $R_3$, $R_4$, $R_5$, $R_6$, $R_7$, n, and A as defined herein for Formula 2.

In a preferred embodiment of the present invention, when the substituted phenyl indole is represented by one of formulas 1 to 8, $R_1$ is $C_3$-$C_8$ cycloalkyl and $R_2$ is $C_1$-$C_6$ alkyl, $C_1$-$C_6$ perfluoroalkyl, $C_3$-$C_8$ cycloalkyl, $C_6$-$C_{14}$ aryl, or arylalkyl; or $R_1$ is $C_1$-$C_6$ alkyl, $C_1$-$C_6$ perfluoroalkyl, $C_3$-$C_8$ cycloalkyl, $C_6$-$C_{14}$ aryl, or arylalkyl and $R_2$ is $C_1$-$C_6$ perfluoroalkyl or $C_3$-$C_8$ cycloalkyl; or $R_1$ is $C_3$-$C_8$ cycloalkyl, $C_1$-$C_6$ perfluoroalkyl, or unsubstituted aryl and $R_2$ is $C_1$-$C_6$ perfluoroalkyl or $C_3$-$C_8$ cycloalkyl or unsubstituted aryl; or $R_1$ and $R_2$ together form a $C_5$-$C_8$ carbocylic ring, and $R_3$, $R_4$, $R_5$, $R_6$, $R_7$, n, and A are as defined herein for formulas 1 to 8.

In another preferred embodiment of the present invention, when the substituted phenyl indole is represented by one of formulas 1 to 8, $R_2$ is an unsubstituted aryl group or a substituted aryl group. In one aspect, the aryl group is optionally substituted with from 1 to 5 substituents selected from the group consisting of hydroxy, acyl, $C_1$-$C_6$ alkoxy, $C_2$-$C_6$ alkenyl, $C_2$-$C_6$ alkynyl, substituted alkoxy, substituted alkenyl, substituted alkynyl, amino, amino substituted by one or two $C_1$-$C_6$ alkyl groups, cyano, halogen, nitro, and trihalomethyl and $R_1$, $R_3$, $R_4$, $R_5$, $R_6$, $R_7$, n, and A are as defined herein for formulas 1 to 8.

In another preferred embodiment of the present invention, when the substituted phenyl indole is represented by one of Formulas 1 to 5, $R_1$ is, independently, $C_1$-$C_6$ alkyl or benzyl, $R_2$ is, independently, unsubstituted phenyl, or $R_1$ and $R_2$ together are a $C_5$-$C_8$ carbocyclic ring, $R_6$ is $C_1$-$C_6$ alkyl or benzyl, $R_3$, $R_4$, $R_5$ and $R_7$ are hydrogen, n is 1, and A is COOH or tetrazole.

Compounds of the present invention also include prodrugs, stereoisomers, or pharmaceutically acceptable salts or ester forms of formulas 1-8.

Exemplary compounds of the present invention include, but are not limited to, 1-benzyl-3-methyl-2-phenyl-5-[4-(1H-tetrazol-5-ylmethoxy)-phenyl]-1H-indole or a pharmaceutically acceptable salt thereof; [4-(1-benzyl-3-methyl-2-phenyl-1H-indol-5-yl)-phenoxy]-acetic acid or a pharmaceutically acceptable salt thereof; 1,3-dimethyl-2-phenyl-5-[4-(1H-tetrazol-5-ylmethoxy)-phenyl]-1H-indole or a pharmaceutically acceptable salt thereof; 1-benzyl-2,3-dimethyl-5-[4-(1H-tetrazol-5-ylmethoxy)-phenyl]-1H-indole or a pharmaceutically acceptable salt thereof; [4-(1-benzyl-2,3-dimethyl-1H-indol-5-yl)-phenoxy]-acetic acid or a pharmaceutically acceptable salt thereof; 9-benzyl-6-[4-(1H-tetrazol-5-ylmethoxy)-phenyl]-2,3,4,9-tetrahydro-1H-carbazole or a pharmaceutically acceptable salt thereof; 4-(9-benzyl-6,7,8,9-tetrahydro-5H-carbazol-3-yl)-phenoxy]-acetic acid or a pharmaceutically acceptable salt thereof; 9-methyl-6-[4-(1H-tetrazol-5-ylmethoxy)-phenyl]-2,3,4,9-tetrahydro-1H-carbazole or a pharmaceutically acceptable salt thereof; 1,3-dibenzyl-2-methyl-5-[4-(1H-tetrazol-5-ylmethoxy)-phenyl]-1H-indole or a pharmaceutically acceptable salt thereof; [4-(1,3-dibenzyl-2-methyl-1H-indol-5-yl)-phenoxy]-acetic acid or a pharmaceutically acceptable salt thereof; 3-benzyl-1,2-dimethyl-5-[4-(1H-tetrazol-5-ylmethoxy)-phenyl]-1H-indole or a pharmaceutically acceptable salt thereof; 4-(3-benzyl-1,2-dimethyl-1H-indol-5-yl)-phenoxy]-acetic acid or a pharmaceutically acceptable salt thereof; 1-benzyl-3-methyl-2-phenyl-6-[4-(1H-tetrazol-5-ylmethoxy)-phenyl]-1H-indole or a pharmaceutically acceptable salt thereof; [4-(1-benzyl-3-methyl-2-phenyl-1H-indol-6-yl)-phenoxy]-acetic acid or a pharmaceutically acceptable salt thereof; 1-benzyl-3-methyl-2-phenyl-4-[4-(1H-tetrazol-5-ylmethoxy)-phenyl]-1H-indole or a pharmaceutically acceptable salt thereof; [4-(1-benzyl-3-methyl-2-phenyl-1H-indol-4-yl)-phenoxy]-acetic acid or a pharmaceutically acceptable salt thereof; 1,3-dimethyl-2-phenyl-4-[4-(1H-tetrazol-5-ylmethoxy)-phenyl]-1H-indole or a pharmaceutically acceptable salt thereof; [4-(1,3-dimethyl-2-phenyl-1H-indol-4-yl)-phenoxy]-acetic acid or a pharmaceutically acceptable salt thereof; 1-benzyl-3-pentyl-2-phenyl-5-[4-(1H-tetrazol-5-ylmethoxy)-phenyl]-1H-indole or a pharmaceutically acceptable salt thereof; [4-(1-benzyl-3-pentyl-2-phenyl-1H-indol-5-yl)-phenoxy]-acetic acid or a pharmaceutically acceptable salt thereof; 1-methyl-3-pentyl-2-phenyl-5-[4-(1H-tetrazol-5-ylmethoxy)-phenyl]-1H-indole or a pharmaceutically acceptable salt thereof; [4-(1-methyl-3-pentyl-2-phenyl-1H-indol-5-yl)-phenoxy]-acetic acid or a pharmaceutically acceptable salt thereof; 1,3-dibenzyl-2-phenyl-5-[4-(1H-tetrazol-5-ylmethoxy)-phenyl]-1H-indole or a pharmaceutically acceptable salt thereof; [4-(1,3-dibenzyl-2-phenyl-1H-indol-5-yl)-phenoxy]-acetic acid or a pharmaceutically acceptable salt thereof; 3-benzyl-1-methyl-2-phenyl-5-[4-(1H-tetrazol-5-ylmethoxy)-phenyl]-1H-indole or a pharmaceutically acceptable salt thereof; and [4-(3-benzyl-1-methyl-2-phenyl-1H-indol-5-yl)-phenoxy]-acetic acid or a pharmaceutically acceptable salt thereof.

The present invention also relates to compositions comprising at least one compound of formulas 1-8 or a stereoisomer or pharmaceutically acceptable salt thereof, and one or more pharmaceutically acceptable carriers, excipients, or diluents. Such compositions include pharmaceutical compositions for treating or controlling disease states or conditions associated with increased PAI-1 activity. In certain embodiments, the compositions comprise mixtures of one or more compounds of formulas 1-8.

Certain of the compounds of formulas 1-8 contain stereogenic carbon atoms or other chiral elements and thus give rise to stereoisomers, including enantiomers and diastereomers. The present invention includes all of the stereoisomers of substituted phenyl indoles, as well as mixtures of the stereoisomers. Throughout this application, the name of the product, where the absolute configuration of an asymmetric center is not indicated, is intended to embrace the individual stereoisomers as well as mixtures of stereoisomers.

Where an enantiomer is preferred, it can, in some embodiments, be provided substantially free of the corresponding enantiomer. Thus, an enantiomer substantially free of the corresponding enantiomer refers to a compound that is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein. Methods for the preparation of preferred enantiomers are described, for example, in Jacques, et al., *Enantiomers, Racemates and Resolutions* (Wiley Interscience, New York, 1981); Wilen, S. H., et al., Tetrahedron 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972).

Exemplary ester forms of the compounds of this invention include, but are not limited to, straight chain alkyl esters having from 1 to 6 carbon atoms or branched chain alkyl groups containing 1 to 6 carbon atoms, including methyl, ethyl, propyl, butyl, 2-methylpropyl and 1,1-dimethylethyl esters, cycloalkyl esters, alkylaryl esters, benzyl esters, and the like. Other exemplary esters include, but are not limited to, those of the formula —$COOR_{13}$ wherein $R_{13}$ is selected from the formula:

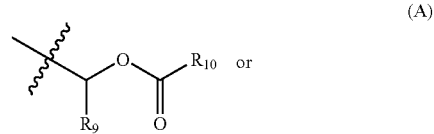

(A)

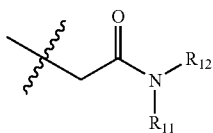
(B)

wherein $R_9$, $R_{10}$, $R_{11}$, and $R_{12}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Acids and acid mimics, according to the invention, are defined as proton or hydrogen donating groups. Exemplary acid mimics or mimetics of the present invention include pharmaceutically useful carboxylic acids and acid mimics or mimetics known in the art, such as those described in R. Silverman, *The Organic Chemistry of Drug Design and Drug Action*, Academic Press (1992) and others. Exemplary acid mimics or mimetics include, but are not limited to the following examples, tetrazole, tetronic acid, acyl tetronic acid, and groups having the formula:

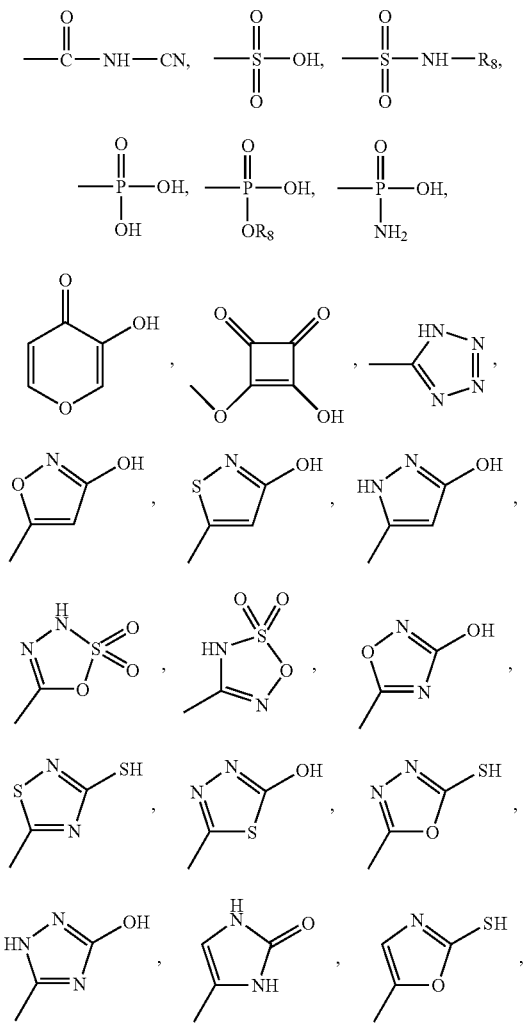

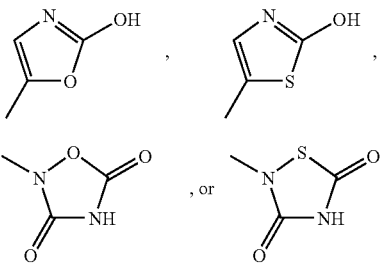

wherein $R^8$ is $C_1$-$C_6$ alkyl, $C_2$-$C_6$ alkenyl, $C_3$-$C_6$ cycloalkyl, —$CH_2$—($C_3$-$C_6$ cycloalkyl), $C_3$-$C_6$ cycloalkenyl, —$CH_2$—($C_3$-$C_6$ cycloalkenyl), optionally substituted aryl or heteroaryl groups or optionally substituted aryl($C_1$-$C_6$)alkyl or heteroaryl($C_1$-$C_6$)alkyl, with the aryl and heteroaryl groups as defined herein. $R_8$ is optionally substituted ($C_1$-$C_6$)alkylaryl or ($C_1$-$C_6$)alkylheteroaryl.

Preferred compounds of the present invention inhibit PAI-1 activity. Accordingly, the compounds can be used for the treatment, including prevention, inhibition; and/or amelioration of PAI-1 related disorders in a subject, including, for example, in the treatment of noninsulin dependent diabetes mellitus, in the treatment of cardiovascular disease, and in the treatment of thrombotic events associated with coronary artery and cerebrovascular disease. Using the methods of the present invention, a skilled medical practitioner will know how to administer substituted phenyl indoles, including those represented by formulas 1-8, to a subject suffering from any of the diseases associated with increased PAI-1 activity or expression, e.g., diabetes or cardiovascular disease, in order to effect treatment for that disease.

In one exemplary embodiment, substituted phenyl indoles are administered to a subject in order to treat disease processes involving thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary thrombosis, cerebral thrombosis, thromboembolic complications of surgery (such as joint or hip replacement), and peripheral arterial occlusion.

Any disease or condition that is associated with increased PAI-1 activity or expression in a subject can be treated using substituted phenyl indoles. Exemplary diseases and conditions include stroke, e.g., stroke associated with or resulting from atrial fibrillation; diseases associated with extracellular matrix accumulation including, but not limited to, renal fibrosis, chronic obstructive pulmonary disease, polycystic ovary syndrome, restenosis, renovascular disease, and organ transplant rejection; diseases associated with neoangiogenesis, including, but not limited to, diabetic retinopathy; Alzheimer's disease, e.g., by increasing or normalizing levels of plasmin concentration in a subject; myelofibrosis with myeloid metaplasia, e.g., by regulating stromal cell hyperplasia and increases in extracellular matrix proteins; diabetic nephropathy and renal dialysis associated with nephropathy; malignancies or cancers, including, but not limited to, leukemia, breast cancer and ovarian cancer; tumors, including, but not limited to, liposarcomas and epithelial tumors; septicemia; obesity; insulin resistance; proliferative diseases, including, but not limited to, psoriasis; conditions associated with abnormal coagulation homeostasis; low grade vascular inflammation; cerebrovascular diseases; hypertension; dementia; osteoporosis; arthritis; respiratory diseases, such as asthma; heart failure; arrhythmia; angina, including, but not limited to, angina pectoris; atherosclerosis and sequelae; kidney failure; multiple sclerosis; osteoporosis; osteopenia; dementia; peripheral vascular disease; peripheral arterial disease; acute vascular syndromes; microvascular diseases including, but not limited to, nephropathy, neuropathy, retinopathy and nephrotic syndrome; hypertension; Type I and 2 diabetes and related diseases; hyperglycemia; hyperinsulinemia; malignant lesions; premalignant lesions; gastrointestinal malignancies; coronary heart disease, including, but not limited to, primary and secondary prevention of myocardial infarction, stable and unstable angina, primary prevention of coronary events, and secondary prevention of cardiovascular events; and inflammatory diseases, including, but not limited to, septic shock and the vascular damage associated with infections.

The compounds of the present invention can also be administered to a subject in combination with a second therapeutic agent, including, but not limited to, prothrombolytic, fibrinolytic, and anticoagulant agents, or in conjunction with other therapies, for example, protease inhibitor-containing highly active antiretroviral therapy (HAART) for the treatment of diseases which originate from fibrinolytic impairment and hyper-coagulability of HIV-1 infected patients. In certain embodiments, the compounds of the present invention can be administered in conjunction with and/or following processes or procedures involving maintaining blood vessel patency, including, but not limited to, vascular surgery, vascular graft and stent patency, organ, tissue and cell implantation and transplantation. The compounds of the present invention can also be used for the treatment of blood and blood products used in dialysis, blood storage in the fluid phase, especially ex vivo platelet aggregation. The compounds of the present invention can also be administered to a subject as a hormone replacement agent or to reduce inflammatory markers or C-reactive protein. The compounds can be administered to improve coagulation homeostasis, to improve endothelial function, or as a topical application for wound healing, e.g., the prevention of scarring. The compounds of the present invention can be administered to a subject in order to reduce the risk of undergoing a myocardial revascularization procedure. The present compounds can also be added to human plasma during the analysis of blood chemistry in hospital settings to determine the fibrinolytic capacity thereof. In certain embodiments, the compounds of the present invention can be used as imaging agents for the identification of metastatic cancers.

C. Synthesis of Representative Substituted Phenyl Indoles

The compounds of the present invention can be prepared by those skilled in the art of organic synthesis employing conventional methods that utilize readily available reagents and starting materials. Representative compounds of the present invention can be prepared using the following synthetic schemes. The skilled practitioner will know how to make use of variants of these process steps, which in themselves are well known in the art. $R_1$, $R_2$, $R_3$, $R_4$, $R_5$, and $R_6$ are defined as above for Formula 1.

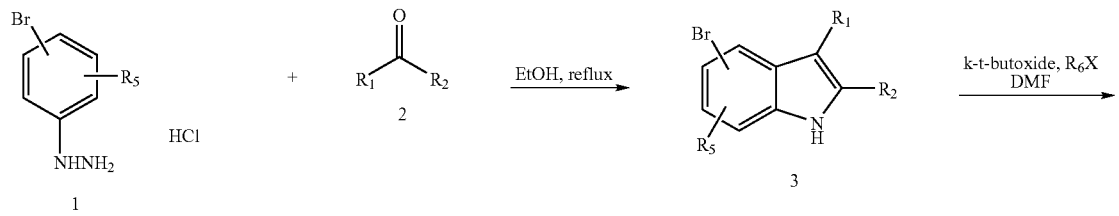

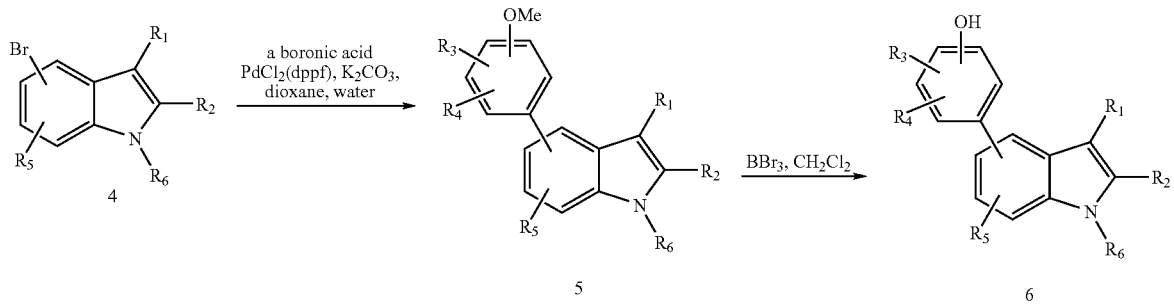

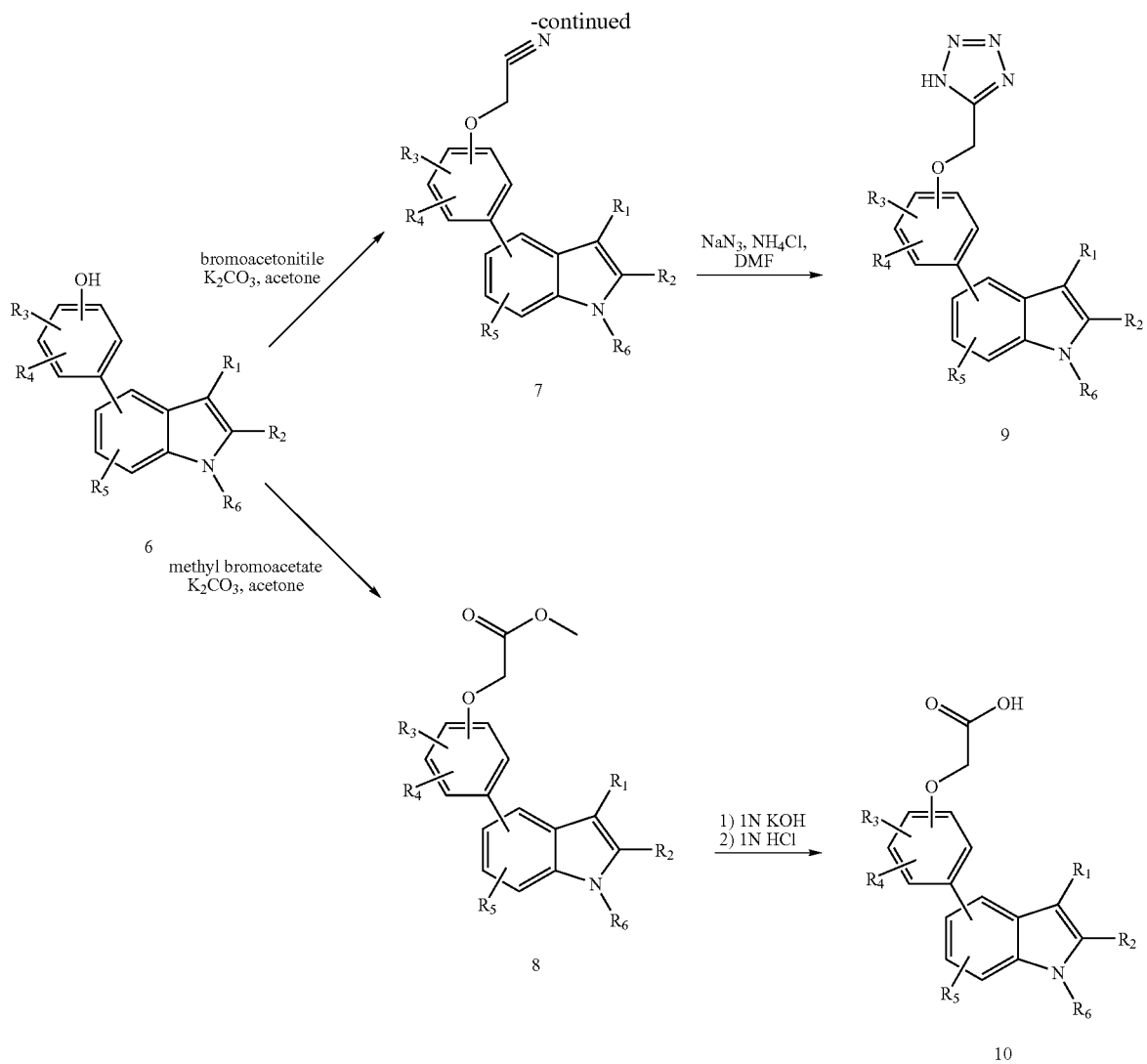

Scheme 1 illustrates the general synthesis used to make representative compounds of the present invention. Formation of the indole ring was done utilizing Fischer-indole chemistry. The appropriate bromophenylhydrazine, hydrochloride (1) was refluxed in EtOH with the required ketone (2) to give the indole intermediate (3). Alkylation of the indole with an alkyl halide ($R_6X$, where X is a halide) affords the bromoindole derivatives 4. Coupling of compounds 4 with the appropriate boronic acid was carried out utilizing standard palladium-catalyzed cross-coupling conditions in a solvent or mixture of solvents such as water, dioxane, and toluene in the presence of a base such as $K_2CO_3$ or $Na_2CO_3$. Treatment of the resulting methoxy phenylindoles (5) with $BBr_3$ in methylene chloride afforded the demethylated phenols (6). The phenol was then alkylated with either bromoacetonitrile or methyl bromoacetate using a base such as potassium carbonate or cesium carbonate in a solvent such as acetone to give the nitrites (7) or esters (8). The nitrites were converted to the tetrazole derivatives (9) using sodium azide and ammonium chloride in DMF at a temperature between 80-100° C. The esters were hydrolyzed to the acetic acid derivatives (10) using a base such as KOH followed by acidification.

D. Substituted Phenyl Indoles as Pharmaceutical Compositions

The present invention provides substituted phenyl indoles as pharmaceuticals. In a preferred embodiment, the substituted phenyl indoles are formulated as pharmaceuticals to treat diseases associated with increased PAI-1 activity, e.g., by inhibiting PAI-1 activity in a subject.

In general, substituted phenyl indoles can be administered as pharmaceutical compositions by any method known in the art for administering therapeutic drugs including oral, buccai, topical, systemic (e.g., transdermal, intranasal, or by suppository), or parenteral (e.g., intramuscular, subcutaneous, or intravenous injection). Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: *Remington's Pharmaceutical Sciences,* 17th ed., Mack Publishing Company, Easton Pa., 1985. Suitable liquid carriers, especially for injectable solutions, include water, aqueous saline solution, aqueous dextrose solution, and glycols. In some embodiments of the present invention, substituted phenyl indoles suitable for use in the practice of this invention will be administered either singly or in combination with at least one other compound of this invention. Substituted phenyl indoles suitable for use in the practice of the present invention can also be administered with at least one other conventional therapeutic agent for the disease being treated.

Aqueous suspensions of the invention contain a substituted phenyl indole in admixture with excipients suitable for the manufacture of aqueous suspensions. Such excipients can include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions can be formulated by suspending a substituted phenyl indole in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of substituted phenyl indoles in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol. The formulations of commends can be presented in unit-dose or multi-dose sealed containers, such as ampules and vials.

Injection solutions and suspensions can be prepared from sterile powders, granules, and tablets of the kind previously described.

Substituted phenyl indoles suitable for use in the practice of this invention can be administered orally. The amount of a compound of the present invention in the composition can vary widely depending on the type of composition, size of a unit dosage, kind of excipients, and other factors well known to those of ordinary skill in the art. In general, the final composition can comprise, for example, from 0.000001 percent by weight (% w) to 10% w of the substituted phenyl indole, preferably 0.00001% w to 1% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethylcellulose; and gums including arabic and tragacanth; as well as proteins such as gelatin and collagen. If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The substituted phenyl indoles of the present invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

The substituted phenyl indoles of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" is intended to include the active ingredient in combination with an encapsulating material as a formulation, with or without other carriers. For example, the compounds of the present invention can also be delivered as microspheres for slow release in the body. In one embodiment, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao, *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months. Cachets can also be used in the delivery of the compounds of the present invention, e.g., anti-atherosclerotic medicaments.

In another embodiment, the compounds of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the substituted phenyl indoles into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

In other cases, the preferred preparation can be a lyophilized powder which may contain, for example, any or all of the following: 1 mM-50 mM histidine, 0.1%-2% sucrose, 2%-7% mannitol, at a pH range of 4.5 to 5.5, that is combined with buffer prior to use.

A pharmaceutical composition of the invention can optionally contain, in addition to a substituted phenyl indole, at least one other therapeutic agent useful in the treatment of a disease or condition associated with increased PAI-1 activity.

The pharmaceutical compositions are generally formulated as sterile, substantially isotonic and in full compliance with all Good Manufacturing Practice (GMP) regulations of the U.S. Food and Drug Administration.

E. Determining Dosage Regimens for Substitued Phenyl Indoles

The present invention provides methods of inhibiting PAI-1 activity in a mammal for the treatment of diseases and conditions associated with increased PAI-1 activity using substituted phenyl indoles. In an exemplary embodiment of the present invention, a skilled practitioner will treat a subject having a disease associated with elevated PAI-1 levels and/or activity with one or more compounds of the present invention.

For treatment purposes, the compositions or compounds disclosed herein can be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol). The pharmaceutical formulations of the present invention can be administered, for example, one or more times daily, 3 times per week, or weekly. In an exemplary embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to alleviate one or more symptoms or detectable conditions associated with increased PAI-1 activity. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response). In alternative embodiments, an "effective amount" or "therapeutically effective dose" of the biologically active agent(s) will simply inhibit or enhance one or more selected biological activity(ies) correlated with a disease or condition, as set forth above, for either therapeutic or diagnostic purposes.

The actual dosage of biologically active agents will of course vary according to factors such as the extent of exposure and particular status of the subject (e.g., the subject's age, size, fitness, extent of symptoms, susceptibility factors, etc), time and route of administration, as well as other drugs or treatments being administered concurrently. Dosage regimens can be adjusted to provide an optimum prophylactic or therapeutic response. By "therapeutically effective dose" herein is meant a dose that produces effects for which it is administered. More specifically, a therapeutically effective dose of the compound(s) of the invention preferably alleviates symptoms, complications, or biochemical indicia of diseases associated with increased PAI-1 activity. The exact dose will depend on the purpose of the treatment, and will be ascertainable by one skilled in the art using known techniques (see, e.g., Lieberman, Pharmaceutical Dosage Forms (Vols. 1-3, 1992); Lloyd, 1999, The Art, Science, and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

In an exemplary embodiment of the present invention, unit dosage forms of the compounds are prepared for standard administration regimens. In this way, the composition can be subdivided readily into smaller doses at the physician's direction. For example, unit dosages can be made up in packeted powders, vials or ampoules and preferably in capsule or tablet form. The active compound present in these unit dosage forms of the composition can be present, for example, in an amount of from about one gram to about fifteen grams or more, for single or multiple daily administration, according to the particular need of the patient. By initiating the treatment regimen with a minimal daily dose of about one gram, the blood levels of PAI-1 and the patient's symptomatic relief analysis can be used to determine whether a larger or smaller dose is indicated. Effective administration of the compounds of this invention can be given at an oral dose of, for example, from about 0.1 mg/kg/day to about 1,000 mg/kg/day. Preferably, administration will be from about 10/mg/kg/day to about 600 mg/kg/day, more preferably from about 25 to about 200 mg/kg/day, and even more preferably from about 50 mg/kg/day to about 100 mg/kg/day.

In certain embodiments, the present invention is directed to prodrugs of compounds of formulas 1-8. The term "prodrug," as used herein, means a compound that is convertible in vivo by metabolic means (e.g. by hydrolysis) to a compound of formulas 1-3. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., *Journal of Drug Delivery Reviews,* 8:1-38(1992), Bundgaard, *J. of Pharmaceutical Sciences,* 77:285 et seq. (1988); and Higuchi and Stella (eds.) Prodrugs as Novel Drug Delivery Systems, American Chemical Society (1975).

F. Kits

After a pharmaceutical comprising a substituted phenyl indole has been formulated in a suitable carrier, it can be placed in an appropriate container and labeled for treatment of a PAI-1 related disorder, e.g., leukemia. Additionally, another pharmaceutical comprising at least one other therapeutic agent useful in the treatment of the PAI-1 related disorder can be placed in the container as well and labeled for treatment of the indicated disease. Alternatively, a single pharmaceutical comprising a substituted phenyl indole and at least one other therapeutic agent useful in the treatment of a PAI-1 related disorder can be placed in an appropriate container and labeled for treatment. For administration of pharmaceuticals comprising substituted phenyl indoles and of pharmaceuticals comprising, in a single pharmaceutical, substituted phenyl indoles and at least one other therapeutic agent useful in the treatment of a PAI-related disorder, such labeling would include, for example, instructions concerning the amount, frequency and method of administration. Similarly, for administration of multiple pharmaceuticals provided in the container, such labeling would include, for example, instructions concerning the amount, frequency and method of administration of each pharmaceutical.

EXAMPLES

Example 1

Screening for PAI-1 inhibition. Test compounds are dissolved in DMSO at a final concentration of 10 mM, then diluted 100× in physiologic buffer. The inhibitory assay is initiated by the addition of the test compound (1-100 µM final concentration, maximum DMSO concentration of 0.2%) in a pH 6.6 buffer containing 140 nM recombinant human plasminogen activator inhibitor-1 (PAI-1; Molecular Innovations, Royal Oak, Mich.). Following a 1 hour incubation at room temperature, 70 nM of recombinant human tissue plasminogen activator (tPA) is added, and the combination of the test compound, PAI-1 and tPA is incubated for an additional 30 minutes. Following the second incubation, Spectrozyme-tPA (American Diagnostica, Greenwich, Conn.), a chromogenic substrate for tPA, is added and absorbance read at 405 nm at 0 and 60 minutes. Relative PAI-1 inhibition is equal to the residual tPA activity in the presence of the test compounds and PAI-1. Control treatments include the complete inhibition of tPA by PAI-1 at the molar ratio employed (2:1), and the absence of any effect of the test compound on tPA alone.

Example 2

Assay for determining the $IC_{50}$ of inhibition of PAI-1. This assay is based upon the non-SDS dissociable interaction between tPA and active PAI-1. Assay plates are initially coated with human tPA (10 µg/ml). Test compounds are dissolved in DMSO at 10 mM, then diluted with physiologic buffer (pH 7.5) to a final concentration of 1-50 µM. The test compounds are incubated with human PAI-1 (50 ng/ml) for 15 minutes at room temperature. The tPA-coated plate is washed with a solution of 0.05% Tween 20 and 0.1% BSA, then the plate is blocked with a solution of 3% BSA. An aliquot of the test compound/PAI-1 solution is then added to the tPA-coated plate, incubated at room temperature for 1 hour, and washed. Active PAI-1 bound to the plate is assessed by adding an aliquot of a 1:1000 dilution of the 33B8 monoclonal antibody against human PAI-1, and incubating the plate at room temperature for 1 hour (Molecular Innovations, Royal Oak, Mich.). The plate is again washed, and a solution of goat anti-mouse IgG-alkaline phosphatase conjugate is added at a 1:50,000 dilution in goat serum. The plate is incubated 30 minutes at room temperature, washed, and a solution of alkaline phosphatase substrate is added. The plate is incubated 45 minutes at room temperature, and color development is determined at OD405 nm. The quantitation of active PAI-1 bound to tPA at varying concentrations of the test compound is used to determine the IC50. Results are analyzed using a logarithmic best-fit equation. The assay sensitivity is 5 ng/ml of human PAI-1 as determined from a standard curve ranging from 0-100 ng/ml.

The compounds of the present invention inhibited Plasminogen Activator Inhibitor-1 as summarized in Table 1.

TABLE 1

| COMPOUNDS | IC$_{50}$ (μM) | % INHIBITION @ 25 μM |
|---|---|---|
| 1-Benzyl-3-methyl-2-phenyl-5-[4-(1H-tetrazol-5-ylmethoxy)-phenyl]-1H-indole | 10.1 | |
| [4-(1-Benzyl-3-methyl-2-phenyl-1H-indol-5-yl)-phenoxy]-acetic acid | 18.1 | |
| 1,3-Dimethyl-2-phenyl-5-[4-(1H-tetrazol-5-ylmethoxy)-phenyl]-1H-indole | 16.5 | |
| 1-Benzyl-2,3-dimethyl-5-[4-(1H-tetrazol-5-ylmethoxy)-phenyl]-1H-indole | 28.2 | |
| [4-(1-Benzyl-2,3-dimethyl-1H-indol-5-yl)-phenoxy]-acetic acid | 51.5 | |
| 9-Benzyl-6-[4-(1H-tetrazol-5-ylmethoxy)-phenyl]-2,3,4,9-tetrahydro-1H-carbazole | 27.5 | |
| [4-(9-Benzyl-6,7,8,9-tetrahydro-5H-carbazol-3-yl)-phenoxy]-acetic acid | 35.6 | |
| 9-Methyl-6-[4-(1H-tetrazol-5-ylmethoxy)-phenyl]-2,3,4,9-tetrahydro-1H-carbazole | 6.1 | |
| 1,3-Dibenzyl-2-methyl-5-[4-(1H-tetrazol-5-ylmethoxy)-phenyl]-1H-indole | 47.7 | |
| [4-(1,3-Dibenzyl-2-methyl-1H-indol-5-yl)-phenoxy]-acetic acid | 25.3 | |
| 3-Benzyl-1,2-dimethyl-5-[4-(1H-tetrazol-5-ylmethoxy)-phenyl]-1H-indole | 43.9 | |
| [4-(3-Benzyl-1,2-dimethyl-1H-indol-5-yl)-phenoxy]-acetic acid | 38.0 | |
| 1-Benzyl-3-methyl-2-phenyl-6-[4-(1H-tetrazol-5-ylmethoxy)-phenyl]-1H-indole | 36.9 | |
| [4-(1-Benzyl-3-methyl-2-phenyl-1H-indol-6-yl)-phenoxy]-acetic acid | — | 27 |
| 1-Benzyl-3-methyl-2-phenyl-4-[4-(1H-tetrazol-5-ylmethoxy)-phenyl]-1H-indole | 25.7 | |
| [4-(1-Benzyl-3-methyl-2-phenyl-1H-indol-4-yl)-phenoxy]-acetic acid | 23.1 | |
| 1,3-Dimethyl-2-phenyl-4-[4-(1H-tetrazol-5-ylmethoxy)-phenyl]-1H-indole | 32.8 | |
| [4-(1,3-Dimethyl-2-phenyl-1H-indol-4-yl)-phenoxy]-acetic acid | 33.9 | |
| 1-Benzyl-3-pentyl-2-phenyl-5-[4-(1H-tetrazol-5-ylmethoxy)-phenyl]-1H-indole | 16.3 | |
| [4-(1-Benzyl-3-pentyl-2-phenyl-1H-indol-5-yl)-phenoxy]-acetic acid | 15.4 | |
| 1-Methyl-3-pentyl-2-phenyl-5-[4-(1H-tetrazol-5-ylmethoxy)-phenyl]-1H-indole | 36.4 | |
| [4-(1-Methyl-3-pentyl-2-phenyl-1H-indol-5-yl)-phenoxy]-acetic acid | — | 68 |
| 1,3-Dibenzyl-2-phenyl-5-[4-(1H-tetrazol-5-ylmethoxy)-phenyl]-1H-indole | — | 51 |
| [4-(1,3-Dibenzyl-2-phenyl-1H-indol-5-yl)-phenoxy]-acetic acid | 12.1 | |
| 3-Benzyl-1-methyl-2-phenyl-5-[4-(1H-tetrazol-5-ylmethoxy)-phenyl]-1H-indole | — | 56 |
| [4-(3-Benzyl-1-methyl-2-phenyl-1H-indol-5-yl)-phenoxy]-acetic acid | — | 48 |

Example 3

Synthesis of 1-Benzyl-3-methyl-2-phenyl-5-[4-(1H-tetrazol-5-ylmethoxy)-phenyl]-1H-indole Step 1: Synthesis of 5-Bromo-3-methyl-2-phenyl-1H-indole. A mixture of 4-bromophenylhydrazine, hydrochloride (4.928 g, 22.05 mmol) and propriophenone (2.818 g, 21 mmol) in EtOH (60 ml) was refluxed under $N_2$. After 18 hours, the reaction mixture was cooled and concentrated. The residue was partitioned between EtOAc (150 ml) and 1N HCl (30 ml). The layers were shaken, separated, and the organic layer washed with 1N HCl (2×20 ml), water (2×20 ml) and brine (2×20 ml), dried over $Na_2SO_4$, filtered, concentrated, and dried to give a solid (6.006 g). The solid was recrystallized from hexane to give the desired product (4.10 g, 14.33 mmol, 65%) as an off-white solid, mp 138-140° C. $^1$H NMR (DMSO-d$_6$) δ 2.37 (s, 3H), 7.18-7.20 (m, 1H), 7.30 (d, J=8.4 Hz, 1H), 7.37 (t, J=7.0 Hz, 1H), 7.51 (t, J=7.6 Hz, 2H), 7.66 (d, J=8.1 Hz, 2H), 7.70 (s, 1H), 11.36 (s, 1H); [ESI(−)], m/z 284/286 (M−H)$^−$.

Step 2: Synthesis of 1-Benzyl-5-bromo-3-methyl-2-phenyl-1H-indole. To a solution of 5-bromo-3-methyl-2-phenyl-1H-indole (1.717 g, 6 mmol) in DMF (20 ml) at 0° C. under $N_2$ was added k-t-butoxide (0.707 g, 6.3 mmol). The reaction mixture was stirred for 30 minutes followed by the addition of benzyl bromide (1.081 g, 6.3 mmol). After 3 hours, the reaction mixture was concentrated to a residue and partitioned between EtOAc (150 ml) and 1N HCl (20 ml). The layers were shaken, separated, and the organic layer washed with 1N HCl (2×20 ml) and brine (2×20 ml), dried over $Na_2SO_4$, filtered, concentrated, and dried to give a solid (2.273 g). The solid was purified by flash column chromatography (silica), eluting with hexane, to give the desired product (1.917 g, 5.094 mmol, 85%) as a white solid, mp 113-116° C.

$^1$H NMR (DMSO-d$_6$) δ 2.19 (s, 3H), 5.30 (s, 2H), 6.79 (d, J=6.9 Hz, 2H), 7.13-7.20 (m, 3H), 7.22 (dd, J=1.8, 8.6 Hz, 1H), 7.33 (d, J=8.7 Hz, 1H), 7.37-7.39 (m, 2H), 7.42-7.45 (m, 1H), 7.48 (t, J=6.9 Hz, 2H), 7.75 (d, J=1.8 Hz, 1H); [EI], m/z 375/377 (M)$^+$.

Step 3: Synthesis of 1-Benzyl-5-(4-methoxy-phenyl)-3-methyl-2-phenyl-1H-indole. To a solution of 1-benzyl-5-bromo-3-methyl-2-phenyl-1H-indole (1.907 g, 5.068 mmol) in dioxane (51 ml) was added aqueous 2M $K_2CO_3$ (5.1 ml) followed by 4-methoxyphenylboronic acid (0.924 g, 6.082 mmol) and [1,1′-bis(diphenylphosphino)ferrocene]dichloropalladium (II) complex with dichloromethane (1:1) (0.083 g, 0.101 mmol). The mixture was stirred at RT for 0.75 hours, then warmed to ~90° C. After heating for 18 hours, the reaction mixture was cooled and concentrated. The residue was partitioned between EtOAc (120 ml) and 1N HCl (30 ml). The layers were shaken, separated, and the organic layer washed with 1N HCl (2×20 ml) and brine (2×20 ml), dried over $Na_2SO_4$, filtered, concentrated, and dried to give a black residue (2.444 g). The residue was purified by flash column chromatography (silica), eluting with hexane, 0.5% and 1% EOAc/hexane, to give the product (1.223 g, 3.031 mmol, 60%) as an off-white solid, mp 117-122° C. $^1$H NMR (DMSO-d$_6$) δ 2.26 (s, 3H), 3.79 (s, 3H), 5.32 (s, 2H), 6.85 (d, J=7.3 Hz, 2H), 7.00 (d, J=8.7 Hz, 2H), 7.15 (t, J=7.0 Hz, 1H), 7.20 (t, J=6.7 Hz, 2H), 7.35-7.44 (m, 5H), 7.49 (t, J=7.0 Hz, 2H), 7.62 (d, J=8.7 Hz, 2H), 7.75 (s, 1H); [ESI(+)], m/z 404 (M+H)$^+$.

Step 4: Synthesis of 4-(1-Benzyl-3-methyl-2-phenyl-1H-indol-5-yl)-phenol. To a solution of 1-benzyl-5-(4-methoxyphenyl)-3-methyl-2-phenyl-1H-indole (1.223 g, 3.031 mmol) in $CH_2Cl_2$ (15 ml) under $N_2$ at −78° C. was added BBr$_3$ (3.6 ml of a 1M solution in CH$_2$Cl$_2$). After the addition of BBr$_3$, the reaction was warmed to 0° C., stirred for 1 hour, then warmed to RT. After 4 hours from the time of the addition of BBr$_3$, the reaction was quenched with water (10 ml), stirred ten minutes, then concentrated. The residue was partitioned between EtOAc (90 ml) and water (20 ml). The layers were shaken, separated, and the organic layer washed with water (2×15 ml) and brine (2×20 ml), dried over Na$_2$SO$_4$, filtered, and concentrated to give a brown foam (1.196 g). The foam was purified by flash chromatography (silica), eluting with 10% EtOAc/hexane, to give the desired product (0.835 g, 2.144 mmol, 71%) as a white solid, dec. 124-129° C. $^1$H NMR (DMSO-d$_6$) δ 2.25 (s, 3H), 5.31 (s, 2H), 6.82-6.85 (m, 4H), 7.14 (t, J=7.0 Hz, 1H), 7.19 (t, J=6.9 Hz, 2H), 7.31-7.36 (m, 2H), 7.39-7.44 (m, 3H), 7.47-7.50 (m, 4H), 7.70 (s, 1H), 9.36 (s, 1H); IR (solid) 3550, 3470, 3030, 1605, 1520, 1470, 1450, 1360, and 1170 cm$^{-1}$; [ESI(+)], m/z 390 (M+H)$^+$; Anal. Calcd. for C$_{28}$H$_{23}$NO: C, 86.34; H, 5.95; N, 3.60; Found: C, 85.87; H, 6.10; N, 3.45.

Step 5: Synthesis of [4-(1-Benzyl-3-methyl-2-phenyl-1H-indol-5-yl)-phenoxy]-acetonitrile. To a stirred solution of 4-(1-benzyl-3-methyl-2-phenyl-1H-indol-5-yl)-phenol (0.342 g, 0.878 mmol) in acetone (10 ml) under N$_2$ was added K$_2$CO$_3$ (0.146 g, 1.054 mmol) and bromoacetonitrile (0.126 g, 1.054 mmol). After 20 hours, the reaction mixture was concentrated and the residue partitioned between EtOAc (100 ml) and water (20 ml). The layers were shaken, separated, and the organic layer washed with water (2×20 ml) and brine (2×20 ml), dried over Na$_2$SO$_4$, filtered and concentrated to give a solid (0.366 g). The solid was purified by flash chromatography (silica), eluting with 8% EtOAc/hexane, followed by recrystallization from MeOH to give the desired product (0.292 g, 0.681 mmol, 78%) as a white solid, mp 139.5-140.5° C. $^1$H NMR (DMSO-d$_6$) δ 2.27 (s, 3H), 5.20 (s, 2H), 5.33 (s, 2H), 6.85 (d, J=7.3 Hz, 2H), 7.13-7.16 (m, 3H), 7.20 (t, J=6.9 Hz, 2H), 7.39-7.44 (m, 5H), 7.49 (t, J=7.0 Hz, 2H), 7.70 (d, J=8.6 Hz, 2H), 7.80 (s, 1H); [ESI(+)], m/z 429 (M+H)$^+$.

Step 6: Synthesis of 1-Benzyl-3-methyl-2-phenyl-5-[4-(1H-tetrazol-5-ylmethoxy)-phenyl]-1H-indole. To a stirred solution of [4-(1-benzyl-3-methyl-2-phenyl-1H-indol-5-yl)-phenoxy]-acetonitrile (0.276 g, 0.644 mmol) in DMF (5 ml) under N$_2$ was added NaN$_3$ (0.209 g, 3.220 mmol) and NH$_4$Cl (0.172 g, 3.220 mmol). The mixture was heated to ~100° C. for 3 hours, then cooled, and concentrated. The residue was partitioned between EtOAc (100 ml) and 1N HCl (25 ml). The layers were shaken, separated, and the organic layer washed with 1N HCl (2×20 ml), water (3×20 ml) and brine (2×20 ml), dried over Na$_2$SO$_4$, filtered and concentrated to give a solid (0.297 g). The solid was recrystallized from MeOH to give the desired product (0.229 g, 0.486 mmol, 75%), as a white solid, dec. 202-205° C. $^1$H NMR (DMSO-d$_6$) δ 2.26 (s, 3H), 5.32 (s, 2H), 5.52 (s, 2H), 6.85 (d, J=7.3 Hz, 2H), 7.12-7.16 (m, 3H), 7.19 (t, J=7.0 Hz, 2H), 7.38-7.44 (m, 5H), 7.49 (t, J=7.0 Hz, 2H), 7.65 (d, J=8.7 Hz, 2H), 7.77 (s, 1H), 16.80 (broad s, 1H); IR (solid) 3030, 2860, 1605, 1570, 1520, 1470, 1260, and 1220 cm$^{-1}$; [ESI(−)], m/z 470 (M−H)$^-$; Anal. Calcd. for C$_{30}$H$_{25}$N$_5$O: C, 76.41; H, 5.34; N, 14.85; Found: C, 76.26; H, 5.46; N, 14.87.

Example 4

Synthesis of [4-(1-Benzyl-3-methyl-2-phenyl-1H-indol-5-yl)-phenoxy]-acetic Acid

Step 1: Synthesis of [4-(1-Benzyl-3-methyl-2-phenyl-1H-indol-5-yl)-phenoxy]-acetic acid methyl ester. To a stirred solution of 4-(1-benzyl-3-methyl-2-phenyl-1H-indol-5-yl)-phenol (0.345 g, 0.886 mmol) in acetone (10 ml) under N$_2$ was added K$_2$CO$_3$ (0.147 g, 1.063 mmol) and methyl bromoacetate (0.163 g, 1.063 mmol). After 20 hours, additional K$_2$CO$_3$ (0.147 g, 1.063 mmol) and methyl bromoacetate (0.163 g, 1.063 mmol) were added. After stirring for an additional 66 hours, the reaction mixture was concentrated and the residue partitioned between EtOAc (150 ml) and water (20 ml). The layers were shaken, separated, and the organic layer was washed with water (2×20 ml) and brine (2×20 ml), dried over Na$_2$SO$_4$, filtered, concentrated, and dried to give a solid (0.433 g). The solid was recrystallized from MeCN to give the desired product (0.335 g, 0.726 mmol, 82%) as a white solid, mp 167-170° C. $^1$H NMR (DMSO-d$_6$) δ 2.26 (s, 3H), 3.71 (s, 3H), 4.83 (s, 2H), 5.32 (s, 2H), 6.85 (d, J=7.2 Hz, 2H), 7.00 (d, J=8.9 Hz, 2H), 7.15 (t, J=7.0 Hz, 1H), 7.19 (t, J=6.9 Hz, 2H), 7.35-7.44 (m, 5H), 7.49 (t, J=7.0 Hz, 2H), 7.61 (d, J=8.9 Hz, 2H), 7.76 (s, 1H); [ESI(+)], m/z 462 (M+H)$^+$.

Step 2: Synthesis of [4-(1-Benzyl-3-methyl-2-phenyl-1H-indol-5-yl)-phenoxy]-acetic acid. To a stirred solution of [4-(1-benzyl-3-methyl-2-phenyl-1H-indol-5-yl)-phenoxy]-acetic acid methyl ester (0.330 g, 0.715 mmol) in THF (12 ml) and MeOH (8 ml) was added 1N KOH (1.4 ml). After 18 hours, the reaction mixture was concentrated and the residue diluted with water (20 ml) and acidified with 2N HCl (1.4 ml). The mixture was extracted with EtOAc (1×90 ml) and the extract washed with 1N HCl (2×20 ml), water (3×20 ml), brine (2×20 ml), dried over Na$_2$SO$_4$, filtered, concentrated, and dried to give a solid (0.300 g). The solid was recrystallized from MeOH to give the desired product (0.251 g, 0.561 mmol, 78%) as a white solid, mp 173.5-175° C. $^1$H NMR (DMSO-d$_6$) δ 2.26 (s, 3H), 4.69 (s, 2H), 5.32 (s, 2H), 6.85 (d, J=7.3 Hz, 2H), 6.98 (d, J=8.7 Hz, 2H), 7.14 (t, J=7.0 Hz, 1H), 7.19 (t, J=7.0 Hz, 2H), 7.35-7.44 (m, 5H), 7.49 (t, J=7.2 Hz, 2H), 7.61 (d, J=8.6 Hz, 2H), 7.75 (s, 1H) 13.0 (broad s, 1H); IR (solid) 3030, 2905, 1740, 1520, 1480, 1440, 1230, and 1200 cm$^{-1}$; [ESI(−)], m/z 446 (M−H)$^-$; Anal. Calcd. for C$_{30}$H$_{25}$NO$_3$: C, 80.51; H, 5.63; N, 3.13; Found: C, 80.16; H, 5.73; N, 3.21.

Example 5

Synthesis of 1,3-Dimethyl-2-phenyl-5-[4-(1H-tetrazol-5-ylmethoxy)-phenyl]-1H-indole Step 1: Synthesis of 5-Bromo-1,3-dimethyl-2-phenyl-1H-indole. The desired product was prepared using a procedure similar to step 2 of example 3. Thus, 5-bromo-3-methyl-2-phenyl-1H-indole (1.413 g, 4.938 mmol) was reacted with k-t-butoxide (0.582 g, 5.185 mmol) and methyl iodide (0.736 g, 5.185 mmol) in DMF (15 ml) to give the desired product (1.364 g, 4.544 mmol, 92%) as an off-white solid, mp 77.5-80° C. $^1$H NMR (DMSO-d$_6$) δ 2.17 (s, 3H), 3.58 (s, 3H), 7.27 (dd, J=1.8, 8.6 Hz, 1H), 7.42-7.48 (m, 4H), 7.54 (t, J=8.1 Hz, 2H), 7.71 (d, J=1.8 Hz, 1H); [EI], m/z 299/301 (M)$^+$.

Step 2: Synthesis of 5-(4-Methoxy-phenyl)-1,3-dimethyl-2-phenyl-1H-indole. The desired product was prepared using a procedure similar to step 3 of example 3. Thus, 5-bromo-1,3-dimethyl-2-phenyl-1H-indole (1.358 g, 4.524 mmol) was reacted with aqueous 2M K$_2$CO$_3$ (4.5 ml), 4-methoxyphenylboronic acid (0.825 g, 5.429 mmol) and [1,1'-bis(diphenylphosphino)ferrocene]dichloropalladium (II) complex with dichloromethane (1:1) (0.074 g, 0.090 mmol) in dioxane (46 ml) to give the desired product (0.563 g, 1.719 mmol, 38%) as a white solid, mp 156-159° C. $^1$H NMR (DMSO-d$_6$) δ 2.25 (s, 3H), 3.61 (s, 3H), 3.79 (s, 3H), 7.01 (d, J=8.7 Hz, 2H), 7.43-7.50 (m, 5H), 7.55 (t, J=7.8 Hz, 2H), 7.64 (d, J=8.7 Hz, 2H), 7.73 (s, 1H); [ESI(+)], m/z 328 (M+H)+.

Step 3: Synthesis of 4-(1,3-Dimethyl-2-phenyl-1H-indol-5-yl)-phenol. The desired product was prepared using a procedure similar to step 4 of example 3. Thus, 5-(4-methoxy-phenyl)-1,3-dimethyl-2-phenyl-1H-indole (0.560 g, 1.710 mmol) was reacted with BBr$_3$ (2.1 ml of a 1M solution in CH$_2$Cl$_2$) to give the desired product (0.484 g, 1.544 mmol, 90%) as a white solid, mp 148-150° C. $^1$H NMR (DMSO-d$_6$) δ 2.24 (s, 3H), 3.60 (s, 3H), 6.84 (d, J=8.6 Hz, 2H), 7.40 (dd, J=1.4, 8.4 Hz, 1H), 7.44-7.47 (m, 4H), 7.50-7.56 (m, 4H), 7.68 (s, 1H), 9.37 (s, 1H); IR (solid) 3350, 3050, 1590, 1520, 1460, and 1230 cm$^{-1}$; [ESI(+)], m/z 314 (M+H)+; Anal. Calcd. for C$_{22}$H$_{19}$NO: C, 84.31; H, 6.11; N, 4.47; Found: C, 84.21; H, 6.37; N, 4.38.

Step 4: Synthesis of [4-(1,3-Dimethyl-2-phenyl-1H-indol-5-yl)-phenoxy]-acetonitrile. The desired product was prepared using a procedure similar to step 5 of example 3. Thus, 4-(1,3-dimethyl-2-phenyl-1H-indol-5-yl)-phenol (0.353 g, 1.126 mmol) was reacted with K$_2$CO$_3$ (0.189 g, 1.352 mmol) and bromoacetonitrile (0.162 g, 1.352 mmol) in acetone (15 ml) to give the desired product (0.362 g, 1.027 mmol, 91%) as a white solid, mp 177-179° C. $^1$H NMR (DMSO-d$_6$) δ 2.25 (s, 3H), 3.61 (s, 3H), 5.21 (s, 2H), 7.15 (d, J=8.7 Hz, 2H), 7.45-7.52 (m, 5H), 7.55 (t, J=7.5 Hz, 2H), 7.72 (d, J=8.9 Hz, 2H), 7.78 (s, 1H); [EI], m/z 352 (M)+.

Step 5: Synthesis of 1,3-Dimethyl-2-phenyl-5-[4-(1H-tetrazol-5-ylmethoxy)-phenyl]-1H-indole. The desired product was prepared using a procedure similar to step 6 of example 3. Thus, [4-(1,3-dimethyl-2-phenyl-1H-indol-5-yl)-phenoxy]-acetonitrile (0.355 g, 1.007 mmol) was reacted with NaN$_3$ (0.327 g, 5.036 mmol) and NH$_4$Cl (0.269 g, 5.036 mmol) in DMF (5 ml) to give the desired product (0.302 g, 0.764 mmol, 76%) as a white solid, dec. 261-262° C. $^1$H NMR (DMSO-d$_6$) δ 2.25 (s, 3H), 3.61 (s, 3H), 5.52 (s, 2H), 7.14 (d, J=8.6 Hz, 2H), 7.45-7.51 (m, 5H), 7.55 (t, J=7.6 Hz, 2H), 7.67 (d, J=8.6 Hz, 2H), 7.75 (s, 1H), 16.80 (broad s, 1H); IR (solid) 3040, 2860, 2620, 1580, 1520, 1480, and 1230 cm$^{-1}$; [ESI(+)], m/z 396 (M+H)+; Anal. Calcd. for C$_{24}$H$_{21}$N$_5$O: C, 72.89; H, 5.35; N, 17.71; Found: C, 72.84; H, 5.33; N, 17.80.

Example 6

Synthesis of 1-Benzyl-2,3-dimethyl-5-[4-(1H-tetrazol-5-ylmethoxy)-phenyl]-1H-indole Step 1: Synthesis of 5-Bromo-2,3-dimethyl-1H-indole. The desired product was prepared using a procedure similar to step 1 of example 3. Thus, 4-bromophenylhydrazine, hydrochloride (4.694 g, 21 mmol) was reacted with 2-butanone (1.442 g, 20 mmol) in ethanol (60 ml) to give the product (3.586 g, 16.002 mmol, 76%) as a tan solid, mp 135-137° C. $^1$H NMR (DMSO-d$_6$) δ 2.11 (s, 3H), 2.29 (s, 3H), 7.05 (dd, J=1.8, 8.4 Hz, 1H), 7.16 (d, J=8.6 Hz, 1H), 7.49 (d, J=1.5 Hz, 1H), 10.85 (s, 1H); [ESI(-)], m/z 222/224 (M−H)−.

Step 2: Synthesis of 1-Benzyl-5-bromo-2,3-dimethyl-1H-indole. The desired product was prepared using a procedure similar to step 2 of example 3. Thus, 5-bromo-2,3-dimethyl-1H-indole (1.793 g, 8 mmol) was reacted with k-t-butoxide (0.943 g, 8.4 mmol) and benzyl bromide (1.442 g, 8.4 mmol) in DMF (20 ml) to give the product (1.872 g, 5.958 mmol, 74%) as a pink solid. $^1$H NMR (DMSO-d$_6$) δ 2.18 (s, 3H), 2.26 (s, 3H), 5.38 (s, 21), 6.94 (d, J=7.3 Hz, 2H), 7.12 (dd, J=1.8, 8.6 Hz, 1H), 7.20 (t, J=7.2 Hz, 1H), 7.27 (t, J=7.2 Hz, 2H), 7.32 (d, J=8.7 Hz, 1H), 7.59 (d, J=1.8 Hz, 1H); [EI], m/z 313/315 (M)+.

Step 3: Synthesis of 1-Benzyl-5-(4-methoxy-phenyl)-2,3-dimethyl-1H-indole. The desired product was prepared using a procedure similar to step 3 of example 3. Thus, 1-benzyl-5-bromo-2,3-dimethyl-1H-indole (1.872 g, 5.958 mmol) was reacted with aqueous 2M K$_2$CO$_3$ (6.0 ml), 4-methoxyphenyl-boronic acid (1.087 g, 7.150 mmol) and [1,1'-bis(diphenylphosphino)ferrocene]dichloropalladium (II) complex with dichloromethane (1:1) (0.097 g, 0.119 mmol) in dioxane (60 ml) to give the product (0.925 g, 2.709 mmol, 45%) as a brown oil. $^1$H NMR (DMSO-d$_6$) δ 2.24 (s, 3H), 2.28 (s, 3H), 3.78 (s, 3H), 5.39 (s, 2H), 6.97-6.99 (m, 4H), 7.20 (t, J=7.2 Hz, 1H), 7.25-7.29 (m, 3H), 7.37 (d, J=8.4 Hz, 1H), 7.59 (d, J=8.7 Hz, 2H), 7.61 (s, 1H); [ESI(+)], m/z 342 (M+H)+.

Step 4: Synthesis of 4-(1-Benzyl-2,3-dimethyl-1H-indol-5-yl)-phenol. The desired product was prepared using a procedure similar to step 4 of example 3. Thus, 1-benzyl-5-(4-methoxy-phenyl)-2,3-dimethyl-1H-indole (0.925 g, 2.709 mmol) was reacted with BBr$_3$ (3.3 ml of a 1M solution in CH$_2$Cl$_2$) to give the product (0.608 g, 1.857 mmol, 69%) as a brown glass. $^1$H NMR (DMSO-d$_6$) δ 2.23 (s, 3H), 2.27 (s, 3H), 5.38 (s, 2H), 6.81 (d, J=8.4 Hz, 2H), 6.98 (d, J=7.5 Hz, 2H), 7.19-7.23 (m, 2H), 7.27 (t, J=7.3 Hz, 2H), 7.34 (d, J=8.6 Hz, 1H), 7.46 (d, J=8.4 Hz, 2H), 7.57 (s, 1H), 9.32 (s, 1H); [ESI(+)], m/z 328 (M+H)+.

Step 5: Synthesis of [4-(1-Benzyl-2,3-dimethyl-1H-indol-5-yl)-phenoxy]-acetonitrile. The desired product was prepared using a procedure similar to step 5 of example 3. Thus, 4-(1-benzyl-2,3-dimethyl-1H-indol-5-yl)-phenol (0.300 g, 0.916 mmol) was reacted with K$_2$CO$_3$ (0.152 g, 1.099 mmol) and bromoacetonitrile (0.132 g, 1.099 mmol) in acetone (10 ml) to give the product (0.207 g, 0.565 mmol, 62%) as a pale-blue solid, mp 167-169° C. $^1$H NMR (DMSO-d$_6$) δ 2.25 (s, 3H), 2.28 (s, 3H), 5.19 (s, 2H), 5.39 (s, 2H), 6.98 (d, J=7.5 Hz, 2H), 7.12 (d, J=8.6 Hz, 2H), 7.21 (t, J=7.2 Hz, 1H), 7.26-7.30 (m, 3H), 7.39 (d, J=8.4 Hz, 1H), 7.65-7.67 (m, 3H); [ESI(+)], m/z 367 (M+H)+.

Step 6: Synthesis of 1-Benzyl-2,3-dimethyl-5-[4-(1H-tetrazol-5-ylmethoxy)-phenyl]-1H-indole. The desired product was prepared using a procedure similar to step 6 of example 3. Thus, [4-(1-benzyl-2,3-dimethyl-1H-indol-5-yl)-phenoxy]-acetonitrile (0.202 g, 0.551 mmol) was reacted with NaN$_3$ (0.179 g, 2.756 mmol) and NH$_4$Cl (0.147 g, 2.756 mmol) in DMF (5 ml) to give the product (0.176 g, 0.430 mmol, 78%) as a yellow solid, dec. 229-232° C.
$^1$H NMR (DMSO-d$_6$) δ 2.24 (s, 3H), 2.28 (s, 3H), 5.39 (s, 2H), 5.51 (s, 2H), 6.98 (d, J=7.5 Hz, 2H), 7.12 (d, J=8.7 Hz, 2H), 7.20 (t, J=7.2 Hz, 1H), 7.26-7.29 (m, 3H), 7.38 (d, J=8.6 Hz, 1H), 7.61-7.63 (m, 3H), 16.40 (broad s, 1H); IR (solid) 3020, 2910, 2580, 1520, 1480, 1450, 1350, 1260, and 1240 cm$^{-1}$; [ESI(−)], m/z 408 (M−H)−; Anal. Calcd. for C$_{25}$H$_{23}$N$_5$O.0.25H$_2$O: C, 72.53; H, 5.72; N, 16.92; Found: C, 72.76; H, 5.53; N, 17.15.

Example 7

Synthesis of [4-(1-Benzyl-2,3-dimethyl-1H-indol-5-yl)-phenoxy]-acetic Acid

Step 1: Synthesis of [4-(1-Benzyl-2,3-dimethyl-1H-indol-5-yl)-phenoxy]-acetic acid methyl ester. The desired product was prepared using a procedure similar to step 1 of example 4. Thus, 4-(1-benzyl-2,3-dimethyl-1H-indol-5-yl)-phenol (0.300 g, 0.916 mmol) was reacted with K$_2$CO$_3$ (0.152 g, 1.099 mmol) and methyl bromoacetate (0.168 g, 1.099 mmol)

in acetone (10 ml) to give the product (0.233 g, 0.583 mmol, 64%) as a purple solid, mp 133-136° C. $^1$H NMR (DMSO-d$_6$) δ 2.24 (s, 3H), 2.28 (s, 3H), 3.71 (s, 3H), 4.82 (s, 2H), 5.39 (s, 2H), 6.98 (d, J=8.6 Hz, 4H), 7.20 (t, J=7.2 Hz, 1H), 7.26-7.29 (m, 3H), 7.37 (d, J=8.4 Hz, 1H), 7.58 (d, J=8.7 Hz, 2H), 7.62 (s, 1H); [ESI(+)], m/z 400 (M+H)$^+$.

Step 2: Synthesis of [4-(1-Benzyl-2,3-dimethyl-1H-indol-5-yl)-phenoxy]-acetic acid. The desired product was prepared using a procedure similar to step 2 of example 4. Thus, [4-(1-benzyl-2,3-dimethyl-1H-indol-5-yl)-phenoxy]-acetic acid methyl ester (0.230 g, 0.576 mmol) was reacted with 1N KOH (1.2 ml) in THF/MeOH (6 ml/4 ml) to give the product (0.139 g, 0.361 mmol, 63%) as an off-white solid, mp 203-206° C. $^1$H NMR (DMSO-d$_6$) δ 2.24 (s, 3H), 2.27 (s, 3H), 4.68 (s, 2H), 5.38 (s, 2H), 6.95-6.99 (m, 4H), 7.20 (t, J=7.2 Hz, 1H), 7.25-7.29 (m, 3H), 7.37 (d, J=8.6 Hz, 1H), 7.58 (d, J=8.7 Hz, 2H), 7.62 (s, 1H), 13.00 (broad s, 1H); IR (solid) 3030, 2910, 1740, 1710, 1605, 1520, 1480, and 1240 cm$^{-1}$; [ESI(−)], m/z 384 (M−H)—; Anal. Calcd. for C$_{25}$H$_{23}$NO$_3$: C, 77.90; H, 6.01; N, 3.63; Found: C, 77.87; H, 5.99; N, 3.64.

Example 8

Synthesis of 9-Benzyl-6-[4-(1H-tetrazol-5-yl-methoxy)-phenyl]-2,3,4,9-tetrahydro-1H-carbazole Step 1: Synthesis of 6-Bromo-2,3,4,9-tetrahydro-1H-carbazole. The desired product was prepared using a procedure similar to step 1 of example 3. Thus, 4-bromophenylhydrazine, hydrochloride (5.398 g, 24.15 mmol) was reacted with cyclohexanone (2.257 g, 23 mmol) in ethanol (60 ml) to give the product (4.871 g, 19.473 mmol, 85%) as a white solid, mp 148-151° C. $^1$H NMR (DMSO-d$_6$) δ 1.74-1.83 (m, 4H), 2.57 (t, J=6.0 Hz, 2H), 2.68 (t, J=5.7 Hz, 2H), 7.06 (dd, J=1.8, 8.4 Hz, 1H), 7.18 (d, J=8.4 Hz, 1H), 7.46 (s, 1H), 10.84 (s, 1H); [ESI(−)], m/z 248/250 (M−H)$^-$.

Step 2: Synthesis of 9-Benzyl-6-bromo-2,3,4,9-tetrahydro-1H-carbazole. The desired product was prepared using a procedure similar to step 2 of example 3. Thus, 6-bromo-2,3,4,9-tetrahydro-1H-carbazole (1.876 g, 7.5 mmol) was reacted with k-t-butoxide (0.884 g, 7.875 mmol) and benzyl bromide (1.352 g, 7.875 mmol) in DMF (20 ml) to give the product (2.225 g, 6.539 mmol, 87%) as an oily, yellow solid. $^1$H NMR (DMSO-d$_6$) δ 1.74-1.83 (m, 4H), 2.61-2.64 (m, 4H), 5.32 (s, 2H), 6.99 (d, J=7.6 Hz, 2H), 7.11 (dd, 1.8, 8.7 Hz, 1H), 7.21 (t, J=7.2 Hz, 1H), 7.27 (t, J=7.3 Hz, 2H), 7.33 (d, J=8.6 Hz, 1H), 7.55 (d, J=1.5 Hz, 1H); [ESI(+)], m/z 340/342 (M+H)$^+$.

Step 3: Synthesis of 9-Benzyl-6-(4-methoxy-phenyl)-2,3,4,9-tetrahydro-1H-carbazole. The desired product was prepared using a procedure similar to step 3 of example 3. Thus, 9-benzyl-6-bromo-2,3,4,9-tetrahydro-1H-carbazole (2.217 g, 6.516 mmol) was reacted with aqueous 2M K$_2$CO$_3$ (6.5 ml), 4-methoxyphenylboronic acid (1.188 g, 7.819 mmol) and [1,1'-bis(diphenylphosphino)ferrocene]dichloropalladium (II) complex with dichloromethane (1:1) (0.106 g, 0.130 mmol) in dioxane (65 ml) to give the product (1.94 g, 5.28 mmol, 81%) as a viscous brown oil. $^1$H NMR (DMSO-d$_6$) δ 1.79-1.86 (m, 4H), 2.63-2.71 (m, 4H), 3.78 (s, 3H), 5.33 (s, 2H), 6.98 (d, J=8.7 Hz, 2H), 7.03 (d, J=7.5 Hz, 2H), 7.21 (t, J=7.0 Hz, 1H), 7.25-7.30 (m, 3H), 7.38 (d, J=8.6 Hz, 1H), 7.56-7.58 (m, 3H); [ESI(+)], m/z 368 (M+H)$^+$.

Step 4: Synthesis of 4-(9-Benzyl-6,7,8,9-tetrahydro-5H-carbazol-3-yl)-phenol. The desired product was prepared using a procedure similar to step 4 of example 3. Thus, 9-benzyl-6-(4-methoxy-phenyl)-2,3,4,9-tetrahydro-1H-carbazole (1.930 g, 5.252 mmol) was reacted with BBr$_3$ (6.3 ml of a 1M solution in CH$_2$Cl$_2$) to give the product (0.840 g, 2.377 mmol, 45%) as a pale-green foam. $^1$H NMR (DMSO-d$_6$) δ 1.78-1.85 (m, 4H), 2.63-2.70 (m, 4H), 5.32 (s, 2H), 6.81 (d, J=8.4 Hz, 2H), 7.03 (d, J=7.5 Hz, 2H), 7.19-7.23 (m, 2H), 7.28 (t, J=7.6 Hz, 2H), 7.36 (d, J=8.6 Hz, 1H), 7.44 (d, J=8.6 Hz, 2H), 7.53 (s, 1H), 9.32 (s, 1H); [ESI(+)], m/z 354 (M+H)$^+$.

Step 5: Synthesis of [4-(9-Benzyl-6,7,8,9-tetrahydro-5H-carbazol-3-yl)-phenoxy]-acetonitrile. The desired product was prepared using a procedure similar to step 5 of example 3. Thus, 4-(9-benzyl-6,7,8,9-tetrahydro-5H-carbazol-3-yl)-phenol (0.421 g, 1.191 mmol) was reacted with K$_2$CO$_3$ (0.198 g, 1.429 mmol) and bromoacetonitrile (0.171 g, 1.429 mmol) in acetone to give the product (0.369 g, 0.940 mmol, 79%) as a white solid, mp 149-153° C. $^1$H NMR (DMSO-d$_6$) δ 1.79-1.86 (m, 4H), 2.63-2.72 (m, 4H), 5.19 (s, 2H), 5.34 (s, 2H), 7.04 (d, J=7.5 Hz, 2H), 7.12 (d, J=7.5 Hz, 2H), 7.22 (t, J=7.2 Hz, 1H), 7.27-7.30 (m, 3H), 7.41 (d, J=8.6 Hz, 1H), 7.62 (s, 1H), 7.65 (d, J=8.6 Hz, 2H); [ESI(+)], m/z 393 (M+H)$^+$.

Step 6: Synthesis of 9-Benzyl-6-[4-(1H-tetrazol-5-yl-methoxy)-phenyl]-2,3,4,9-tetrahydro-1H-carbazole. The desired product was prepared using a procedure similar to step 6 of example 3. Thus, [4-(9-benzyl-6,7,8,9-tetrahydro-5H-carbazol-3-yl)-phenoxy]-acetonitrile (0.357 g, 0.910 mmol) was reacted with NaN$_3$ (0.296 g, 4.548 mmol) and NH$_4$Cl (0.243 g, 4.548 mmol) in DMF (10 ml) to give the product (0.329 g, 0.755 mmol, 83%) as a white solid, dec. 228-230° C. $^1$H NMR (DMSO-d$_6$) δ 1.79-1.85 (m, 4H), 2.64-2.71 (m, 4H), 5.33 (s, 2H), 5.50 (s, 2H), 7.03 (d, J=7.6 Hz, 2H), 7.11 (d, J=8.7 Hz, 2H), 7.21 (t, J=7.2 Hz, 1H), 7.27-7.30 (m, 3H), 7.39 (d, J=8.6 Hz, 1H), 7.59-7.61 (m, 3H), 16.80 (broad s, 1H); IR (solid) 3030, 2920, 2590, 1520, 1470 and 1240 cm$^{-1}$; [ESI(+)], m/z 436 (M+H)$^+$; Anal. Calcd. for C$_{27}$H$_{25}$N$_5$O: C, 74.46; H, 5.79; N, 16.08; Found: C, 74.34; H, 5.46; N, 16.26.

Example 9

Synthesis of [4-(9-Benzyl-6,7,8,9-tetrahydro-5H-carbazol-3-yl)-phenoxy]-acetic Acid Step 1: Synthesis of [4-(9-Benzyl-6,7,8,9-tetrahydro-5H-carbazol-3-yl)-phenoxy]-acetic acid methyl ester. The desired product was prepared using a procedure similar to step 1 of example 4. Thus, 4-(9-benzyl-6,7,8,9-tetrahydro-5H-carbazol-3-yl)-phenol (0.419 g, 1.185 mmol) was reacted with K$_2$CO$_3$ (0.213 g, 1.541 mmol) and methyl bromoacetate (0.236 g, 1.541 mmol) in acetone to give the product (0.362 g, 0.851 mmol, 72%) as a white solid, mp 109-112° C. $^1$H NMR (DMSO-d$_6$) δ 1.77-1.87 (m, 4H), 2.65 (t, J=5.3 Hz, 2H), 2.70 (t, J=6.0 Hz, 2H), 3.71 (s, 3H), 4.81 (s, 2H), 5.33 (s, 2H), 6.98 (d, J=8.7 Hz, 2H), 7.03 (d, J=7.3 Hz, 2H), 7.21 (t, J=7.2 Hz, 1H), 7.25-7.30 (m, 3H), 7.39 (d, J=8.4 Hz, 1H), 7.57 (d, J=8.7 Hz, 2H), 7.58 (d, J=1.1 Hz, 1H); [ESI(+)], m/z 426 (M+H)$^+$.

Step 2: Synthesis of [4-(9-Benzyl-6,7,8,9-tetrahydro-5H-carbazol-3-yl)-phenoxy]-acetic acid. The desired product was prepared using a procedure similar to step 2 of example 4. Thus, [4-(9-benzyl-6,7,8,9-tetrahydro-5H-carbazol-3-yl)-phenoxy]-acetic acid methyl ester (0.355 g, 0.834 mmol) was reacted with 1N KOH (1.7 ml) in THF/MeOH (6 ml/4 ml) to give the product (0.261 g, 0.634 mmol, 74%) as a pale-yellow solid, mp 176-180° C. $^1$H NMR (DMSO-d$_6$) δ 1.77-1.86 (m, 4H), 2.65 (t, J=5.3 Hz, 2H), 2.70 (t, J=6.0 Hz, 2H), 4.69 (s, 2H), 5.33 (s, 2H), 6.96 (d, J=8.7 Hz, 2H), 7.03 (d, J=7.3 Hz, 2H), 7.21 (t, J=7.2 Hz, 1H), 7.25-7.30 (m, 3H), 7.39 (d, J=8.6 Hz, 1H), 7.56 (d, J=8.7 Hz, 2H), 7.58 (d, J=1.7 Hz, 1H), 13.00 (broad s, 1H); IR (solid) 3020, 2920, 1740, 1520, 1470, and 1240 cm⁻¹; [ESI(−)], m/z 410 (M−H)⁻; Anal. Calcd. for $C_{27}H_{25}NO_3$: C, 78.81; H, 6.12; N, 3.40; Found: C, 78.69; H, 6.21; N, 3.20.

Example 10

Synthesis of 9-Methyl-6-[4-(1H-tetrazol-5-yl-methoxy)-phenyl]-2,3,4,9-tetrahydro-1H-carbazole Step 1: Synthesis of 6-Bromo-9-methyl-2,3,4,9-tetrahydro-1H-carbazole. The desired product was prepared using a procedure similar to step 2 of example 3. Thus, 6-bromo-2,3,4,9-tetrahydro-1H-carbazole (1.501 g, 6 mmol) was reacted with k-t-butoxide (0.707 g, 6.3 mmol) and methyl iodide (0.894 g, 6.3 mmol) in DMF (15 ml) to give the desired product (1.443 g, 5.463 mmol, 91%) as an off-white solid, mp 70-73° C. ¹H NMR (DMSO-d₆) δ 1.73-1.77 (m, 2H), 1.82-1.87 (m, 2H), 2.58 (t, J=6.1 Hz, 2H), 2.70 (t, J=6.1 Hz, 2H), 3.58 (s, 3H), 7.13 (dd, J=1.7, 8.6 Hz, 1H), 7.32 (d, J=8.6 Hz, 1H), 7.55 (d, J=1.5 Hz, 1H); [EI], m/z 263/265 (M)⁺.

Step 2: Synthesis of 6-(4-Methoxy-phenyl)-9-methyl-2,3,4,9-tetrahydro-1H-carbazole. The desired product was prepared using a procedure similar to step 3 of example 3. Thus, 6-bomo-9-methyl-2,3,4,9-tetrahydro-1H-carbazole (1.428 g, 5.406 mmol) was reacted with aqueous 2M $K_2CO_3$ (5.4 ml), 4-methoxyphenylboronic acid (0.986 g, 6.487 mmol) and [1,1'-bis(diphenylphosphino)ferrocene]dichloropalladium (II) complex with dichloromethane (1:1) (0.088 g, 0.108 mmol) in dioxane (54 ml) to give the product (1.245 g, 4.273 mmol, 79%) as a light-brown, oily solid. ¹H NMR (DMSO-d₆) δ 1.73-1.90 (m, 4H), 2.66 (t, J=5.6 Hz, 2H), 2.71 (t, J=5.6 Hz, 2H), 3.61 (s, 3H), 3.78 (s, 3H), 6.98 (d, J=8.7 Hz, 2H), 7.30 (dd, J=1.5, 8.4 Hz, 1H), 7.38 (d, J=8.4 Hz, 1H), 7.55 (d, J=1.4 Hz, 1H), 7.58 (d, J=8.7 Hz, 2H); [ESI(+)], m/z 292 (M+H)⁺.

Step 3: Synthesis of 4-(9-Methyl-6,7,8,9-tetrahydro-5H-carbazol-3-yl)-phenol. The desired product was prepared using a procedure similar to step 4 of example 3. Thus, 6-(4-methoxy-phenyl)-9-methyl-2,3,4,9-tetrahydro-1H-carbazole (1.214 g, 4.166 mmol) was reacted with $BBr_3$ (5.0 ml of a 1M solution in $CH_2Cl_2$) to give the product (0.382 g, 1.377 mmol, 33%) as a brown oil. ¹H NMR (DMSO-d₆) δ 1.76-1.80 (m, 2H), 1.83-1.90 (m, 2H), 2.65 (t, J=5.8 Hz, 2H), 2.71 (t, J=5.8 Hz, 2H), 3.59 (s, 3H), 6.81 (d, J=8.6 Hz, 2H), 7.26 (dd, J=1.2, 8.4 Hz, 1H), 7.35 (d, J=8.4 Hz, 1H), 7.45 (d, J=8.6 Hz, 2H), 7.50 (s, 1H), 9.31 (s, 1H); [ESI(+)], m/z 276 (M+H)⁺.

Step 4: Synthesis of [4-(9-Methyl-6,7,8,9-tetrahydro-5H-carbazol-3-yl)-phenoxy]-acetonitrile. The desired product was prepared using a procedure similar to step 5 of example 3. Thus, 4-(9-methyl-6,7,8,9-tetrahydro-5H-carbazol-3-yl)-phenol (0.194 g, 0.699 mmol) was reacted with $K_2CO_3$ (0.116 g, 0.839 mmol) and bromoacetonitrile (0.101 g, 0.839 mmol) in acetone (8 ml) to give the product (0.153 g, 0.484 mmol, 69%) as a white solid, mp 204-206° C. ¹H NMR (DMSO-d₆) δ 1.77-1.82 (m, 2H), 1.84-1.90 (m, 2H), 2.67 (t, J=5.8 Hz, 2H), 2.72 (t, J=5.8 Hz, 2H), 3.61 (s, 3H), 5.19 (s, 2H), 7.12 (d, J=8.7 Hz, 2H), 7.33 (dd, J=1.4, 8.4 Hz, 1H), 7.40 (d, J=8.6 Hz, 1H), 7.59 (s, 1H), 7.65 (d, J=8.6 Hz, 2H); [ESI(+)], m/z 317 (M+H)⁺.

Step 5: Synthesis of 9-Methyl-6-[4-(1H-tetrazol-5-yl-methoxy)-phenyl]-2,3,4,9-tetrahydro-1H-carbazole. The desired product was prepared using a procedure similar to step 6 of example 3. Thus, [4-(9-methyl-6,7,8,9-tetrahydro-5H-carbazol-3-yl)-phenoxy]-acetonitrile (0.149 g, 0.471 mmol) was reacted with $NaN_3$ (0.153 g, 2.355 mmol) and $NH_4Cl$ (0.126 g, 2.355 mmol) in DMF (5 ml) to give the product (0.060 g, 0.167 mmol, 35%) as a white solid, dec. 205-211° C. ¹H NMR (DMSO-d₆) δ 1.76-1.81 (m, 2H), 1.86-1.90 (m, 2H), 2.66 (t, J=6.0 Hz, 2H), 2.71 (t, J=5.8 Hz, 2H), 3.61 (s, 3H), 5.51 (s, 2H), 7.11 (d, J=8.7 Hz, 2H), 7.31 (dd, J=1.5, 8.4 Hz, 1H), 7.38 (d, J=8.4 Hz, 1H), 7.56 (s, 1H), 7.61 (d, J=8.7 Hz, 2H), 16.78 (broad s, 1H); IR (solid) 2930, 2850, 1520, 1480, and 1240 cm⁻¹; [ESI(+)], m/z 360 (M+H)⁺; Anal. Calcd. for $C_{21}H_{21}N_5O$: C, 70.18; H, 5.89; N, 19.48; Found: C, 69.94; H, 5.70; N, 19.67.

Example 11

Synthesis of 1,3-Dibenzyl-2-methyl-5-[4-(1H-tetrazol-5-ylmethoxy)-phenyl]-1H-indole Step 1: Synthesis of 3-Benzyl-5-bromo-2-methyl-1H-indole. The desired product was prepared using a procedure similar to step 1 of example 3. Thus, 4-bromophenylhydrazine, hydrochloride (4.694 g, 21 mmol) was reacted with benzylacetone (2.964 g, 20 mmol) in ethanol (60 ml) to give the product (3.199 g, 10.657 mmol, 51%) as a tan solid, mp 130-134° C. ¹H NMR (DMSO-d₆) δ 2.36 (s, 3H), 3.95 (s, 2H), 7.05 (dd, J=1.8, 8.4 Hz, 1H), 7.12 (t, J=7.2 Hz, 1H), 7.17-7.20 (m, 3H), 7.23 (t, J=7.8 Hz, 2H), 7.43 (d, J=1.7 Hz, 1H), 11.01 (s, 1H); [ESI(−)], m/z 298/300 (M−H)⁻.

Step 2: Synthesis of 1,3-Dibenzyl-5-bromo-2-methyl-1H-indole. The desired product was prepared using a procedure similar to step 2 of example 3. Thus, 3-benzyl-5-bromo-2-methyl-1H-indole (1.651 g, 5.5 mmol) was reacted with k-t-butoxide (0.648 g, 5.775 mmol) and benzyl bromide (0.991 g, 5.775 mmol) in DMF (20 ml) to give the product (1.842 g, 4.719 mmol, 86%) as a viscous brown oil. ¹H NMR (DMSO-d₆) δ 2.33 (s, 3H), 4.03 (s, 2H), 5.42 (s, 2H), 6.95 (d, J=7.3 Hz, 2H), 7.10-7.14 (m, 2H), 7.18-7.29 (m, 7H), 7.34 (d, J=8.7 Hz, 1H), 7.53 (d, J=1.8 Hz, 1H); [ESI(+)], m/z 390/392 (M+H)⁺.

Step 3: Synthesis of 1,3-Dibenzyl-5-(4-methoxy-phenyl)-2-methyl-1H-indole. The desired product was prepared using a procedure similar to step 3 of example 3. Thus, 1,3-dibenzyl-5-bromo-2-methyl-1H-indole (1.842 g, 6.133 mmol) was reacted with aqueous 2M $K_2CO_3$ (6.1 ml), 4-methoxyphenylboronic acid (1.118 g, 7.360 mmol) and [1,1'-bis(diphenylphosphino)ferrocene]dichloropalladium (II) complex with dichloromethane (1:1) (0.100 g, 0.123 mmol) in dioxane (61 ml) to give the product (0.702 g, 1.681 mmol, 27%) as a pale-yellow solid, mp 136-139° C. ¹H NMR (DMSO-d₆) δ 2.35 (s, 3H), 3.76 (s, 3H), 4.10 (s, 2H), 5.43 (s, 2H), 6.95-7.00 (m, 4H), 7.09-7.13 (m, 1H), 7.20-7.30 (m, 8H), 7.39 (d, J=8.6 Hz, 1H), 7.48-7.51 (m, 2H), 7.57 (d, J=1.5 Hz, 1H); [ESI(+)], m/z 418 (M+H)⁺.

Step 4: Synthesis of 4-(1,3-Dibenzyl-2-methyl-1H-indol-5-yl)-phenol. The desired product was prepared using a procedure similar to step 4 of example 3. Thus, 1,3-dibenzyl-5-(4-methoxy-phenyl)-2-methyl-1H-indole (0.692 g, 1.657 mmol) was reacted with $BBr_3$ (2.0 ml of a 1M solution in $CH_2Cl_2$) to give the product (0.347 g, 0.860 mmol, 52%) as an off-white solid, mp 170-171° C. ¹H NMR (DMSO-d₆) δ 2.34 (s, 3H), 4.09 (s, 2H), 5.41 (s, 2H), 6.79 (d, J=8.5 Hz, 2H), 6.98 (d, J=7.3 Hz, 2H), 7.09-7.14 (m, 1H), 7.20-7.23 (m, 6H), 7.28 (t, J=7.1 Hz, 2H), 7.35-7.38 (m, 3H), 7.52 (d, J=1.3 Hz, 1H), 9.31 (s, 1H); IR (solid) 3530, 3020, 1600, 1480, 1260 and 11180 cm⁻¹; [ESI(+)], m/z 404 (M+H)⁺; Anal. Calcd. for $C_{29}H_{25}NO$: C, 86.32; H, 6.24; N, 3.47; Found: C, 86.30; H, 5.99; N, 3.09.

Step 5: Synthesis of [4-(1,3-Dibenzyl-2-methyl-1H-indol-5-yl)-phenoxy]-acetonitrile. The desired product was prepared using a procedure similar to step 5 of example 3. Thus, 4-(1,3-dibenzyl-2-methyl-1H-indol-5-yl)-phenol (0.164 g, 0.406 mmol) was reacted with $K_2CO_3$ (0.073 g, 0.528 mmol)

and bromoacetonitrile (0.063 g, 0.528 mmol) in acetone (5 ml) to give the product (0.164 g, 0.371 mmol, 91%) as a pale-yellow, viscous oil. $^1$H NMR (DMSO-d$_6$) δ 2.35 (s, 3H), 4.11 (s, 2H), 5.18 (s, 2H), 5.43 (s, 2H), 6.99 (d, J=7.2 Hz, 2H), 7.09-7.13 (m, 3H), 7.20-7.26 (m, 5H), 7.27-7.30 (m, 3H), 7.41 (d, J=8.4 Hz, 1H), 7.56-7.59 (m, 2H), 7.62 (d, J=1.7 Hz, 1H); [ESI(+)], m/z 443 (M+H)$^+$.

Step 6: Synthesis of 1,3-Dibenzyl-2-methyl-5-[4-(1H-tetrazol-5-ylmethoxy)-phenyl]-1H-indole. The desired product was prepared using a procedure similar to step 6 of example 3. Thus, [4-(1,3-dibenzyl-2-methyl-1H-indol-5-yl)-phenoxy]-acetonitrile (0.160 g, 0.362 mmol) was reacted with NaN$_3$ (0.118 g, 1.808 mmol) and NH$_4$Cl (0.097 g, 1.808 mmol) in DMF (5 ml) to give the product (0.136 g, 0.280 mmol, 77%) as a white solid, mp 190-192° C. $^1$H NMR (DMSO-d$_6$) δ 2.35 (s, 3H), 4.10 (s, 2H), 5.43 (s, 2H), 5.49 (s, 2H), 6.99 (d, J=7.0 Hz, 2H), 7.09-7.13 (m, 3H), 7.20-7.30 (m, 8H), 7.40 (d, J=8.4 Hz, 1H), 7.54 (d, J=8.9 Hz, 2H), 7.60 (d, J=1.7 Hz, 1H); IR (solid) 3030, 2905, 2850, 1605, 1520, 1480, 1440, 1360, 1270, and 1250 cm$^{-1}$; [ESI(−)], m/z 484 (M−H)$^-$; Anal. Calcd. for C$_{31}$H$_{27}$N$_5$O: C, 76.88; H, 5.60; N, 14.42; Found: C, 76.71; H, 5.57; N, 14.37.

Example 12

Synthesis of [4-(1,3-Dibenzyl-2-methyl-1H-indol-5-yl)-phenoxy]-acetic Acid

Step 1: Synthesis of [4-(1,3-Dibenzyl-2-methyl-1H-indol-5-yl)-phenoxy]-acetic acid methyl ester. The desired product was prepared using a procedure similar to step 1 of example 4. Thus, 4-(1,3-dibenzyl-2-methyl-1H-indol-5-yl)-phenol (0.155 g, 0.384 mmol) was reacted with K$_2$CO$_3$ (0.069 g, 0.499 mmol) and methyl bromoacetate (0.076 g, 0.499 mmol) in acetone (5 ml) to give the product (0.152 g, 0.320 mmol, 83%) as a viscous oil. $^1$H NMR (DMSO-d$_6$) δ 2.35 (s, 3H), 3.70 (s, 3H), 4.10 (s, 2H), 4.80 (s, 2H), 5.42 (s, 2H), 6.94-7.00 (m, 4H), 7.09-7.13 (m, 1H), 7.20-7.30 (m, 8H), 7.39 (d, J=8.6 Hz, 1H), 7.49 (d, J=8.9 Hz, 2H), 7.58 (d, J=1.7 Hz, 1H); [ESI(+)], m/z 476 (M+H)$^+$.

Step 2: Synthesis of [4-(1,3-Dibenzyl-2-methyl-1H-indol-5-yl)-phenoxy]-acetic acid. The desired product was prepared using a procedure similar to step 2 of example 4. Thus, [4-(1,3-dibenzyl-2-methyl-1H-indol-5-yl)-phenoxy]-acetic acid methyl ester (0.147 g, 0.309 mmol) was reacted with 1N KOH (0.62 ml) in THF/MeOH (3 ml/2 ml) to give the product (0.072 g, 0.156 mmol, 50%) as a tan solid, mp 180-183° C. $^1$H NMR (DMSO-d$_6$), δ 2.35 (s, 3H), 4.10 (s, 2H), 4.66 (s, 2H), 5.42 (s, 2H), 6.94 (d, J=8.9 Hz, 2H), 6.99 (d, J=7.0 Hz, 2H), 7.09-7.13 (m, 1H), 7.20-7.30 (m, 8H), 7.39 (d, J=8.4 Hz, 1H), 7.49 (d, J=8.7 Hz, 2H), 7.58 (d, J=1.5 Hz, 1H), 13.00 (broad s, 1H); IR (solid) 3010, 2905, 1730, 1520, 1480, and 1240 cm$^{-1}$; [ESI(+)], m/z 462 (M+H)$^+$; Anal. Calcd. for C$_{31}$H$_{27}$NO$_3$: C, 80.67; H, 5.90; N, 3.03; Found: C, 80.60; H, 5.79; N, 2.94.

Example 13

Synthesis of 3-Benzyl-1,2-dimethyl-5-[4-(1H-tetrazol-5-ylmethoxy)-phenyl]-1H-indole Step 1: Synthesis of 3-Benzyl-5-bromo-1,2-dimethyl-1H-indole. The desired product was prepared using a procedure similar to step 2 of example 3. Thus, 3-benzyl-5-bromo-2-methyl-1H-indole (1.530 g, 5.097 mmol) was reacted with k-t-butoxide (0.601 g, 5.352 mmol) and methyl iodide (0.760 g, 5.352 mmol) in DMF (15 ml) to give the product (1.453 g, 4.624 mmol, 91%) as a yellow solid, mp 104-106° C. $^1$H NMR (DMSO-d$_6$) δ 2.39 (s, 3H), 3.65 (s, 3H), 3.99 (s, 2H), 7.10-7.14 (m, 2H), 7.18 (d, J=6.7 Hz, 2H), 7.22 (t, J=7.6 Hz, 2H), 7.34 (d, J=8.6 Hz, 1H), 7.49 (d, J=1.8 Hz, 1H); [ESI(+)], m/z 314/316 (M+H)$^+$.

Step 2: Synthesis of 3-Benzyl-5-(4-methoxy-phenyl)-1,2-dimethyl-1H-indole. The desired product was prepared using a procedure similar to step 3 of example 3. Thus, 3-benzyl-5-bromo-1,2-dimethyl-1H-indole (1.453 g, 4.624 mmol) was reacted with aqueous 2M K$_2$CO$_3$ (4.6 ml), 4-methoxyphenyl-boronic acid (0.843 g, 5.549 mmol) and [1,1'-bis(diphenylphosphino)ferrocene]dichloropalladium (II) complex with dichloromethane (1:1) (0.076 g, 0.092 mmol) in dioxane (46 ml) to give the product (0.419 g, 1.227 mmol, 27%) as a solid, mp 139-141° C. $^1$H NMR (DMSO-d$_6$) δ 2.40 (s, 3H), 3.67 (s, 3H), 3.76 (s, 3H), 4.06 (s, 2H), 6.97 (d, J=8.9 Hz, 2H), 7.08-7.12 (m, 1H), 7.19-7.24 (m, 4H), 7.29 (dd, J=1.8, 8.6 Hz, 1H), 7.39 (d, J=8.4 Hz, 1H), 7.51 (d, J=8.9 Hz, 2H), 7.55 (d, J=1.5 Hz, 1H); [ESI(+)], m/z 342 (M+H)$^+$.

Step 3: Synthesis of 4-(3-Benzyl-1,2-dimethyl-1H-indol-5-yl)-phenol. The desired product was prepared using a procedure similar to step 4 of example 3. Thus, 3-benzyl-5-(4-methoxy-phenyl)-1,2-dimethyl-1H-indole (0.419 g, 1.227 mmol) was reacted with BBr$_3$ (1.5 ml of a 1M solution in CH$_2$Cl$_2$) to give the product (0.329 g, 1.004 mmol, 82%) as an off-white solid, dec. 129-133° C. $^1$H NMR (DMSO-d$_6$) δ 2.35 (s, 3H), 3.62 (s, 3H), 4.01 (s, 2H), 6.75 (d, J=8.7 Hz, 2H), 7.04-7.09 (m, 1H), 7.15-7.22 (m, 5H), 7.31-7.37 (m, 3H), 7.47 (d, J=1.5 Hz, 1H), 9.27 (s, 1H): [ESI(+)], m/z 328 (M+H)$^+$.

Step 4: Synthesis of [4-(3-Benzyl-1,2-dimethyl-1H-indol-5-yl)-phenoxy]-acetonitrile. The desired product was prepared using a procedure similar to step 5 of example 3. Thus, 4-(3-benzyl-1,2-dimethyl-1H-indol-5-yl)-phenol (0.159 g, 0.486 mmol) was reacted with K$_2$CO$_3$ (0.087 g, 0.631 mmol) and bromoacetonitrile (0.076 g, 0.631 mmol) in acetone (5 ml) to give the product (0.161 g, 0.439 mmol, 90%) as a white solid, mp 135-138° C. $^1$H NMR (DMSO-d$_6$) δ 2.40 (s, 3H), 3.68 (s, 3H), 4.07 (s, 2H), 5.18 (s, 2H), 7.08-7.12 (m, 3H), 7.20-7.25 (m, 4H), 7.32 (dd, J=1.8, 8.6 Hz, 1H), 7.41 (d, J=8.4 Hz, 1H), 7.57-7.60 (m, 3H); [ESI(+)], m/z 367 (M+H)$^+$.

Step 5: Synthesis of 3-Benzyl-1,2-dimethyl-5-[4-(1H-tetrazol-5-ylmethoxy)-phenyl]-1H-indole. The desired product was prepared using a procedure similar to step 6 of example 3. Thus, [4-(3-benzyl-1,2-dimethyl-1H-indol-5-yl)-phenoxy]-acetonitrile (0.144 g, 0.393 mmol) was reacted with NaN$_3$ (0.128 g, 1.965 mmol) and NH$_4$Cl (0.105 g, 1.965 mmol) in DMF (5 ml) to give the product (0.133 g, 0.325 mmol, 83%) as a white solid, dec. 214-215° C.

$^1$H NMR (DMSO-d$_6$) δ 2.40 (s, 3H), 3.67 (s, 3H), 4.06 (s, 2H), 5.49 (s, 2H), 7.08-7.11 (m, 3H), 7.19-7.24 (m, 4H), 7.30 (dd, J=1.7, 8.4 Hz, 1H), 7.40 (d, J=8.4 Hz, 1H), 7.55 (d, J=8.7 Hz, 2H), 7.58 (d, J=1.4 Hz, 1H), 16.80 (broad s, 1H); IR (solid) 3020, 2905, 1520, 1480, 1440, 1380, and 1250 cm$^{-1}$; [ESI(+)], m/z 410 (M+H)$^+$; Anal. Calcd. for C$_{25}$H$_{23}$N$_5$O: C, 73.33; H, 5.66; N, 17.10; Found: C, 73.12; H, 5.56; N, 17.25.

Example 14

Synthesis of [4-(3-Benzyl-1,2-dimethyl-1H-indol-5-yl)-phenoxy]-acetic Acid

Step 1: Synthesis of [4-(3-Benzyl-1,2-dimethyl-1H-indol-5-yl)-phenoxy]-acetic acid methyl ester. The desired product was prepared using a procedure similar to step 1 of example 4. Thus, 4-(3-benzyl-1,2-dimethyl-1H-indol-5-yl)-phenol (0.162 g, 0.495 mmol) was reacted with K$_2$CO$_3$ (0.089 g, 0.643 mmol) and methyl bromoacetate (0.098 g, 0.643 mmol) in acetone (5 ml) to give the product (0.161 g, 0.403 mmol, 81%) as an off-white solid, mp 113-117° C. $^1$H NMR (DMSO-d$_6$) δ 2.40 (s, 3H), 3.67 (s, 3H), 3.70 (s, 3H), 4.06 (s, 2H), 4.80 (s, 2H), 6.96 (d, J=8.9 Hz, 2H), 7.08-7.11 (m, 1H), 7.19-7.24 (m, 4H), 7.29 (dd, J=1.7, 8.4 Hz, 1H), 7.39 (d, J=8.4 Hz, 1H), 7.51 (d, J=8.9 Hz, 2H), 7.56 (d, J=1.5 Hz, 1H); [ESI(+)], m/z 400 (M+H)$^+$.

Step 2: Synthesis of [4-(3-Benzyl-1,2-dimethyl-1H-indol-5-yl)-phenoxy]-acetic acid. The desired product was prepared using a procedure similar to step 2 of example 4. Thus, [4-(3-benzyl-1,2-dimethyl-1H-indol-5-yl)-phenoxy]-acetic acid methyl ester (0.151 g, 0.378 mmol) was reacted with 1N KOH (0.8 ml) in THF/MeOH (3 ml/2 ml) to give the product (0.068 g, 0.176 mmol, 47%) as a yellow solid, mp 204-207° C. $^1$H NMR (DMSO-d$_6$) δ 2.40 (s, 3H), 3.67 (s, 3H), 4.06 (s, 2H), 4.67 (s, 2H), 6.94 (d, J=8.9 Hz, 2H), 7.08-7.12 (m, 1H), 7.19-7.24 (m, 4H), 7.28 (dd, J=1.7, 8.6 Hz, 1H), 7.39 (d, J=8.4 Hz, 1H), 7.50 (d, J=8.7 Hz, 2H), 7.56 (d, J=1.4 Hz, 1H); IR (solid) 3020, 2880, 1740, 1710, 1510, 1480, and 1230 cm$^{-1}$; [ESI(+)], m/z 386 (M+H)$^+$; Anal. Calcd. for C$_{25}$H$_{23}$NO$_3$·0.3H$_2$O: C, 76.82; H, 6.17; N, 3.58; Found: C, 76.66; H, 6.00; N, 3.46.

Example 15

Synthesis of 1-Benzyl-3-methyl-2-phenyl-6-[4-(1H-tetrazol-5-ylmethoxy)-phenyl]-1H-indole Step 1: Synthesis of 6-Bromo-3-methyl-2-phenyl-1H-indole. The desired product was prepared using a procedure similar to step 1 of example 3. Thus, 3-bromophenylhydrazine, hydrochloride (9.857 g, 44.1 mmol) was reacted with propriophenone (5.636 g, 42 mmol) in ethanol (120 ml) to give the product (2.580 g, 9.016 mmol, 21%) as a tan solid, mp 144-147° C. $^1$H NMR (DMSO-d$_6$) δ 2.35 (s, 3H), 7.09 (dd, J=1.8, 8.5 Hz, 1H), 7.33 (t, J=7.4 Hz, 1H), 7.44-7.49 (m, 4H), 7.60-7.63 (m, 2H), 11.28 (s, 1H); [ESI(−)], m/z 284/286 (M−H)$^−$.

Step 2: Synthesis of 1-Benzyl-6-bromo-3-methyl-2-phenyl-1H-indole. The desired product was prepared using a procedure similar to step 2 of example 3. Thus, 6-bromo-3-methyl-2-phenyl-1H-indole (1.284 g, 4.489 mmol) was reacted with k-t-butoxide (0.529 g, 4.711 mmol) and benzyl bromide (0.809 g, 4.711 mmol) in DMF (10 ml) to give the product (1.440 g, 3.827 mmol, 85%) as a white solid, mp 97-101° C. $^1$H NMR (DMSO-d$_6$) δ 2.20 (s, 3H), 5.32 (s, 2H), 6.79-6.80 (m, 2H), 7.14-7.21 (m, 4H), 7.36-7.39 (m, 2H), 7.43 (t, J=7.2 Hz, 1H), 7.48 (t, J=6.9 Hz, 2H), 7.53 (d, J=8.4 Hz, 1H), 7.60 (d, J=1.7 Hz, 1H); [ESI(+)], m/z 376/378 (M+H)$^+$.

Step 3: Synthesis of 1-Benzyl-6-(4-methoxy-phenyl)-3-methyl-2-phenyl-1H-indole. The desired product was prepared using a procedure similar to step 3 of example 3. Thus, 1-benzyl-6-bromo-3-methyl-2-phenyl-1H-indole (1.432 g, 3.805 mmol) was reacted with aqueous 2M K$_2$CO$_3$ (3.8 ml), 4-methoxyphenylboronic acid (0.809 g, 5.327 mmol) and [1,1'-bis(diphenylphosphino)ferrocene]dichloropalladium (II) complex with dichloromethane (1:1) (0.093 g, 0.114 mmol) in dioxane (38 ml) to give the product (1.017 g, 2.861 mmol, 75%) as a white solid, mp 142-145° C. $^1$H NMR (DMSO-d$_6$) δ 2.23 (s, 3H), 3.77 (s, 3H), 5.39 (s, 2H), 6.86 (d, J=7.0 Hz, 2H), 6.98 (d, J=8.9 Hz, 2H), 7.13 (t, J=7.3 Hz, 1H), 7.18 (t, J=7.0 Hz, 2H), 7.34 (dd, J=1.5, 7.8 Hz, 1H), 7.38-7.44 (m, 3H), 7.48 (t, J=7.0 Hz, 2H), 7.55-7.61 (m, 4H); [ESI(+)], m/z 404 (M+H)$^+$.

Step 4: Synthesis of 4-(1-Benzyl-3-methyl-2-phenyl-1H-indol-6-yl)-phenol. The desired product was prepared using a procedure similar to step 4 of example 3. Thus, 1-benzyl-6-(4-methoxy-phenyl)-3-methyl-2-phenyl-1H-indole (1.017 g, 2.861 mmol) was reacted with BBr$_3$ (3.4 ml of a 1M solution in CH$_2$Cl$_2$) to give the product (0.726 g, 1.864 mmol, 65%) as a white solid, mp 141-143° C. $^1$H NMR (DMSO-d$_6$) δ 2.23 (s, 3H), 5.37 (s, 2H), 6.80 (d, J=8.6 Hz, 2H), 6.85 (d, J=7.2 Hz, 2H), 7.13 (t, J=7.3 Hz, 1H), 7.18 (t, J=7.0 Hz, 2H), 7.30 (dd, J=1.5, 8.3 Hz, 1H), 7.38-7.49 (m, 7H), 7.51 (d, J=0.9 Hz, 1H), 7.58 (d, J=8.1 Hz, 1H), 9.40 (s, 1H); IR (solid) 3300, 3030, 1600, 1520, 1450, 1350, 1260, 1230 and 1180 m$^{-1}$; [ESI(+)], m/z 390 (M+H)$^+$; Anal. Calcd. for C$_{28}$H$_{23}$NO: C, 86.34; H, 5.95; N, 3.60; Found: C, 85.88; H, 6.21; N, 3.36.

Step 5: Synthesis of [4-(1-Benzyl-3-methyl-2-phenyl-1H-indol-6-yl)-phenoxy]-acetonitrile. The desired product was prepared using a procedure similar to step 5 of example 3. Thus, 4-(1-benzyl-3-methyl-2-phenyl-1H-indol-6-yl)-phenol (0.291 g, 0.747 mmol) was reacted with K$_2$CO$_3$ (0.124 g, 0.896 mmol) and bromoacetonitrile (0.107 g, 0.896 mmol) in acetone (5 ml) to give the product (0.284 g, 0.663 mmol, 89%) as a white solid, mp 146-150° C. $^1$H NMR (DMSO-d$_6$) δ 2.20 (s, 3H), 5.15 (s, 2H), 5.36 (s, 2H), 6.82 (d, J=7.0 Hz, 2H), 7.08-7.17 (m, 5H), 7.32-7.47 (m, 4H), 7.45 (t, J=6.7 Hz, 2H), 7.57-7.63 (m, 4H); [ESI(+)], m/z 429 (M+H)$^+$.

Step 6: Synthesis of 1-Benzyl-3-methyl-2-phenyl-6-[4-(1H-tetrazol-5-ylmethoxy)-phenyl]-1H-indole. The desired product was prepared using a procedure similar to step 6 of example 3. Thus, [4-(1-benzyl-3-methyl-2-phenyl-1H-indol-6-yl)-phenoxy]-acetonitrile (0.288 g, 0.672 mmol) was reacted with NaN$_3$ (0.218 g, 3.360 mmol) and NH$_4$Cl (0.180 g, 3.360 mmol) in DMF (5 ml) to give the product (0.245 g, 0.520 mmol, 77%) as a white solid, dec. 224.5-226° C. $^1$H NMR (DMSO-d$_6$) δ 2.23 (s, 3H), 5.39 (s, 2H), 5.50 (s, 2H), 6.85 (d, J=7.3 Hz, 2H), 7.12 (t, J=8.4 Hz, 3H), 7.18 (t, J=7.0 Hz, 2H), 7.35-7.44 (m, 4H), 7.48 (t, J=7.2 Hz, 2H), 7.60-7.62 (m, 4H), 16.80 (broad s, 1H); IR (solid) 3020, 2910, 1605, 1520, 1480, 1460, 1340 and 1240 cm$^{-1}$; [ESI(−)], m/z 470 (M−H)$^−$; Anal. Calcd. for C$_{30}$H$_{25}$N$_5$O: C, 76.41; H, 5.34; N, 14.85; Found: C, 76.33; H, 5.28; N, 14.91.

Example 16

Synthesis of [4-(1-Benzyl-3-methyl-2-phenyl-1H-indol-6-yl)-phenoxy]-acetic Acid

Step 1: Synthesis of [4-(1-Benzyl-3-methyl-2-phenyl-1H-indol-6-yl)-phenoxy]-acetic acid methyl ester. The desired product was prepared using a procedure similar to step 1 of example 4. Thus, 4-(1-benzyl-3-methyl-2-phenyl-1H-indol-6-yl)-phenol (0.291 g, 0.747 mmol) was reacted with K$_2$CO$_3$ (0.134 g, 0.971 mmol) and methyl bromoacetate (0.149 g, 0.971 mmol) in acetone (5 ml) to give the product (0.305 g, 0.661 mmol, 88%) as a white solid, mp 145-148° C. $^1$H NMR (DMSO-d$_6$) δ 2.24 (s, 3H), 3.70 (s, 3H), 4.81 (s, 2H), 5.39 (s, 2H), 6.86 (d, J=7.2 Hz, 2H), 6.98 (d, J=8.9 Hz, 2H), 7.13 (t, J=7.2 Hz, 1H), 7.18 (t, J=7.0 Hz, 2H), 7.34 (dd, J=1.4, 8.1 Hz, 1H), 7.39-7.44 (m, 3H), 7.49 (t, J=7.0 Hz, 2H,) 7.56-7.62 (m, 4H); [ESI(+)], m/z 462 (M+H)$^+$.

Step 2: Synthesis of [4-(1-Benzyl-3-methyl-2-phenyl-1H-indol-6-yl)-phenoxy]-acetic acid. The desired product was prepared using a procedure similar to step 2 of example 4. Thus, [4-(1-benzyl-3-methyl-2-phenyl-1H-indol-6-yl)-phenoxy]-acetic acid methyl ester (0.299 g, 0.648 mmol) was reacted with 1N KOH (1.3 ml) to give the product (0.231 g, 0.511 mmol, 79%) as a white solid, mp 202-205° C. $^1$H NMR (DMSO-d$_6$) δ 2.23 (s, 3H), 4.68 (s, 2H), 5.39 (s, 2H), 6.86 (d, J=7.2 Hz, 2H), 6.96 (d, J=8.9 Hz, 2H), 7.13 (t, J=7.2 Hz, 1H), 7.18 (t, J=7.0 Hz, 2H), 7.34 (dd, J=1.4, 8.3 Hz, 1H), 7.39-7.44 (m, 3H), 7.49 (t, J=7.0 Hz, 2H), 7.56-7.61 (m, 4H); IR (solid) 3280, 2905, 1760, 1720, 1605, 1520, 1480, 1440, and 1240 cm$^{-1}$; [ESI(+)], m/z 448 (M+H)$^+$; Anal. Calcd. for $C_{30}H_{25}NO_3 \cdot 0.25H_2O$: C, 79.71; H, 5.57; N, 3.10; Found: C, 79.79; H, 5.66; N, 3.05.

Example 17

Synthesis of 1-Benzyl-3-methyl-2-phenyl-4-[4-(1H-tetrazol-5-ylmethoxy)-phenyl]-1H-indole Step 1: Synthesis of 4-Bromo-3-methyl-2-phenyl-1H-indole. The desired product was prepared using a procedure similar to step 1 of example 3. Thus, 3-bromophenylhydrazine, hydrochloride (9.857 g, 44.1 mmol) was reacted with propriophenone (5.636 g, 42 mmol) in ethanol (120 ml) to give the product (3.070 g, 10.728 mmol, 26%) as a brown oil. $^1$H NMR (DMSO-d$_6$) δ 2.54 (s, 3H), 6.93 (t, J=8.1 Hz, 1H), 7.13 (dd, J=0.9, 7.6 Hz, 1H), 7.31 (dd, J=0.9, 8.1 Hz, 1H), 7.35-7.39 (m, 1H), 7.46-7.56 (m, 4H), 11.43 (s, 1H); [ESI(−)], m/z 284/286 (M−H)$^−$.

Step 2: Synthesis of 1-Benzyl-4-bromo-3-methyl-2-phenyl-1H-indole. The desired product was prepared using a procedure similar to step 2 of example 3. Thus, 4-bromo-3-methyl-2-phenyl-1H-indole (1.467 g, 5.126 mmol) was reacted with k-t-butoxide (0.604 g, 5.383 mmol) and benzyl bromide (0.924 g, 5.383 mmol) in DMF (15 ml) to give the product (1.286 g, 3.651 mmol, 71%) as a colorless oil. $^1$H DMSO-d$_6$) δ 2.40 (s, 3H), 5.27 (s, 2H), 6.79-6.81 (m, 2H), 6.98 (t, J=7.6 Hz, 1H), 7.15-7.21 (m, 3H), 7.23 (dd, J=0.8, 7.5 Hz, 1H), 7.36-7.38 (m, 3H), 7.43-7.53 (m, 3H); [ESI(+)], m/z 376/378 (M+H)$^+$.

Step 3: Synthesis of 1-Benzyl-4-(4-methoxy-phenyl)-3-methyl-2-phenyl-1H-indole. The desired product was prepared using a procedure similar to step 3 of example 3. Thus, 1-benzyl-4-bromo-3-methyl-2-phenyl-1H-indole (1.286 g, 3.651 mmol) was reacted with aqueous 2M K$_2$CO$_3$ (3.7 ml), 4-methoxyphenylboronic acid (0.777 g, 5.111 mmol) and [1,1'-bis(diphenylphosphino)ferrocene]dichloropalladium (II) complex with dichloromethane (1:1) (0.089 g, 0.110 mmol) in dioxane (37 ml) to give the product (1.029 g, 2.550 mmol, 70%) as a white solid, mp 93-95° C. $^1$H NMR (DMSO-d$_6$) δ 1.73 (s, 3H), 3.80 (s, 3H), 5.29 (s, 2H), 6.84 (dd, J=0.8, 7.2 Hz, 1H), 6.88 (d, J=7.2 Hz, 2H), 6.97-7.00 (m, 2H), 7.11 (t, J=7.3 Hz, 1H), 7.17 (t, J=7.2 Hz, 1H), 7.22 (t, J=6.9 Hz, 2H), 7.30-7.35 (m, 5H), 7.39-7.47 (m, 3H); [ESI(+)]; m/z 404 (M+H)$^+$.

Step 4: Synthesis of 4-(1-Benzyl-3-methyl-2-phenyl-1H-indol-4-yl)-phenol. The desired product was prepared using a procedure similar to step 4 of example 3. Thus, 1-benzyl-4-(4-methoxy-phenyl)-3-methyl-2-phenyl-1H-indole (1.029 g, 2.550 mmol) was reacted with BBr$_3$ (3.1 ml of a 1M solution in CH$_2$Cl$_2$) to give the product (0.657 g, 1.687 mmol, 66%) as a white solid, mp 174-176° C. $^1$H NMR (DMSO-d$_6$) δ 1.73 (s, 3H), 5.28 (s, 2H), 6.79-6.82 (m, 3H), 6.88 (d, J=7.2 Hz, 2H), 7.07-7.10 (m, 1H), 7.15-7.19 (m, 1H), 7.20-7.23 (m, 4H), 7.28 (dd, J=0.8, 8.3 Hz, 1H), 7.32-7.34 (m, 2H), 7.39-7.47 (m, 3H), 9.41 (s, 1H); IR (solid) 3450, 3050, 1600, 1520, 1420, 1310, 1200 and 1180 cm$^{-1}$; [ESI(+)], m/z 390 (M+H)$^+$; Anal. Calcd. for $C_{28}H_{23}NO$: C, 86.34; H, 5.95; N, 3.60; Found: C, 86.13; H, 5.98; N, 3.56.

Step 5: Synthesis of [4-(1-Benzyl-3-methyl-2-phenyl-1H-indol-4-yl)-phenoxy]-acetonitrile. The desired product was prepared using a procedure similar to step 5 of example 3. Thus, 4-(1-benzyl-3-methyl-2-phenyl-1H-indol-4-yl)-phenol (0.260 g, 0.668 mmol) was reacted with K$_2$CO$_3$ (0.111 g, 0.802 mmol) and bromoacetonitrile (0.096 g, 0.802 mmol) in acetone (5 ml) to give the product (0.271 g, 0.633 mmol, 95%) as a viscous oil. $^1$H NMR (DMSO-d$_6$) δ 1.72 (s, 3H), 5.22 (s, 2H), 5.33 (s, 2H), 6.85-6.89 (m, 3H), 7.11-7.14 (m, 3H), 7.17 (t, J=7.2 Hz, 1H), 7.22 (t, J=7.0 Hz, 2H), 7.33-7.35 (m, 3H), 7.39-7.47 (m, 5H); [ESI(+)], m/z 429 (M+H)$^+$.

Step 6: Synthesis of 1-Benzyl-3-methyl-2-phenyl-4-[4-(1H-tetrazol-5-ylmethoxy)-phenyl]-1H-indole. The desired product was prepared using a procedure similar to step 6 of example 3. Thus, [4-(1-benzyl-3-methyl-2-phenyl-1H-indol-4-yl)-phenoxy]-acetonitrile (0.270 g, 0.630 mmol) was reacted with NaN$_3$ (0.205 g, 3.150 mmol) and NH$_4$Cl (0.168 g, 3.150 mmol) in DMF (5 ml) to give the product (0.211 g, 0.447 mmol, 71%) as a white solid, mp 174-177° C. $^1$H NMR (DMSO-d$_6$) δ 1.71 (s, 3H), 5.30 (s, 2H), 5.52 (s, 2H), 6.84 (d, J=7.0 Hz, 1H), 6.88 (d, J=7.0 Hz, 2H), 7.10-7.13 (m, 3H), 7.16 (t, J=7.0 Hz, 1H), 7.22 (t, J=7.0 Hz, 2H), 7.32-7.35 (m, 3H), 7.37-7.47 (m, 5H); IR (solid) 3020, 2910, 2860, 1605, 1510, 1480, 1440 and 1230 cm$^{-1}$; [ESI(−)], m/z 470 (M−H)$^−$; Anal. Calcd. for $C_{30}H_{25}N_5O$: C, 76.41; H, 5.34; N, 14.85; Found: C, 76.42; H, 5.21; N, 14.95.

Example 18

Synthesis of [4-(1-Benzyl-3-methyl-2-phenyl-1H-indol-4-yl)-phenoxy]-acetic Acid

Step 1: Synthesis of [4-(1-Benzyl-3-methyl-2-phenyl-1H-indol-4-yl)-phenoxy]-acetic acid methyl ester. The desired product was prepared using a procedure similar to step 1 of example 4. Thus, 4-(1-benzyl-3-methyl-2-phenyl-1H-indol-4-yl)-phenol (0.260 g, 0.668 mmol) was reacted with K$_2$C(O$_3$ (0.120 g, 0.868 mmol) and methyl bromoacetate (0.133 g, 0.868 mmol) in acetone (5 ml) to give the product (0.271 g, 0.587 mmol, 88%) as a viscous oil. $^1$H NMR (DMSO-d$_6$) δ 1.72 (s, 3H), 3.71 (s, 3H), 4.84 (s, 2H), 5.29 (s, 2H), 6.84 (d, J=7.0 Hz, 1H), 6.88 (d, J=7.2 Hz, 2H), 6.98 (d, J=8.7 Hz, 2H), 7.11 (t, J=7.3 Hz, 1H), 7.16 (t, J=7.2 Hz, 1H), 7.22 (t, J=7.0 Hz, 2H), 7.31-7.35 (m, 5H), 7.41 (t, J=7.2 Hz, 1H), 7.45 (t, J=7.5 Hz, 2H); [ESI(+)], m/z 462 (M+H)$^+$.

Step 2: Synthesis of [4-(1-Benzyl-3-methyl-2-phenyl-1H-indol-4-yl)-phenoxy]-acetic acid. The desired product was prepared using a procedure similar to step 2 of example 4. Thus, [4-(1-benzyl-3-methyl-2-phenyl-1H-indol-4-yl)-phenoxy]-acetic acid methyl ester (0.263 g, 0.570 mmol) was reacted with 1N KOH (1.1 ml) in THF/MeOH (3 ml/2 ml) to give the product (0.198 g, 0.442 mmol, 78%) as a white foam, mp 82-86° C. $^1$H NMR (DMSO-d$_6$) δ 1.72 (s, 3H), 4.70 (s, 2H), 5.29 (m, 2H), 6.84 (d, J=7.2 Hz, 1H), 6.88 (d, J=7.3 Hz, 2H), 6.96 (d, J=8.6 Hz, 2H), 7.11 (t, J=7.5 Hz, 1H), 7.16 (t, J=7.0 Hz, 1H), 7.22 (t, J=7.0 Hz, 2H), 7.31-7.34 (m, 5H), 7.40 (t, J=7.0 Hz, 1H), 7.45 (t, J=6.7 Hz, 2H); IR (solid) 3030, 2910, 1730, 1605, 1520, 1480, 1430, 1210, and 1180 cm$^{-1}$; [ESI(+)], m/z 448 (M+H)$^+$; Anal. Calcd. for $C_{30}H_{25}NO_3 \cdot 0.33H_2O$: C, 80.51; H, 5.63; N, 3.13; Found: C, 79.30; H, 5.78; N, 3.00.

Example 19

Synthesis of 1,3-Dimethyl-2-phenyl-4-[4-(1H-tetrazol-5-ylmethoxy)-phenyl]-1H-indole Step 1: Synthesis of 4-Bromo-1,3-dimethyl-2-phenyl-1H-indole. The desired product was prepared using a procedure similar to step 2 of example 3. Thus, 4-bromo-3-methyl-2-phenyl-1H-indole (1.574 g, 5.5 mmol) was reacted with k-t- butoxide (0.648 g, 5.775 mmol) and methyl iodide (0.820 g, 5.775 mmol) in DMF (15 ml) to give the product (1.188 g, 3.957 mmol, 72%) as a colorless oil. $^1$H DMSO-d$_6$) δ 2.39 (s, 3H), 3.55 (s, 3H), 7.05 (t, J=7.8 Hz, 1H), 7.23 (dd, J=0.8, 7.6 Hz, 1H), 7.42-7.45 (m, 2H), 7.47-7.51 (m, 2H), 7.55 (t, J=6.9 Hz, 2H); [ESI(+)], m/z 300/302 (M+H)$^+$.

Step 2: Synthesis of 4-(4-Methoxy-phenyl)-1,3-dimethyl-2-phenyl-1H-indole. The desired product was prepared using a procedure similar to step 3 of example 3. Thus, 4-bromo-1,3-dimethyl-2-phenyl-1H-indole (1.182 g, 3.937 mmol) was reacted with aqueous 2M K$_2$CO$_3$ (3.9 ml), 4-methoxyphenylboronic acid (0.838 g, 5.512 mmol) and [1,1'-bis(diphenylphosphino)ferrocene]dichloropalladium (II) complex with dichloromethane (1:1) (0.096 g, 0.118 mmol) in dioxane (39 ml) to give the product (1.253 g, 3.827 mmol, 97%) as a yellow, viscous oil. $^1$H NMR (DMSO-d$_6$) δ 1.72 (s, 3H), 3.60 (s, 3H), 3.81 (s, 3H), 6.85 (dd, J=0.8, 7.0 Hz, 1H), 6.99 (d, J=8.7 Hz, 2H), 7.20 (t, J=7.3 Hz, 1H), 7.32 (d, J=8.7 Hz, 2H), 7.41-7.47 (m, 4H), 7.53 (t, J=7.6 Hz, 2H); [ESI(+)], m/z 328 (M+H)$^+$.

Step 3: Synthesis of 4-(1,3-Dimethyl-2-phenyl-1H-indol-4-yl)-phenol. The desired product was prepared using a procedure similar to step 4 of example 3. Thus, 4-(4-methoxy-phenyl)-1,3-dimethyl-2-phenyl-1H-indole (1.227 g, 3.747 mmol) was reacted with BBr$_3$ (4.5 ml of a 1M solution in CH$_2$Cl$_2$) to give the product (0.751 g, 2.396 mmol, 64%) as a white solid, mp 132-134° C. $^1$H NMR (DMSO-d$_6$) δ 1.71 (s, 3H), 3.57 (s, 3H), 6.78-6.83 (m, 3H), 7.15-7.19 (m, 3H), 7.40-7.46 (m, 4H), 7.52 (t, J=7.2 Hz, 2H), 9.39 (s, 1H); IR (solid) 3480, 3430, 2920, 1605, 1520, 1480, 1450, 1310, 1270, and 1180 cm$^{-1}$; [ESI(+)], m/z 314 (M+H)$^+$; Anal. Calcd. for C$_{22}$H$_{19}$NO: C, 84.31; H, 6.11; N, 4.47; Found: C, 84.17; H, 6.10; N, 4.42.

Step 4: Synthesis of [4-(1,3-Dimethyl-2-phenyl-1H-indol-4-yl)-phenoxy]-acetonitrile. The desired product was prepared using a procedure similar to step 5 of example 3. Thus, 4-(1,3-dimethyl-2-phenyl-1H-indol-4-yl)-phenol (0.300 g, 0.957 mmol) was reacted with K$_2$CO$_3$ (0.159 g, 1.148 mmol) and bromoacetonitrile (0.134 g, 1.148 mmol) in acetone (5 ml) to give the product (0.311 g, 0.882 mmol, 92%) as a viscous oil. $^1$H NMR (DMSO-d$_6$) δ 1.66 (s, 3H), 3.55 (s, 3H), 5.17 (s, 2H), 6.82 (dd, J=0.9, 7.2 Hz, 1H), 7.08 (d, J=8.9 Hz, 2H), 7.16 (t, J=7.2 Hz, 1H), 7.34-7.43 (m, 6H), 7.48 (t, J=7.0 Hz, 2H); [ESI(+)], m/z 353 (M+H)$^+$.

Step 5: Synthesis of 1,3-Dimethyl-2-phenyl-4-[4-(1H-tetrazol-5-ylmethoxy)-phenyl]-1H-indole. The desired product was prepared using a procedure similar to step 6 of example 3. Thus, [4-(1,3-dimethyl-2-phenyl-1H-indol-4-yl)-phenoxy]-acetonitrile (0.311 g, 0.882 mmol) was reacted with NaN$_3$ (0.287 g, 4.412 mmol) and NH$_4$Cl (0.236 g, 4.412 mmol) in DMF (5 ml) to give the product (0.246 g, 0.622 mmol, 71%) as a white solid, dec. 208-210° C.
$^1$H NMR (DMSO-d$_6$) δ 1.69 (s, 3H), 3.58 (s, 3H), 5.52 (s, 2H), 6.85 (d, J=7.2 Hz, 1H), 7.11 (d, J=8.7 Hz, 2H), 7.19 (t, J=7.2 Hz, 1H), 7.35 (d, J=8.7 Hz, 2H), 7.40-7.46 (m, 4H), 7.52 (t, J=7.2 Hz, 2H); IR (solid) 3050, 2950, 2860, 1610, 1520, 1480, 1450 and 1230 cm$^{-1}$; [ESI(+)], m/z 396 (M+H)$^+$; Anal. Calcd. for C$_{24}$H$_{21}$N$_5$O: C, 72.89; H, 5.35; N, 17.71; Found: C, 72.85; H, 5.34; N, 17.72.

Example 20

Synthesis of [4-(1,3-Dimethyl-2-phenyl-1H-indol-4-yl)-phenoxy]-acetic Acid

Step 1: Synthesis of [4-(1,3-Dimethyl-2-phenyl-1H-indol-4-yl)-phenoxy]-acetic acid methyl ester. The desired product was prepared using a procedure similar to step 1 of example 4. Thus, 4-(1,3-dimethyl-2-phenyl-1H-indol-4-yl)-phenol (0.300 g, 0.957 mmol) was reacted with K$_2$CO$_3$ (0.172 g, 1.244 mmol) and methyl bromoacetate (0.190 g, 1.244 mmol) in acetone (5 ml) to give the product (0.287 g, 0.745 mmol, 78%) as a white solid, mp 110-112° C.
$^1$H NMR (DMSO-d$_6$) δ 1.66 (s, 3H), 3.55 (s, 3H), 3.67 (s, 3H), 4.80 (s, 2H), 6.80 (dd, J=0.9, 7.1 Hz, 1H), 6.94 (d, J=8.8 Hz, 2H), 7.15 (t, J=7.2 Hz, 1H), 7.27 (d, J=8.7 Hz, 2H), 7.36-7.43 (m, 4H), 7.46-7.50 (m, 2H); [ESI(+)], m/z 386 (M+H)$^+$.

Step 2: Synthesis of [4-(1,3-Dimethyl-2-phenyl-1H-indol-4-yl)-phenoxy]-acetic acid. The desired product was prepared using a procedure similar to step 2 of example 4. Thus, [4-(1,3-dibenzyl-2-methyl-1H-indol-5-yl)-phenoxy]-acetic acid methyl ester (0.283 g, 0.734 mmol) was reacted with 1N KOH (1.5 ml) in THF/MeOH (3 ml/2 ml) to give the product (0.139 g, 0.374 mmol, 51%) as a white solid, mp 177-180° C.
$^1$H NMR (DMSO-d$_6$) δ 1.70 (s, 3H), 3.58 (s, 3H), 4.69 (s, 2H), 6.84 (dd, J=0.8, 7.0 Hz, 1H), 6.95 (d, J=8.7 Hz, 2H), 7.17-7.20 (m, 1H), 7.31 (d, J=8.7 Hz, 2H), 7.40-7.46 (m, 4H), 7.52 (t, J=7.2 Hz, 2H); IR (solid) 3050, 2920, 2580, 1730, 1705, 1605, 1510, 1480, 1430, and 1230 cm$^{-1}$; [ESI(+)], m/z 372 (M+H)$^+$; Anal. Calcd. for C$_{24}$H$_{21}$NO$_3$: C, 77.61; H, 5.70; N, 3.77; Found: C, 77.31; H, 5.70; N, 3.72.

Example 21

Synthesis of 1-Benzyl-3-pentyl-2-phenyl-5-[4-(1H-tetrazol-5-ylmethoxy)-phenyl]-1H-indole Step 1: Synthesis of 5-Bromo-3-pentyl-2-phenyl-1H-indole. The desired product was prepared using a procedure similar to step 1 of example 3. Thus, 4-bromophenylhydrazine, hydrochloride (4.694 g, 21 mmol) was reacted with heptanophenone (3.806 g, 20 mmol) in ethanol (60 ml) to give the product (5.681 g, 16.598 mmol, 79%) as an oily solid. $^1$H NMR (DMSO-d$_6$) δ 0.79 (t, J=6.8 Hz, 3H), 1.19-1.31 (m, 4H), 1.51-1.57 (m, 2H), 2.75 (t, J=7.8 Hz, 2H), 7.15 (dd, J=2.0, 8.5 Hz, 1H), 7.26 (d, J=8.5 Hz, 1H), 7.35 (t, J=7.3 Hz, 1H), 7.47 (t, J=7.6 Hz, 2H), 7.55-7.58 (m, 2H), 7.64 (d, J=1.8 Hz, 1H), 11.29 (s, 1H); [ESI(−)], m/z 340/342 (M−H)$^-$.

Step 2: Synthesis of 1-Benzyl-5-bromo-3-pentyl-2-phenyl-1H-indole. The desired product was prepared using a procedure similar to step 2 of example 3. Thus, 5-bromo-3-pentyl-2-phenyl-1H-indole (1.711 g, 5 mmol) was reacted with k-t-butoxide (0.589 g, 5.25 mmol) and benzyl bromide (0.901 g, 5.25 mmol) in DMF (15 ml) to give the product (1.285 g, 2.972 mmol, 59%) as a white solid, mp 98-101° C.
$^1$H DMSO-d$_6$) δ 0.75 (t, J=7.0 Hz, 3H), 1.11-1.19 (m, 4H), 1.46-1.52 (m, 2H), 2.60 (t, J=7.5 Hz, 2H), 5.25 (s, 2H), 6.77-6.78 (m, 2H), 7.13-7.22 (m, 4H), 7.32 (d, J=8.7 Hz, 1H), 7.34-7.36 (m, 2H), 7.42-7.49 (m, 3H), 7.75 (d, J=1.8 Hz, 1H); [ESI(+)], m/z 432/434 (M+H)$^+$.

Step 3: Synthesis of 1-Benzyl-5-(4-methoxy-phenyl)-3-pentyl-2-phenyl-1H-indole. The desired product was prepared using a procedure similar to step 3 of example 3. Thus, 1-benzyl-5-bromo-3-pentyl-2-phenyl-1H-indole (1.282 g, 2.965 mmol) was reacted with aqueous 2M K$_2$CO$_3$ (3.0 ml), 4-methoxyphenylboronic acid (0.631 g, 4.151 mmol) and [1,1'-bis(diphenylphosphino)ferrocene]dichloropalladium (II) complex with dichloromethane (1:1) (0.073 g, 0.089 mmol) in dioxane (30 ml) to give the product (0.727 g, 1.582 mmol, 53%) as a yellow solid, mp 91-110° C. $^1$H NMR (DMSO-d$_6$) δ 0.76 (t, J=7.0 Hz, 3H), 1.15-1.21 (m, 4H), 1.54-1.59 (m, 2H), 2.68 (t, J=7.3 Hz, 2H), 3.79 (s, 3H), 5.27 (s, 2H), 6.84 (d, J=7.0 Hz, 2H), 7.01 (d, J=8.9 Hz, 2H), 7.15

(t, J=7.2 Hz, 1H), 7.20 (t, J=6.9 Hz, 2H), 7.33-7.38 (m, 4H), 7.43 (t, J=7.2 Hz, 1H), 7.48 (t, J=6.9 Hz, 2H), 7.60 (d, J=8.9 Hz, 2H), 7.75 (d, J=0.8 Hz, 1H); [ESI(+)], m/z 460 (M+H)$^+$.

Step 4: Synthesis of 4-(1-Benzyl-3-pentyl-2-phenyl-1H-indol-5-yl)-phenol. The desired product was prepared using a procedure similar to step 4 of example 3. Thus, 1-benzyl-5-(4-methoxy-phenyl)-3-pentyl-2-phenyl-1H-indole (0.708 g, 1.54 mmol) was reacted with BBr$_3$ (1.9 ml of a 1M solution in CH$_2$Cl$_2$) to give the product (0.609 g, 1.367 mmol, 89%) as a viscous oil. $^1$H NMR (DMSO-d$_6$) δ 0.76 (t, J=69 Hz, 3H), 1.13-1.22 (m, 4H), 1.53-1.59 (m, 2H), 2.67 (t, J=7.3 Hz, 2H), 5.26 (s, 2H), 6.82-6.85 (m, 4H), 7.14 (t, J=7.2 Hz, 1H), 7.19 (t, J=6.9 Hz, 2H), 7.29-7.37 (m, 4H), 7.41-7.49 (m, 5H), 7.70 (d, J=1.2 Hz, 1H), 9.37 (s, 1H); [ESI(+)], m/z 446 (M+H)$^+$;

Step 5: Synthesis of [4-(1-Benzyl-3-pentyl-2-phenyl-1H-indol-5-yl)-phenoxy]-acetonitrile. The desired product was prepared using a procedure similar to step 5 of example 3. Thus, 4-(1-benzyl-3-pentyl-2-phenyl-1H-indol-5-yl)-phenol (0.295 g, 0.662 mmol) was reacted with K$_2$CO$_3$ (0.110 g, 0.794 mmol) and bromoacetonitrile (0.095 g, 0.794 mmol) in acetone (10 ml) to give the product (0.265 g, 0.547 mmol, 83%) as a waxy solid, mp 97-99° C. $^1$H NMR (DMSO-d$_6$) δ 0.72 (t, J=7.0 Hz, 3H), 1.11-1.19 (m, 4H), 1.47-1.57 (m, 2H), 2.65 (t, J=7.6 Hz, 2H), 5.16 (s, 2H), 5.24 (s, 2H), 6.80 (d, J=6.7 Hz, 2H), 7.10-7.18 (m, 5H), 7.32-7.48 (m, 7H), 7.64 (d, J=8.9 Hz, 2H), 7.75 (s, 1H); [ESI(+)], m/z 486 (M+H)$^+$.

Step 6: Synthesis of 1-Benzyl-3-pentyl-2-phenyl-5-[4-(1H-tetrazol-5-ylmethoxy)-phenyl]-1H-indole. The desired product was prepared using a procedure similar to step 6 of example 3. Thus, [4-(1-benzyl-3-pentyl-2-phenyl-1H-indol-5-yl)-phenoxy]-acetonitrile (0.252 g, 0.520 mmol) was reacted with NaN$_3$ (0.169 g, 2.6 mmol) and NH$_4$Cl (0.139 g, 2.6 mmol) in DMF (5 ml) to give the product (0.137 g, 0.260 mmol, 50%) as a white solid, mp 165-168° C. $^1$H NMR (DMSO-d$_6$) δ 0.76 (t, J=7.0 Hz, 3H), 1.15-1.22 (m, 4H), 1.53-1.59 (m, 2H), 2.68 (t, J=7.5 Hz, 2H), 5.27 (s, 2H), 5.52 (s, 2H), 6.83 (d, J=7.2 Hz, 2H), 7.13-7.16 (m, 3H), 7.20 (t, J=6.9 Hz, 2H), 7.34-7.38 (m, 4H), 7.43 (t, J=7.0 Hz, 1H), 7.48 (t, J=6.9 Hz, 2H), 7.63 (d, J=8.6 Hz, 2H), 7.77 (S; 1H), 16.79 (broad s, 1H); IR (solid) 3030, 2920, 2850, 1605, 1520, 1480, 1260 and 1240 cm$^{-1}$; [ESI(−)], m/z 527 (M−H)$^-$; Anal. Calcd. for C$_{34}$H$_{33}$N$_5$O: C, 77.39; H, 6.30; N, 13.27; Found: C, 77.34; H, 6.33; N, 13.30.

Example 22

Synthesis of [4-(1-Benzyl-3-pentyl-2-phenyl-1H-indol-5-yl)-phenoxy]-acetic Acid

Step 1: Synthesis of [4-(1-Benzyl-3-pentyl-2-phenyl-1H-indol-5-yl)-phenoxy]-acetic acid methyl ester. The desired product was prepared using a procedure similar to step 1 of example 4. Thus, 4-(1-benzyl-3-pentyl-2-phenyl-1H-indol-5-yl)-phenol (0.300 g, 0.673 mmol) was reacted with K$_2$CO$_3$ (0.121 g, 0.875 mmol) and methyl bromoacetate (0.134 g, 0.875 mmol) in acetone (10 ml) to give the product (0.296 g, 0.572 mmol, 85%) as a white, waxy solid, mp 106-109° C. $^1$H NMR (DMSO-d$_6$) δ 0.72 (t, J=7.0 Hz, 3H), 1.09-1.19 (m, 4H), 1.49-1.56 (m, 2H), 2.64 (t, J=7.5 Hz, 2H), 3.68 (s, 3H), 4.79 (s, 2H), 5.23 (s, 2H), 6.79-6.81 (m, 2H), 6.97 (d, J=8.9 Hz, 2H), 7.09-7.18 (m, 3H), 7.29-7.34 (m, 4H), 7.37-7.47 (m, 3H), 7.55 (d, J=8.9 Hz, 2H), 7.72 (d, J=0.7 Hz, 1H); [ESI(+)], m/z 519 (M+H)$^+$.

Step 2: Synthesis of [4-(1-Benzyl-3-pentyl-2-phenyl-1H-indol-5-yl)-phenoxy]acetic acid. The desired product was prepared using a procedure similar to step 2 of example 4. Thus, [4-(1-benzyl-3-pentyl-2-phenyl-1H-indol-5-yl)-phenoxy]-acetic acid methyl ester (0.281 g, 0.543 mmol) was reacted with 1N KOH (1.1 ml) in THF/MeOH (6 ml/4 ml) to give the product (0.177 g, 0.351 mmol, 65%) as a white solid, mp 141-143° C. $^1$H NMR (DMSO-d$_6$) δ 0.76 (t, J=6.7 Hz, 3H), 1.13-1.22 (m, 4H), 1.53-1.59 (m, 2H), 2.68 (t, J=7.6 Hz, 2H), 4.69 (s, 2H), 5.27 (s, 2H), 6.84 (d, J=7.5 Hz, 2H), 6.98 (d, J=8.7 Hz, 2H), 7.14 (t, J=7.2 Hz, 1H), 7.20 (t, J=7.0 Hz, 2H), 7.33-7.38 (m, 4H), 7.43 (t, J=7.2 Hz, 1H), 7.48 (t, J=6.9 Hz, 2H), 7.59 (d, J=8.6 Hz, 2H), 7.75 (s, 1H), 13.00 (broad s, 1H); IR (solid) 3030, 2910, 2860, 1750, 1605, 1520, 1470, 1440, and 1230 cm$^{-1}$; [ESI(−)], m/z 503 (M−H)$^-$; Anal. Calcd. for C$_{34}$H$_{33}$NO$_3$.0.25H$_2$O: C, 80.37; H, 6.64; N, 2.76; Found: C, 80.55, H, 6.58; N, 2.70.

Example 23

Synthesis of 1-Methyl-3-pentyl-2-phenyl-5-[4-(1H-tetrazol-5-ylmethoxy)-phenyl]-1H-indole Step 1: Synthesis of 5-Bromo-1-methyl-3-pentyl-2-phenyl-1H-indole. The desired product was prepared using a procedure similar to step 2 of example 3. Thus, 5-bromo-3-pentyl-2-phenyl-1H-indole (1.711 g, 5.000 mmol) was reacted with k-t-butoxide (0.589 g, 5.250 mmol) and methyl iodide (0.745 g, 5.250 mmol) in DMF (15 ml) to give the product (1.113 g, 3.124 mmol, 62%) as a colorless oil. $^1$H DMSO-d$_6$) δ 0.76 (t, J=7.0 Hz, 3H), 1.13-1.18 (m, 4H), 1.44-1.50 (m, 2H), 2.58 (t, J=7.6 Hz, 2H), 3.53 (s, 3H), 7.27 (dd, J=2.0, 8.7 Hz, 1H), 7.41-7.44 (m, 3H), 7.48 (t, J=7.5 Hz, 1H), 7.54 (t, J=7.0 Hz, 2H), 7.71 (d, J=1.7 Hz, 1H); [ESI(+)], m/z 356/358 (M+H)$^+$.

Step 2: Synthesis of 5-(4-Methoxy-phenyl)-1-methyl-3-pentyl-2-phenyl-1H-indole. The desired product was prepared using a procedure similar to step 3 of example 3. Thus, 5-bromo-1-methyl-3-pentyl-2-phenyl-1H-indole (1.105 g, 3.101 mmol) was reacted with aqueous 2M K$_2$CO$_3$ (3.1 ml), 4-methoxyphenylboronic acid (0.660 g, 4.341 mmol) and [1,1'-bis(diphenylphosphino)ferrocene]dichloropalladium (II) complex with dichloromethane (1:1) (0.076 g, 0.093 mmol) in dioxane (31 ml) to give the product (0.512 g, 1.335 mmol, 43%) as an oily solid. $^1$H NMR (DMSO-d$_6$) δ 0.76 (t, J=6.9 Hz, 3H), 1.15-1.23 (m, 4H), 1.52-1.56 (m, 2H), 2.66 (t, J=7.5 Hz, 2H), 3.56 (s, 3H), 3.79 (s, 3H), 7.02 (d, J=8.7 Hz, 2H), 7.41-7.46 (m, 3H), 7.47-7.49 (m, 2H), 7.53-7.56 (m, 2H), 7.61 (d, J=8.6 Hz, 2H), 7.72 (d, J=1.5 Hz, 1H); [ESI(+)], m/z 384 (M+H)$^+$.

Step 3: Synthesis of 4-(1-Methyl-3-pentyl-2-phenyl-1H-indol-5-yl)-phenol. The desired product was prepared using a procedure similar to step 4 of example 3. Thus, 5-(4-methoxy-phenyl)-1-methyl-3-pentyl-2-phenyl-1H-indole (0.505 g, 1.317 mmol) was reacted with BBr$_3$ (1.6 ml of a 1M solution in CH$_2$Cl$_2$) to give the product (0.375 g, 1.023 mmol, 78%) as a light-brown oil. $^1$H NMR (DMSO-d$_6$) δ 0.76 (t, J=7.0 Hz, 3H), 1.14-1.22 (m, 4H), 1.51-1.57 (m, 2H), 2.65 (t, J=7.5 Hz, 2H), 3.55 (s, 3H), 6.84 (d, J=8.6 Hz, 2H), 7.39 (dd, J=1.7, 8.4 Hz, 1H), 7.43-7.50 (m, 6H), 7.54 (t, J=7.2 Hz, 2H), 7.68 (d, J=1.5 Hz, 1H), 9.37 (s, 1H); [ESI(+)], m/z 370 (M+H)$^+$.

Step 4: Synthesis of [4-(1-Methyl-3-pentyl-2-phenyl-1H-indol-5-yl)-phenoxy]-acetonitrile. The desired product was prepared using a procedure similar to step 5 of example 3. Thus, 4-(1-methyl-3-pentyl-2-phenyl-1H-indol-5-yl)-phenol (0.173 g, 0.472 mmol) was reacted with K$_2$CO$_3$ (0.078 g, 0.566 mmol) and bromoacetonitrile (0.068 g, 0.566 mmol) in acetone (10 ml) to give the product (0.160 g, 0.392 mmol, 83%) as a white solid, mp 101-102° C. $^1$H NMR (DMSO-d$_6$) δ 0.76 (t, J=7.0 Hz, 3H), 1.14-1.22 (m, 4H), 1.52-1.98 (m, 2H), 2.66 (t, J=7.5 Hz, 2H), 3.56 (s, 3H), 5.21 (s, 2H), 7.16 (d, J=8.9 Hz, 2H), 7.43-7.51 (m, 5H), 7.55 (t, J=7.2 Hz, 2H), 7.69 (d, J=8.9 Hz, 2H), 7.76 (d, J=1.1 Hz, 1H); [ESI(+)], m/z 409 (M+H)$^+$.

Step 5: Synthesis of 1-Methyl-3-pentyl-2-phenyl-5-[4-(1H-tetrazol-5-ylmethoxy)-phenyl]-1H-indole. The desired product was prepared using a procedure similar to step 6 of example 3. Thus, [4-(1-methyl-3-pentyl-2-phenyl-1H-indol-5-yl)-phenoxy]-acetonitrile (0.152 g, 0.372 mmol) was reacted with NaN$_3$ (0.121 g, 1.860 mmol) and NH$_4$Cl (0.099 g, 1.860 mmol) in DMF (5 ml) to give the product (0.117 g, 0.259 mmol, 70%) as a white solid, dec. 181-185° C. $^1$H NMR (DMSO-d$_6$) δ 0.76 (t, J=7.0 Hz, 3H), 1.13-1.22 (m, 4H), 1.51-1.57 (m, 2H), 2.66 (t, J=7.5 Hz, 2H), 3.56 (s, 3H), 5.53 (s, 2H), 7.15 (d, J=8.7 Hz, 2H), 7.42-7.45 (m, 3H), 7.48 (t, J=8.6 Hz, 2H), 7.54 (t, J=7.2 Hz, 2H), 7.65 (d, J=8.7 Hz, 2H), 7.74 (d, J=1.2 Hz, 1H), 16.80 (broad s, 1H); IR (solid) 3030, 2930, 2860, 1605, 1520, 1480, 1370 and 1240 cm$^{-1}$; [ESI(−)], m/z 450 (M−H)$^-$; Anal. Calcd. for C$_{28}$H$_{29}$N$_5$O: C, 74.48; H, 6.47; N, 15.51 Found: C, 74.49; H, 6.26; N, 15.30.

Example 24

Synthesis of [4-(1-Methyl-3-pentyl-2-phenyl-1H-indol-5-yl)-phenoxy]-acetic Acid

Step 1: Synthesis of [4-(1-Methyl-3-pentyl-2-phenyl-1H-indol-5-yl)-phenoxy]-acetic acid methyl ester. The desired product was prepared using a procedure similar to step 1 of example 4. Thus, 4-(1-methyl-3-pentyl-2-phenyl-1H-indol-5-yl)-phenol (0.180 g, 0.491 mmol) was reacted with K$_2$CO$_3$ (0.088 g, 0.639 mmol) and methyl bromoacetate (0.098 g, 0.639 mmol) in acetone (5 ml) to give the product (0.184 g, 0.417 mmol, 85%) as a viscous oil. $^1$H NMR (DMSO-d$_6$) δ 0.76 (t, J=7.2 Hz, 3H), 1.15-1.22 (m, 4H), 1.51-1.56 (m, 2H), 2.65 (t, J=7.3 Hz, 2H), 3.56 (s, 3H), 3.71 (s, 3H), 4.83 (s, 2H), 7.01 (d, J=8.6 Hz, 2H), 7.41-7.45 (m, 3H), 7.47-7.50 (m, 2H), 7.54 (t, J=7.2 Hz, 2H), 7.61 (d, J=8.6 Hz, 2H), 7.73 (s, 1H); [ESI(+)], m/z 442 (M+H)$^+$.

Step 2: Synthesis of [4-(1-Methyl-3-pentyl-2-phenyl-1H-indol-5-yl)-phenoxy]-acetic acid. The desired product was prepared using a procedure similar to step 2 of example 4. Thus, [4-(1-methyl-3-pentyl-2-phenyl-1H-indol-5-yl)-phenoxy]-acetic acid methyl ester (0.184 g, 0.417 mmol) was reacted with 1N KOH (1.0 ml) in THF/MeOH (3 ml/2 ml) to give the product (0.104 g, 0.243 mmol, 58%) as a white solid, mp 146-148° C. $^1$H NMR (DMSO-d$_6$) δ 0.73 (t, J=6.8 Hz, 3H), 1.10-1.19 (m, 4H), 1.47-1.54 (m, 2H), 2.62 (t, J=7.4 Hz, 2H), 3.52 (s, 3H), 4.66 (s, 2H), 6.96 (d, J=8.9 Hz, 2H), 7.37-7.46 (m, 5H), 7.51 (t, J=7.0 Hz, 2H), 7.57 (d, J=8.9 Hz, 2H), 7.69 (d, J=1.1 Hz, 1H), 12.96 (broad s, 1H); IR (solid) 3040, 2920, 2860, 1730, 1705, 1605, 1520, 1480, 1430, 1370, and 1230 cm$^{-1}$; [ESI(−)], m/z 427 (M−H)$^-$; Anal. Calcd. for C$_{28}$H$_{29}$NO$_3$.0.25H$_2$O: C, 77.84; H, 6.77; N, 3.24; Found: C, 78.13; H, 6.60; N, 3.19.

Example 25

Synthesis of 1,3-Dibenzyl-2-phenyl-5-[4-(1H-tetrazol-5-ylmethoxy)-phenyl]-1H-indole Step 1: Synthesis of 3-Benzyl-5-bromo-2-phenyl-1H-indole. The desired product was prepared using a procedure similar to step 1 of example 3. Thus, 4-bromophenylhydrazine, hydrochloride (5.867 g, 26.25 mmol) was reacted with β-phenylpropriophenone (5.257 g, 25 mmol) in ethanol (60 ml) to give the product (3.800 g, 10.489 mmol, 42%) as an off-white solid, mp 124-126° C. $^1$H NMR (DMSO-d$_6$) δ 4.17 (s, 2H), 7.09-7.22 (m, 6H), 7.30-7.36 (m, 2H), 7.42-7.46 (m, 3H), 7.54-7.58 (m, 2H), 11.49 (s, 1H); [ESI(−)], m/z 360/362 (M−H)$^-$.

Step 2: Synthesis of 1,3-Dibenzyl-5-bromo-2-phenyl-1H-indole. The desired product was prepared using a procedure similar to step 2 of example 3. Thus, 3-benzyl-5-bromo-2-phenyl-1H-indole (1.811 g, 5 mmol) was reacted with k-t-butoxide (0.589 g, 5.25 mmol) and benzyl bromide (0.901 g, 5.25 mmol) in DMF (20 ml) to give the product (1.932 g, 4.271 mmol, 85%) as a white solid, mp 155-157° C. $^1$H NMR (DMSO-d$_6$) δ 3.99 (s, 2H), 5.32 (s, 2H), 6.82 (d, J=7.2 Hz, 2H), 7.07 (d, J=7.3 Hz, 2H), 7.09-7.23 (m, 7H), 7.34-7.39 (m, 3H), 7.43-7.49 (m, 3H), 7.53 (d, J=1.8 Hz, 1H); [ESI(+)], m/z 453/455 (M+H)$^+$.

Step 3: Synthesis of 1,3-Dibenzyl-5-(4-methoxy-phenyl)-2-phenyl-1H-indole. The desired product was prepared using a procedure similar to step 3 of example 3. Thus, 1,3-dibenzyl-5-bromo-2-phenyl-1H-indole (1.932 g, 4.271 mmol) was reacted with aqueous 2M K$_2$CO$_3$ (4.3 ml), 4-methoxyphenylboronic acid (0.909 g, 5.979 mmol) and [1,1'-bis(diphenylphosphino)ferrocene]dichloropalladium (II) complex with dichloromethane (1:1) (0.105 g, 0.128 mmol) in dioxane (43 ml) to give the product (1.163 g, 2.425 mmol, 57%) as a brown, viscous oil. $^1$H NMR (DMSO-d$_6$) δ 3.76 (s, 3H), 4.06 (s, 2H), 5.34 (s, 2H), 6.87 (d, J=7.6 Hz, 2H), 6.97 (d, J=8.8 Hz, 2H), 7.09-7.23 (m, 8H), 7.34 (dd, J=1.7, 8.6 Hz, 1H), 7.39-7.49 (m, 8H), 7.56 (s, 1H); [ESI(+)], m/z 480 (M+H)$^+$.

Step 4: Synthesis of 4-(1,3-Dibenzyl-2-phenyl-1H-indol-5-yl)-phenol. The desired product was prepared using a procedure similar to step 4 of example 3. Thus, 1,3-dibenzyl-5-(4-methoxy-phenyl)-2-phenyl-1H-indole (1.162 g, 2.423 mmol) was reacted with BBr$_3$ (2.9 ml of a 1M solution in CH$_2$Cl$_2$) to give the product (1.105 g, 2.373 mmol, 98%) as a brown oil. $^1$H NMR (DMSO-d$_6$) δ 4.05 (s, 2H), 5.33 (s, 2H), 6.79 (d, J=8.6 Hz, 2H), 6.87 (d, J=7.5 Hz, 2H), 7.08-7.23 (m, 8H), 7.30 (d, J=8.4 Hz, 1H), 7.35-7.40 (m, 5H), 7.42-7.49 (m, 3H), 7.52 (s, 1H), 9.36 (s, 1H); [ESI(+)], m/z 466 (M+H)$^+$.

Step 5: Synthesis of [4-(1,3-Dibenzyl-2-phenyl-1H-indol-5-yl)-phenoxy]-acetonitrile. The desired product was prepared using a procedure similar to step 5 of example 3. Thus, 4-(1,3-dibenzyl-2-phenyl-1H-indol-5-yl)-phenol (0.542 g, 1.163 mmol) was reacted with K$_2$CO$_3$ (0.225 g, 1.628 mmol) and bromoacetonitrile (0.195 g, 1.628 mmol) in acetone (10 ml) to give the product (0.486 g, 0.963 mmol, 83%) as a viscous, yellow oil. $^1$H NMR (DMSO-d$_6$) δ 4.08 (s, 2H), 5.19 (s, 2H), 5.36 (s, 2H), 6.89 (d, J=7.3 Hz, 2H), 7.10-7.24 (m, 10H), 7.37-7.51 (m, 7H), 7.57 (d, J=8.9 Hz, 2H), 7.63 (s, 1H); [ESI(+)], m/z 505 (M+H)$^+$.

Step 6: Synthesis of 1,3-Dibenzyl-2-phenyl-5-[4-(1H-tetrazol-5-ylmethoxy)-phenyl]-1H-indole. The desired product was prepared using a procedure similar to step 6 of example 3. Thus, [4-(1,3-dibenzyl-2-phenyl-1H-indol-5-yl)-phenoxy]-acetonitrile (0.481 g, 0.953 mmol) was reacted with NaN$_3$ (0.310 g, 4.766 mmol) and NH$_4$Cl (0.255 g, 4.766 mmol) in DMF (5 ml) to give the product (0.394 g, 0.719 mmol, 75%) as an off-white solid, dec. 191-194° C. $^1$H NMR (DMSO-d$_6$) δ 4.08 (s, 2H), 5.35 (s, 2H), 5.51 (s, 2H), 6.89 (d, J=7.2 Hz, 2H), 7.10-7.25 (m, 10H), 7.37 (dd, J=1.7, 8.5 Hz, 1H), 7.40-7.54 (m, 8H), 7.61 (s, 1H), 16.80 (broad s, 1H); IR (solid) 3020, 2920, 1605, 1520, 1470, 1450, 1360, and 1240 cm$^{-1}$; [ESI(−)], m/z 546 (M−H)$^-$; Anal. Calcd. for C$_{36}$H$_{29}$N$_5$O: C, 78.95; H, 5.34; N, 12.79; Found: C, 78.53H, 5.25; N, 12.77.

Example 26

Synthesis of [4-(1,3-Dibenzyl-2-phenyl-1H-indol-5-yl)-phenoxy]-acetic Acid

Step 1: Synthesis of [4-(1,3-Dibenzyl-2-phenyl-1H-indol-5-yl)-phenoxy]-acetic acid methyl ester. The desired product was prepared using a procedure similar to step 1 of example 4. Thus, 4-(1,3-dibenzyl-2-phenyl-1H-indol-5-yl)-phenol (0.541 g, 1.163 mmol) was reacted with K$_2$CO$_3$ (0.225 g, 1.628 mmol) and methyl bromoacetate (0.249 g, 1.628 mmol) in acetone (10 ml) to give the product (0.525 g, 0.976 mmol, 84%) as a solid. $^1$H NMR (DMSO-d$_6$) δ 3.66 (s, 3H), 4.03 (s, 2H), 4.77 (s, 2H), 5.30 (s, 2H), 6.84 (d, J=6.8 Hz, 2H), 6.93 (d, J=8.8 Hz, 2H), 7.04-7.20 (m, 8H), 7.30 (dd, J=1.7, 8.5 Hz, 1H), 7.35-7.47 (m, 8H), 7.54 (d, J=1.2 Hz, 1H); [ESI(+)], m/z 538 (M+H)$^+$.

Step 2: Synthesis of [4-(1,3-Dibenzyl-2-phenyl-1H-indol-5-yl)-phenoxy]-acetic acid. The desired product was prepared using a procedure similar to step 2 of example 4. Thus, [4-(1,3-dibenzyl-2-phenyl-1H-indol-5-yl)-phenoxy]-acetic acid methyl ester (0.491 g, 0.913 mmol) was reacted with 1N KOH (1.8 ml) in THF/MeOH (6 ml/4 ml) to give the product (0.376 g, 0.713 mmol, 78%) as a white solid, mp 153-155° C. $^1$H NMR (DMSO-d$_6$) δ 4.08 (s, 2H), 4.68 (s, 2H), 5.35 (s, 2H), 6.89 (d, J=7.2 Hz, 2H), 6.96 (d, J=8.9 Hz, 2H), 7.10-7.25 (m, 8H), 7.35 (dd, J=1.7, 8.5 Hz, 1H), 7.41-7.51 (m, 8H), 7.59 (d, J=1.1 Hz, 1H), 12.95 (broad s, 1H); IR (solid) 3020, 2900, 1750, 1600, 1520, 1470, 1450, 1430, 1350, and 1220 cm$^{-1}$; [ESI(+)], m/z 524 (M+H)$^+$; Anal. Calcd. for C$_{36}$H$_{29}$NO$_3$·0.20H$_2$O: C, 82.01; H, 5.62; N, 2.66; Found: C, 82.08, H, 5.58; N, 2.55.

Example 27

Synthesis of 3-Benzyl-1-methyl-2-phenyl-5-[4-(1H-tetrazol-5-ylmethoxy)-phenyl]-1H-indole Step 1: Synthesis of 3-Benzyl-5-bromo-1-methyl-2-phenyl-1H-indole. The desired product was prepared using a procedure similar to step 2 of example 3. Thus, 3-benzyl-5-bromo-2-phenyl-1H-indole (1.811 g, 5 mmol) was reacted with k-t-butoxide (0.589 g, 5.25 mmol) and methyl iodide (0.745 g, 5.25 mmol) in DMF (20 ml) to give the product (1.537 g, 4.085 mmol, 82%) as a white solid, mp 141-145° C. $^1$H DMSO-d$_6$) δ 3.56 (s, 3H), 3.93 (s, 2H), 7.02 (d, J=6.8 Hz, 2H), 7.07 (t, J=7.3 Hz, 1H), 7.15 (t, J=7.2 Hz, 2H), 7.23 (dd, J=2.0, 8.7 Hz, 1H), 7.40-7.52 (m, 7H); [ESI(+)], m/z 377/379 (M+H)$^+$.

Step 2: Synthesis of 3-Benzyl-5-(4-methoxy-phenyl)-1-methyl-2-phenyl-1H-indole. The desired product was prepared using a procedure similar to step 3 of example 3. Thus, 3-benzyl-5-bromo-1-methyl-2-phenyl-1H-indole (1.525 g, 4.053 mmol) was reacted with aqueous 2M K$_2$CO$_3$ (4.1 ml), 4-methoxyphenylboronic acid (0.862 g, 5.674 mmol) [1,1'-bis(diphenylphosphino)ferrocene]dichloropalladium (II) complex with dichloromethane (1:1) (0.099 g, 0.122 mmol) in dioxane (41 ml) to give the product (0.766 g, 1.898 mmol, 47%) as an off-white solid, mp 122-125° C. $^1$H NMR (DMSO-d$_6$) δ 3.62 (s, 3H), 3.77 (s, 3H), 4.04 (s, 2H), 6.98 (d, J=8.6 Hz, 2H), 7.07-7.11 (m, 3H), 7.18 (t, J=7.8 Hz, 2H), 7.42 (dd, J=1.5, 8.6 Hz, 1H), 7.45-7.55 (m, 9H); [ESI(+)], m/z 405 (M+H)$^+$.

Step 3: Synthesis of 4-(3-Benzyl-1-methyl-2-phenyl-1H-indol-5-yl)-phenol. The desired product was prepared using a procedure similar to step 4 of example 3. Thus, 3-benzyl-5-(4-methoxy-phenyl)-1-methyl-2-phenyl-1H-indole (0.757 g, 1.876 mmol) was reacted with BBr$_3$ (2.3 ml of a 1M solution in CH$_2$Cl$_2$) to give the product (0.371 g, 0.953 mmol, 51%) as a solid, mp 133-135° C. $^1$H NMR (DMSO-d$_6$) δ 3.61 (s, 3H), 4.03 (s, 2H), 6.80 (d, J=8.6 Hz, 2H), 7.07-7.10 (m, 3H), 7.18 (t, J=7.9 Hz, 2H), 7.38-7.39 (m, 3H), 7.44-7.55 (m, 7H), 9.36 (s, 1H); IR (solid) 3290, 3020, 1605, 1520, 1480, 1430, 1370, and 1230 cm$^{-1}$; [ESI(+)], m/z 390 (M+H)$^+$; Anal. Calcd. for C$_{28}$H$_{23}$NO·0.25H$_2$O: C, 85.36; H, 6.01; N, 3.55; Found: C, 85.52, H, 5.94; N, 3.32.

Step 4: Synthesis of [4-(3-Benzyl-1-methyl-2-phenyl-1H-indol-5-yl)-phenoxy]-acetonitrile. The desired product was prepared using a procedure similar to step 5 of example 3. Thus, 4-(3-benzyl-1-methyl-2-phenyl-1H-indol-5-yl)-phenol (0.140 g, 0.359 mmol) was reacted with K$_2$CO$_3$ (0.065 g, 0.467 mmol) and bromoacetonitrile (0.056 g, 0.467 mmol) in acetone (5 ml) to give the product (0.141 g, 0.329 mmol, 92%) as a glass-like solid. $^1$H NMR (DMSO-d$_6$) δ 3.62 (s, 3H), 4.04 (s, 2H), 5.18 (s, 2H), 7.07-7.13 (m, 5H), 7.18 (t, J=7.5 Hz, 2H), 7.44-7.49 (m, 4H), 7.52-7.55 (m, 3H), 7.57-7.60 (m, 3H); [ESI(+)], m/z 429 (M+H)$^+$.

Step 5: Synthesis of 3-Benzyl-1-methyl-2-phenyl-5-[4-(1H-tetrazol-5-ylmethoxy)-phenyl]-1H-indole. The desired product was prepared using a procedure similar to step 6 of example 3. Thus, [4-(3-benzyl-1-methyl-2-phenyl-1H-indol-5-yl)-phenoxy]-acetonitrile (0.137 g, 0.320 mmol) was reacted with NaN$_3$ (0.104 g, 1.598 mmol) and NH$_4$Cl (0.085 g, 1.598 mmol) in DMF (5 ml) to give the product (0.102 g, 0.216 mmol, 68%) as a pale-yellow solid, dec. 194-197° C. $^1$H NMR (DMSO-d$_6$) δ 3.59 (s, 3H), 4.01 (s, 2H), 5.46 (s, 2H), 7.03-7.09 (m, 5H), 7.13-7.17 (m, 2H), 7.39-7.53 (m, 9H), 7.55 (d, J=1.2 Hz, 1H), 16.75 (broad s, 1H); IR (solid) 3020, 2920, 1605, 1520, 1480, 1450, 1370 and 1240 cm$^{-1}$; [ESI(−)], m/z 470 (M−H)$^-$; Anal. Calcd. for C$_{30}$H$_{25}$N$_5$O: C, 76.41; H, 5.34; N, 14.85; Found: C, 76.35; H, 5.28; N, 14.90.

Example 28

Synthesis of [4-(3-Benzyl-1-methyl-2-phenyl-1H-indol-5-yl)-phenoxy]-acetic Acid

Step 1: Synthesis of [4-(3-Benzyl-1-methyl-2-phenyl-1H-indol-5-yl)-phenoxy]-acetic acid methyl ester. The desired product was prepared using a procedure similar to step 1 of example 4. Thus, 4-(3-benzyl-1-methyl-2-phenyl-1H-indol-5-yl)-phenol (0.140 g, 0.359 mmol) was reacted with K$_2$CO$_3$ (0.065 g, 0.467 mmol) and methyl bromoacetate (0.071 g, 0.467 mmol) in acetone (5 ml) to give the product (0.141 g, 0.305 mmol, 85%) as a glass-like solid. $^1$H NMR (DMSO-d$_6$) δ 3.62 (s, 3H), 3.70 (s, 3H), 4.04 (s, 2H), 4.81 (s, 2H), 6.97 (d, J=8.9 Hz, 2H), 7.07-7.11 (m, 3H), 7.18 (t, J=7.6 Hz, 2H), 7.41-7.57 (m, 10H); [ESI(+)], m/z 462 (M+H)$^+$.

Step 2: Synthesis of [4-(3-Benzyl-1-methyl-2-phenyl-1H-indol-5-yl)-phenoxy]-acetic acid. The desired product was prepared using a procedure similar to step 2 of example 4. Thus, [4-(3-benzyl-1-methyl-2-phenyl-1H-indol-5-yl)-phenoxy]-acetic acid methyl ester (0.139 g, 0.301 mmol) was reacted with 1N KOH (0.6 ml) in THF/MeOH (3 ml/2 ml) to give the product (0.075 g, 0.168 mmol, 56%) as a white solid, mp 179-181° C. $^1$H NMR (DMSO-d$_6$) δ 3.63 (s, 3H), 4.05 (s, 2H), 4.69 (s, 2H), 6.97 (d, J=8.9 Hz, 2H), 7.08-7.12 (m, 3H), 7.19 (t, J=7.6 Hz, 2H), 7.43 (dd, J=1.5, 8.4 Hz, 1H), 7.46-7.58 (m, 9H); IR (solid) 3020, 2910, 1730, 1705, 1605, 1510, 1480, 1430, 1370, 1270, and 1230 cm$^{-1}$; [ESI(+)], m/z 448

(M+H)⁺; Anal. Calcd. for $C_{30}H_{25}NO_3$: C, 80.51; H, 5.63; N, 3.13; Found: C, 80.15; H, 5.62; N, 3.11.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

All publications and patent documents cited above are hereby incorporated by reference in their entirety for all purposes to the same extent as if each were so individually denoted.

What is claimed:

1. A compound of the formula:

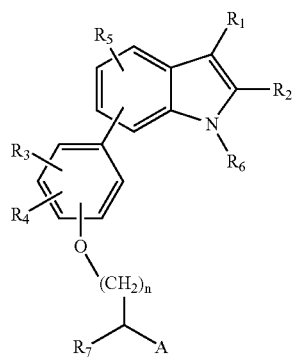

or a pharmaceutically acceptable salt or ester form thereof, wherein $R_1$ is $C_1$-$C_6$ alkyl, $C_1$-$C_6$ perfluoroalkyl, $C_3$-$C_8$ cycloalkyl, aryl, or arylalkyl;

$R_2$ is $C_1$-$C_6$ alkyl, $C_1$-$C_6$ perfluoroalkyl, $C_3$-$C_8$ cycloalkyl, aryl, or arylalkyl;

or $R_1$ and $R_2$ form a $C_5$-$C_8$ carbocyclic ring;

$R_3$, $R_4$ and $R_5$ are, independently, hydrogen, $C_1$-$C_6$ alkyl, $C_3$-$C_8$ cycloalkyl, halogen, hydroxy, $C_6$-$C_{14}$ aryl, $C_1$-$C_3$ perfluoroalkyl, $C_1$-$C_3$ alkoxy, or $C_1$-$C_3$ perfluoroalkoxy;

$R_6$ is hydrogen, $C_1$-$C_6$ alkyl, $C_1$-$C_6$ arylalkyl, $C_1$-$C_6$ alkanoyl, or aroyl;

$R_7$ is hydrogen;

n is an integer of 0-6; and

A is COOH, or an acid mimic.

2. A compound of claim 1, wherein $R_2$ is aryl or $R_1$ and $R_2$ form a $C_5$-$C_8$ carbocyclic ring; or a pharmaceutically acceptable salt or ester form thereof.

3. A compound of claim 2, of the formula:

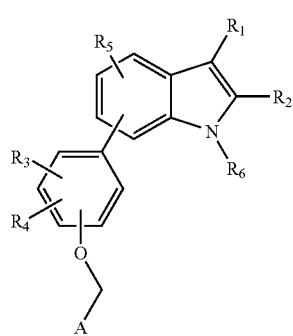

or a pharmaceutically acceptable salt or ester form thereof, wherein A is COOH or tetrazole.

4. A compound of the formula:

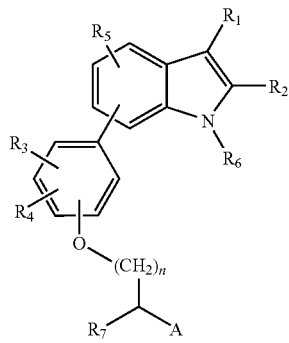

or a pharmaceutically acceptable salt or ester form thereof, wherein:

$R_1$ is, independently, $C_3$-$C_8$ cycloalkyl, and $R_2$ is, independently, hydrogen, $C_1$-$C_6$ alkyl, $C_1$-$C_6$ perfluoroalkyl, $C_3$-$C_8$ cycloalkyl, $C_6$-$C_{14}$ aryl, or arylalkyl;

or $R_1$ is, independently, hydrogen, $C_1$-$C_6$ alkyl, $C_1$-$C_6$ perfluoroalkyl, $C_3$-$C_8$ cycloalkyl, $C_6$-$C_{14}$ aryl, or arylalkyl and $R_2$ is, independently, $C_1$-$C_6$ perfluoroalkyl, or $C_3$-$C_8$ cycloalkyl;

or $R_1$ is, independently, $C_1$-$C_6$ perfluoroalkyl, $C_3$-$C_8$ cycloalkyl, or unsubstituted aryl, and $R_2$ is, independently, $C_1$-$C_6$ perfluoroalkyl, $C_3$-$C_8$ cycloalkyl, or unsubstituted aryl;

or $R_1$ and $R_2$ form a $C_5$-$C_8$ carbocyclic ring;

$R_3$, $R_4$ and $R_5$ are, independently, hydrogen, $C_1$-$C_6$ alkyl, $C_3$-$C_8$ cycloalkyl, halogen, hydroxy, $C_6$-$C_{14}$ aryl, $C_1$-$C_3$ perfluoroalkyl, $C_1$-$C_3$ alkoxy, or $C_1$-$C_3$ perfluoroalkoxy;

$R_6$ is hydrogen, $C_1$-$C_6$ alkyl, $C_1$-$C_6$ arylalkyl, $C_1$-$C_6$ alkanoyl, or aroyl;

$R_7$ is hydrogen;

n is an integer of 0-6; and

A is OOOH or an acid mimic.

5. The compound of claim 4, wherein A is COOH or tetrazole; or a pharmaceutically acceptable salt or ester form thereof.

6. A compound of the formula:

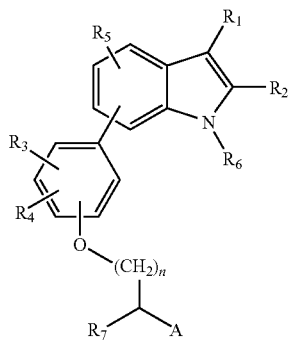

or a pharmaceutically acceptable salt or ester form thereof, wherein:

$R_1$ is $C_1$-$C_6$ perfluoroalkyl or $C_3$-$C_8$ cycloalkyl, and $R_2$ is $C_1$-$C_6$ alkyl, $C_1$-$C_6$ perfluoroalkyl, $C_3$-$C_8$ cycloalkyl, $C_6$-$C_{14}$ aryl, or arylalkyl;

or $R_1$ is $C_1$-$C_6$ alkyl, $C_1$-$C_6$ perfluoroalkyl, $C_3$-$C_8$ cycloalkyl, $C_6$-$C_{14}$ aryl, or arylalkyl and $R_2$ is $C_1$-$C_6$ perfluoroalkyl or $C_3$-$C_8$ cycloalkyl;

or $R_1$ and $R_2$ are hydrogen;

or $R_1$ and $R_2$ form a $C_5$-$C_8$ carbocyclic ring;

$R_3$, $R_4$ and $R_5$ are, independently, hydrogen, $C_1$-$C_6$ alkyl, $C_3$-$C_8$ cycloalkyl, halogen, hydroxy, $C_6$-$C_{14}$ aryl, $C_1$-$C_3$ perfluoroalkyl, $C_1$-$C_3$ alkoxy, or $C_1$-$C_3$ perfluoroalkoxy;

$R_6$ is hydrogen, $C_1$-$C_6$ alkyl, $C_1$-$C_6$ arylalkyl, $C_1$-$C_6$ alkanoyl, or aroyl;

$R_7$ is hydrogen;

n is an integer of 0-6; and

A is OOOH, or an acid mimic.

7. The compound of claim 6, wherein $R_6$ is $C_1$-$C_6$ alkanoyl or aroyl; or a pharmaceutically acceptable salt or ester form thereof.

8. A compound of the formula:

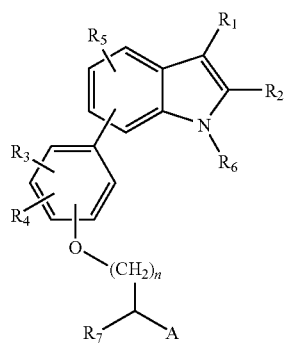

or a pharmaceutically acceptable salt or ester form thereof, wherein:

$R_1$ is, independently, $C_1$-$C_6$ perfluoroalkyl, $C_3$-$C_8$ cycloalkyl, $C_6$-$C_{14}$ aryl, or arylalkyl and $R_2$ is, independently, hydrogen, $C_1$-$C_6$ alkyl, $C_1$-$C_6$ perfluoroalkyl, $C_3$-$C_8$ cycloalkyl, $C_6$-$C_{14}$ aryl, or arylalkyl;

or $R_1$ is, independently, $C_1$-$C_6$ alkyl, $C_1$-$C_6$ perfluoroalkyl, $C_3$-$C_8$ cycloalkyl, arylalkyl, or aryl, and $R_2$ is, independently, hydrogen, $C_1$-$C_6$ perfluoroalkyl, $C_3$-$C_8$ cycloalkyl, or aryl;

or $R_1$ and $R_2$ form a $C_5$-$C_8$ carbocyclic ring;

$R_3$, $R_4$ and $R_5$ are, independently, hydrogen, $C_1$-$C_6$ alkyl, $C_3$-$C_8$ cycloalkyl, halogen, hydroxy, $C_6$-$C_{14}$ aryl, $C_1$-$C_3$ perfluoroalkyl, $C_1$-$C_3$ alkoxy, or $C_1$-$C_3$ perfluoroalkoxy;

$R_6$ is hydrogen, $C_1$-$C_6$ alkyl, $C_1$-$C_6$ arylalkyl, $C_1$-$C_6$ alkanoyl, or aroyl;

$R_7$ is hydrogen;

n is an integer of 0-6; and

A is an acid mimic.

9. A compound of claim 8, wherein $R_1$ is, independently, $C_1$-$C_6$ alkyl, $C_1$-$C_6$ perfluoroalkyl, $C_3$-$C_8$ cycloalkyl, arylalkyl, or aryl and $R_2$ is, independently, $C_1$-$C_6$ perfluoroalkyl, $C_3$-$C_8$ cycloalkyl, or unsubstituted aryl; or $R_1$ and $R_2$ together form a $C_5$-$C_8$ carbocyclic ring; or a pharmaceutically acceptable salt or ester form thereof.

10. A compound of claim 1, of the formula:

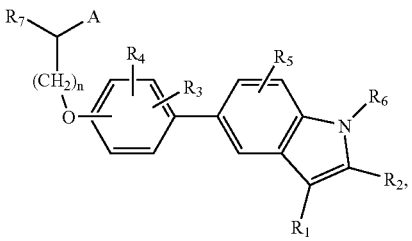

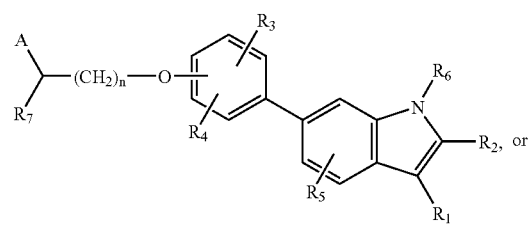

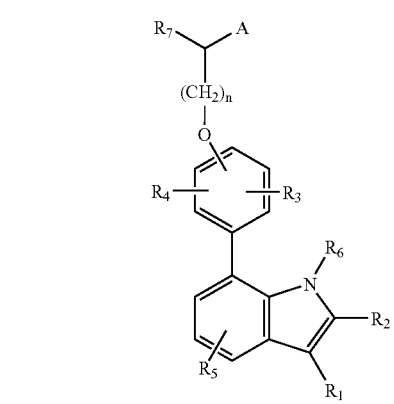

or a pharmaceutically acceptable salt or ester form thereof, wherein:

$R_1$ is $C_1$-$C_6$ alkyl, $C_1$-$C_6$ perfluoroalkyl, $C_3$-$C_8$ cycloalkyl, $C_6$-$C_{14}$ aryl, or arylalkyl;

$R_2$ is $C_1$-$C_6$ alkyl, $C_1$-$C_6$ perfluoroalkyl, $C_3$-$C_8$ cycloalkyl, $C_6$-$C_{14}$ aryl, or arylalkyl;

or $R_1$ and $R_2$ together form a $C_5$-$C_8$ carbocyclic ring;

$R_3$, $R_4$ and $R_5$ are, independently, hydrogen, $C_1$-$C_6$ alkyl, $C_3$-$C_8$ cycloalkyl, halogen, hydroxy, $C_6$-$C_{14}$ aryl, $C_1$-$C_3$ perfluoroalkyl, $C_1$-$C_3$ alkoxy, or $C_1$-$C_3$ perfluoroalkoxy;

$R_6$ is hydrogen, $C_1$-$C_6$ alkyl, $C_1$-$C_6$ arylalkyl, $C_1$-$C_6$ alkanoyl, or aroyl;

$R_7$ is hydrogen;

n is an integer of 0-6; and

A is an acid mimic.

11. The compound of claim 10, wherein $R_6$ is $C_1$-$C_6$ alkanoyl, or aroyl;

or a pharmaceutically acceptable salt or ester form thereof.

12. The compound of claim 10, wherein $R_2$ is $C_1$-$C_6$ perfluoroalkyl, $C_3$ $C_8$ cycloalkyl, or unsubstituted aryl, or $R_1$ and $R_2$ together form a $C_5$-$C_8$ carbocyclic ring; or a pharmaceutically acceptable salt or ester form thereof.

13. A compound of claim 1, of the formula:

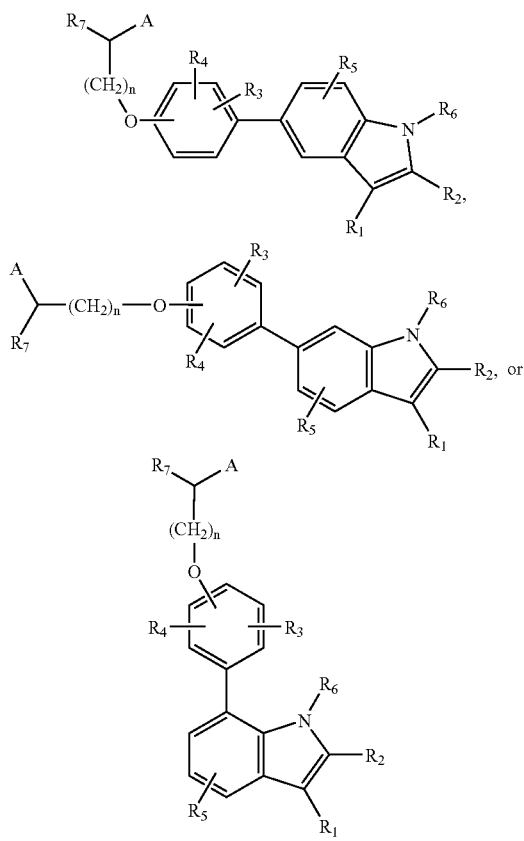

or a pharmaceutically acceptable salt or ester form thereof, wherein:

$R_1$ and $R_2$ are $C_1$-$C_6$ alkyl;

$R_3$, $R_4$ and $R_5$ are, independently, hydrogen, $C_1$-$C_6$ alkyl, $C_3$-$C_5$ cycloalkyl, halogen, hydroxy, $C_6$-$C_{14}$ aryl, $C_1$-$C_3$ perfluoroalkyl, $C_1$-$C_3$ alkoxy, or $C_1$-$C_3$ perfluoroalkoxy;

$R_6$ is hydrogen, $C_1$-$C_6$ alkyl, $C_1$-$C_6$ arylalkyl, $C_1$-$C_6$ alkanoyl, or aroyl;

$R_7$ is hydrogen;

n is an integer of 0-6; and

A is COOH.

14. A compound of claim 1 that is [4-(1,3-Dibenzyl-2-methyl-1H-indol-5-yl)-phenoxy]-acetic acid; [4-(3-Benzyl-1,2-dimethyl-1H-indol-5-yl)-phenoxy]-acetic; [4-(1-Benzyl-3-methyl-2-phenyl-1H-indol-5-yl)-phenoxy]-acetic acid; [4-(1-Benzyl-3-methyl-2-phenyl-1H-indol-6-yl)-phenoxy]-acetic acid or [4-(1-Benzyl-3-methyl-2-phenyl-1H-indol-4-yl)-phenoxy]-acetic acid; or a pharmaceutically acceptable salt or ester form thereof.

15. A compound of claim 1 that is [4-(1,3-Dimethyl-2-phenyl-1H-indol-4-yl)-phenoxy]-acetic acid; [4-(1-Benzyl-3-pentyl-2-phenyl-1H-indol-5-yl)-phenoxyl]-acetic acid; [4-(1-Methyl-3-pentyl-2-phenyl-1H-indol-5-yl)-phenoxy]-acetic acid; [4-(1,3-Dibenzyl-2-phenyl-1H-indol-5-yl)-phenoxy]-acetic acid; or [4-(3-Benzyl-1-methyl-2-phenyl-1H-indol-5-yl)-phenoxy]-acetic acid; or a pharmaceutically acceptable salt or ester form thereof.

16. A compound of claim 1 that is 9-Benzyl-6-[4-(1H-tetrazol-5-ylmethoxy)-phenyl]-2,3,4,9-tetrahydro-1H-carbazole; 4-(9-Benzyl-6,7,8,9-tetrahydro-5H-carbazol-3-yl)-phenoxy]-acetic acid; 9-Methyl-6-[4-(1H-tetrazol-5-ylmethoxy)-phenyl]-2,3,4,9-tetrahydro-1H-carbazole; 1-Benzyl-3-methyl-2-phenyl-4-[4-(1H-tetrazol-5-ylmethoxy)-phenyl]-1H-indole or 1,3-Dimethyl-2-phenyl-4-[4-(1H-tetrazol-5-ylmethoxy)-phenyl]-1H-indole; or a pharmaceutically acceptable salt or ester form thereof.

17. A compound of claim 1 that is 1-Benzyl-2,3-dimethyl-5-[4-(1H-tetrazol-5-ylmethoxy)-phenyl]-1H-indole; 1-Benzyl-3-methyl-2-phenyl-5-[4-(1H-tetrazol-5-ylmethoxy)-phenyl]-1H-indole; 1,3-Dimethyl-2-phenyl-5-[4-(1H-tetrazol-5-ylmethoxy)-phenyl]1H-indole; 1,3-Dibenzyl-2-methyl-5-[4-(1H-tetrazol-5-ylmethoxy)-phenyl]-1H-indole or 3-Benzyl-1,2-dimethyl-5-[4-(1H-tetrazol-5-ylmethoxy)-phenyl]-1H-indole; or a pharmaceutically acceptable salt or ester form thereof.

18. A compound of claim 1 that is 1-Benzyl-3-methyl-2-phenyl-6-[4-(1H-tetrazol-5-ylmethoxy)-phenyl]-1H-indole; 1-Benzyl-3-pentyl-2-phenyl-5-[4-(1H-tetrazol-5-ylmethoxy)-phenyl]-1H-indole; 1-Methyl-3-pentyl-2-phenyl-5-[4-(1H-tetrazol-5-ylmethoxy)-phenyl]-1H-indole; 1,3-Dibenzyl-2-phenyl-5-[4-(1H-tetrazol-5-ylmethoxy)-phenyl]-1H-indole or 3-Benzyl-1-methyl-2-phenyl-5-[4-(1H-tetrazol-5-ylmethoxy)-phenyl]-1H-indole; or a pharmaceutically acceptable salt or ester form thereof.

19. A compound of claim 1 that is [4-(1-Benzyl-2,3-dimethyl-1H-indol 5-yl)-phenoxyl]-acetic acid or a pharmaceutically acceptable salt or ester form thereof.

20. A pharmaceutical composition comprising a compound claim 1; or a pharmaceutically acceptable salt or ester form thereof.

21. A compound of claim 1 wherein the acid mimic is selected from tetrazole, tetronic acid, acyl tetronic acid, or a group of the formula

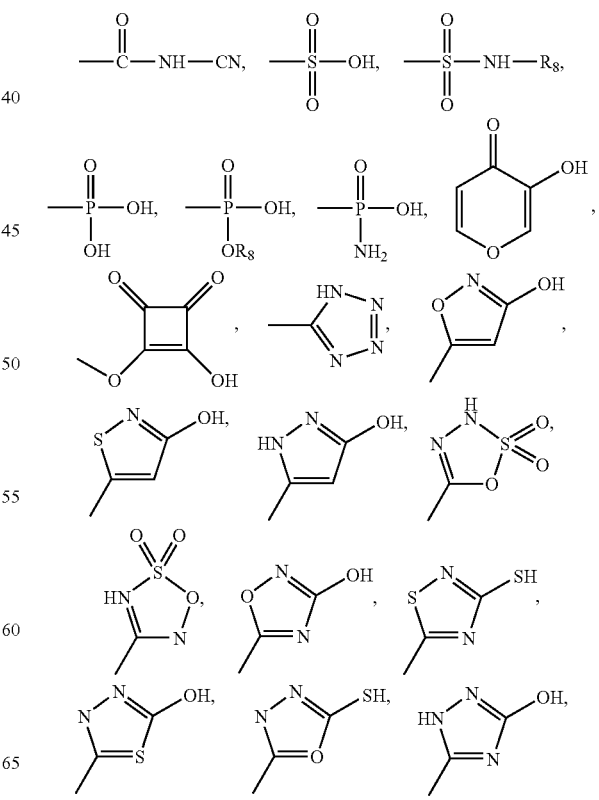

-continued

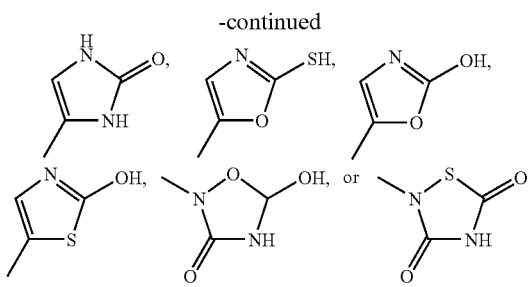

wherein $R^8$ is $C_1$-$C_6$ alkyl, $C_2$-$C_6$ alkenyl, $C_3$-$C_6$ cycloalkyl, —$CH_2$—($C_3$-$C_6$ cycloalkyl), $C_3$-$C_6$ cycloalkenyl, —$CH_2$—($C_3$-$C_6$ cycloalkenyl), aryl, heteroaryl aryl($C_1$-$C_6$)alkyl, or heteroaryl($C_1$-$C_6$)alkyl; or a pharmaceutically acceptable salt or ester form thereof.

22. A method for inhibiting PAI-1 activity in a subject, the method comprising administering to a subject in need thereof a therapeutically effective amount of a compound of claim 1, or a pharmaceutically acceptable salt or ester form thereof.

23. The method of claim 22, wherein the therapeutically effective amount is from 25 mg/kg/day to 200 mg/kg/day.

24. The method of claim 22, wherein the PAI-1 activity is related to a disorder, the disorder is selected from thrombosis, atrial fibrillation, pulmonary fibrosis, myocardial ischemia, thromboembolic complication of surgery, cardiovascular disease caused by noninsulin dependent diabetes mellitus, atherosclerotic plaque formation, chronic obstructive pulmonary disease or renal fibrosis.

25. The method of claim 24, wherein the thrombosis is selected from the group consisting of venous thrombosis, arterial thrombosis, cerebral thrombosis, and deep vein thrombosis.

26. The method of claim 22, wherein the PAI-1 activity is related to stroke.

* * * * *

UNITED STATES PATENT AND TRADEMARK OFFICE
CERTIFICATE OF CORRECTION

PATENT NO. : 7,582,773 B2
APPLICATION NO. : 10/947864
DATED : September 1, 2009
INVENTOR(S) : Eric Gould Gundersen Page 1 of 1

It is certified that error appears in the above-identified patent and that said Letters Patent is hereby corrected as shown below:

Column 52, line 42 and column 53, line 15: please replace each occurrence of:
"A is OOOH or an acid mimic" with
"A is COOH or an acid mimic".

Support for the typographical error is found in the specification as originally filed.

Column 55 lines 40-44: please replace:
"$R_3$, $R_4$ and $R_5$ are, independently, hydrogen, ....$C_3$-$C_5$ cycloalkyl.....or aroyl" with
"$R_3$, $R_4$ and $R_5$ are, independently, hydrogen, ....$C_3$-$C_8$ cycloalkyl.....or aroyl".

Column 55, lines 49-50: please insert the word --acid-- after
"4-(3-Benzyl-1,2-dimethyl-1H-indol-5-yl)-phenoxy]-acetic;".

Signed and Sealed this

Twenty-third Day of March, 2010

David J. Kappos
*Director of the United States Patent and Trademark Office*